US011479770B2

(12) United States Patent
Cacace et al.

(10) Patent No.: US 11,479,770 B2
(45) Date of Patent: Oct. 25, 2022

(54) USE OF P38 INHIBITORS TO REDUCE EXPRESSION OF DUX4

(71) Applicant: Fulcrum Therapeutics, Inc., Cambridge, MA (US)

(72) Inventors: Angela Marie Cacace, Haddam Neck, CT (US); Luis Gustavo Alejandro Rojas Soto, Cambridge, MA (US); Lorin A. Thompson, III, Cohasset, MA (US); Owen Brendan Wallace, Brookline, MA (US); Lucienne V. Ronco, Wellesley, MA (US); Ning Shen, Cambridge, MA (US); Alan Scott Robertson, Cambridge, MA (US); Aaron Nakwon Chang, Lexington, MA (US)

(73) Assignee: Fulcrum Therapeutics, Inc., Cambridge, MA (US)

( * ) Notice: Subject to any disclaimer, the term of this patent is extended or adjusted under 35 U.S.C. 154(b) by 85 days.

(21) Appl. No.: 16/753,664

(22) PCT Filed: Oct. 5, 2018

(86) PCT No.: PCT/US2018/054638
§ 371 (c)(1),
(2) Date: Apr. 3, 2020

(87) PCT Pub. No.: WO2019/071144
PCT Pub. Date: Apr. 11, 2019

(65) Prior Publication Data
US 2020/0332291 A1    Oct. 22, 2020

Related U.S. Application Data

(60) Provisional application No. 62/682,565, filed on Jun. 8, 2018, provisional application No. 62/682,563, filed on Jun. 8, 2018, provisional application No. 62/568,673, filed on Oct. 5, 2017, provisional application No. 62/568,754, filed on Oct. 5, 2017.

(51) Int. Cl.
| | | |
|---|---|---|
| *C12N 15/113* | (2010.01) | |
| *A61P 21/00* | (2006.01) | |
| *A61K 31/4418* | (2006.01) | |
| *A61K 31/4439* | (2006.01) | |
| *A61K 31/506* | (2006.01) | |
| *A61K 31/519* | (2006.01) | |
| *A61K 31/416* | (2006.01) | |
| *A61K 31/437* | (2006.01) | |
| *A61K 31/454* | (2006.01) | |
| *A61K 31/496* | (2006.01) | |
| *A61K 31/513* | (2006.01) | |
| *A61K 31/53* | (2006.01) | |
| *A61K 31/5377* | (2006.01) | |
| *C12Q 1/6827* | (2018.01) | |
| *C12Q 1/686* | (2018.01) | |
| *C12Q 1/6883* | (2018.01) | |
| *A61K 45/06* | (2006.01) | |
| *A61K 9/00* | (2006.01) | |

(52) U.S. Cl.
CPC .......... *C12N 15/113* (2013.01); *A61K 31/416* (2013.01); *A61K 31/437* (2013.01); *A61K 31/4418* (2013.01); *A61K 31/4439* (2013.01); *A61K 31/454* (2013.01); *A61K 31/496* (2013.01); *A61K 31/506* (2013.01); *A61K 31/513* (2013.01); *A61K 31/519* (2013.01); *A61K 31/53* (2013.01); *A61K 31/5377* (2013.01); *A61P 21/00* (2018.01); *C12Q 1/686* (2013.01); *C12Q 1/6827* (2013.01); *C12Q 1/6883* (2013.01); *A61K 9/0019* (2013.01); *A61K 9/0053* (2013.01); *A61K 9/0073* (2013.01); *A61K 45/06* (2013.01); *C12Q 2600/106* (2013.01); *C12Q 2600/156* (2013.01)

(58) Field of Classification Search
CPC ..... A61K 31/00; A61P 21/00; C07K 14/4707; C12N 9/13; C12N 15/113; C12Q 1/6883
USPC ..................... 435/6.1, 91.1, 91.31, 455, 458; 514/44 A, 44 R; 536/23.1, 24.5; 424/9.1
See application file for complete search history.

(56) References Cited

U.S. PATENT DOCUMENTS

| | | |
|---|---|---|
| 4,522,811 A | 6/1985 | Eppstein et al. |
| 5,670,527 A | 9/1997 | Adams et al. |
| 5,716,955 A | 2/1998 | Adams et al. |

(Continued)

FOREIGN PATENT DOCUMENTS

| | | |
|---|---|---|
| DE | 10255040 A1 | 6/2004 |
| EP | 1247810 A1 | 10/2002 |

(Continued)

OTHER PUBLICATIONS

Underwood et al (J. Pharmacol. & Expr. Therapeutics, vol. 293, No. 1, pp. 281-288 (2000)). (Year: 2000).*

(Continued)

*Primary Examiner* — Jane J Zara
(74) *Attorney, Agent, or Firm* — Goodwin Procter LLP

(57) ABSTRACT

The present invention relates to compositions and methods of inhibiting p38 kinase to reduce gene and protein expression of DUX4 and downstream genes regulated by DUX4. The present invention further relates to methods for treating patients suffering from diseases associated with increased expression of DUX4 or expression of an aberrant form of DUX4, such as Facioscapulohumeral muscular dystrophy (FSHD).

8 Claims, 26 Drawing Sheets

Specification includes a Sequence Listing.

(56) References Cited

U.S. PATENT DOCUMENTS

| | | | |
|---|---|---|---|
| 6,096,753 A | 8/2000 | Spohr et al. |
| 6,147,080 A | 11/2000 | Bemis et al. |
| 6,218,537 B1 | 4/2001 | Adams et al. |
| 6,319,921 B1 | 11/2001 | Cirillo et al. |
| 6,340,685 B1 | 1/2002 | Mavunkel et al. |
| 6,369,068 B1 | 4/2002 | Adams et al. |
| 6,448,257 B1 | 9/2002 | Mavunkel et al. |
| 6,476,031 B1 | 11/2002 | Chakravarty et al. |
| 6,589,954 B1 | 7/2003 | Mavunkel et al. |
| 6,696,566 B2 | 2/2004 | Chen et al. |
| 6,867,209 B1 | 3/2005 | Mavunkel et al. |
| 7,115,746 B2 | 10/2006 | Snoonian et al. |
| 7,125,898 B2 | 10/2006 | Aston et al. |
| 7,160,883 B2 | 1/2007 | Dyckman et al. |
| 7,276,527 B2 | 10/2007 | Ohkawa et al. |
| 7,314,881 B2 | 1/2008 | Adams et al. |
| 7,323,472 B2 | 1/2008 | Adams et al. |
| 7,462,616 B2 | 12/2008 | Dyckman et al. |
| 7,473,784 B2 | 1/2009 | Liu et al. |
| 7,521,447 B2 | 4/2009 | Munson et al. |
| 7,582,652 B2 | 9/2009 | Bonjouklian et al. |
| 7,759,337 B2 | 7/2010 | Tasker et al. |
| 7,759,343 B2 | 7/2010 | Dyckman et al. |
| 8,003,657 B2 | 8/2011 | Stieber et al. |
| 8,044,083 B2 | 10/2011 | Groneberg et al. |
| 8,058,282 B2 | 11/2011 | Adams et al. |
| 8,202,899 B2 | 6/2012 | Munson et al. |
| 8,314,131 B2 | 11/2012 | Pettus et al. |
| 8,367,671 B2 | 2/2013 | Tasker et al. |
| 8,420,649 B2 | 4/2013 | Pettus et al. |
| 8,450,314 B2 | 5/2013 | Beswick et al. |
| 8,497,269 B2 | 7/2013 | Tasker et al. |
| 8,513,289 B2 | 8/2013 | Koyama et al. |
| 8,557,797 B2 | 10/2013 | Finch et al. |
| 8,633,312 B2 | 1/2014 | Laufer et al. |
| 8,772,481 B2 | 7/2014 | Tasker et al. |
| 8,846,931 B2 | 9/2014 | Hoelzemann et al. |
| 8,916,708 B2 | 12/2014 | Woo et al. |
| 9,051,318 B2 | 6/2015 | Dorsch et al. |
| 9,427,439 B1 | 8/2016 | Alam |
| 10,342,786 B2 | 7/2019 | Cacace et al. |
| 10,537,560 B2 | 1/2020 | Cacace et al. |
| 10,973,805 B2 | 4/2021 | Efremov et al. |
| 2002/0115671 A1 | 8/2002 | Goehring et al. |
| 2002/0137747 A1 | 9/2002 | Moriarty et al. |
| 2003/0229081 A1 | 12/2003 | Maduskuie |
| 2003/0236193 A1 | 12/2003 | Oliner et al. |
| 2004/0033222 A1 | 2/2004 | Wood et al. |
| 2004/0067996 A1 | 4/2004 | Sheppeck |
| 2004/0077682 A1 | 4/2004 | Dombroski et al. |
| 2004/0087615 A1 | 5/2004 | Dombroski et al. |
| 2004/0092547 A1 | 5/2004 | Dombroski et al. |
| 2004/0097493 A1 | 5/2004 | Chen et al. |
| 2004/0157846 A1 | 8/2004 | Chen et al. |
| 2004/0157877 A1 | 8/2004 | Dombroski et al. |
| 2004/0176325 A1 | 9/2004 | Munson et al. |
| 2004/0192653 A1 | 9/2004 | Munson et al. |
| 2004/0209886 A1 | 10/2004 | Salvati et al. |
| 2004/0209903 A1 | 10/2004 | Dewdney et al. |
| 2004/0209904 A1 | 10/2004 | Dunn et al. |
| 2004/0242602 A1 | 12/2004 | Gungor et al. |
| 2005/0020587 A1 | 1/2005 | Bailey et al. |
| 2005/0020626 A1 | 1/2005 | Mathias |
| 2005/0026952 A1 | 2/2005 | Mathias |
| 2005/0043306 A1 | 2/2005 | Leftheris et al. |
| 2005/0107408 A1 | 5/2005 | Goldstein |
| 2005/0176775 A1 | 8/2005 | Devadas et al. |
| 2005/0176965 A1 | 8/2005 | Chen et al. |
| 2005/0277681 A1 | 12/2005 | Hanney et al. |
| 2005/0288299 A1 | 12/2005 | Mavunkel et al. |
| 2006/0019928 A1 | 1/2006 | Lin et al. |
| 2006/0035922 A1 | 2/2006 | Mathias et al. |
| 2006/0052390 A1 | 3/2006 | Schreiner et al. |
| 2006/0058296 A1 | 3/2006 | Higgins et al. |
| 2006/0079461 A1 | 4/2006 | Brewer et al. |
| 2006/0111416 A1 | 5/2006 | Lane et al. |
| 2006/0217401 A1 | 9/2006 | Boehm et al. |
| 2006/0235020 A1 | 10/2006 | Kim et al. |
| 2008/0146590 A1 | 6/2008 | Gabriel et al. |
| 2008/0207684 A1 | 8/2008 | Gabriel et al. |
| 2008/0275052 A1 | 11/2008 | Dhar et al. |
| 2009/0041722 A1 | 2/2009 | Liu et al. |
| 2009/0042856 A1 | 2/2009 | Yamazaki et al. |
| 2009/0312331 A1 | 12/2009 | Kim et al. |
| 2010/0093734 A1 | 4/2010 | Boman et al. |
| 2011/0117055 A1 | 5/2011 | MacDonald et al. |
| 2011/0166154 A1 | 7/2011 | Slamon et al. |
| 2011/0250197 A1 | 10/2011 | Sattigeri et al. |
| 2012/0108594 A1 | 5/2012 | Kim et al. |
| 2012/0157500 A1 | 6/2012 | Tao |
| 2014/0069419 A1 | 3/2014 | Ghidini |
| 2014/0296208 A1 | 10/2014 | Baker et al. |
| 2015/0087636 A1 | 3/2015 | Sverdrup |
| 2015/0225373 A1 | 8/2015 | Fyfe et al. |
| 2015/0232449 A1 | 8/2015 | Juhl et al. |
| 2016/0016934 A1 | 1/2016 | Fyfe |
| 2016/0166587 A1 | 6/2016 | Simpson et al. |
| 2016/0220550 A1 | 8/2016 | Sprecher et al. |
| 2017/0073343 A1 | 3/2017 | Galatsis et al. |
| 2020/0332291 A1 | 10/2020 | Cacace et al. |

FOREIGN PATENT DOCUMENTS

| | | |
|---|---|---|
| EP | 1538201 A1 | 6/2005 |
| EP | 1574501 A1 | 9/2005 |
| EP | 1577291 A1 | 9/2005 |
| EP | 1577292 A1 | 9/2005 |
| EP | 1609789 A1 | 12/2005 |
| EP | 2036905 A1 | 3/2009 |
| EP | 2044957 A1 | 4/2009 |
| EP | 2123255 A1 | 11/2009 |
| EP | 3381472 A1 | 10/2018 |
| JP | 2009-263234 A | 11/2009 |
| WO | 96/21452 A1 | 7/1996 |
| WO | 96/40143 A1 | 12/1996 |
| WO | 97/025046 A1 | 7/1997 |
| WO | 97/25047 A1 | 7/1997 |
| WO | 97/25048 A1 | 7/1997 |
| WO | 97/32583 A1 | 9/1997 |
| WO | 97/33883 A1 | 9/1997 |
| WO | 97/34137 A2 | 9/1997 |
| WO | 97/35855 A1 | 10/1997 |
| WO | 97/35856 A1 | 10/1997 |
| WO | 98/07425 A1 | 2/1998 |
| WO | 98/027098 A1 | 6/1998 |
| WO | 98/28292 A1 | 7/1998 |
| WO | 98/047892 A1 | 10/1998 |
| WO | 98/56377 A1 | 12/1998 |
| WO | 98/57966 A1 | 12/1998 |
| WO | 99/00357 A1 | 1/1999 |
| WO | 99/01130 A1 | 1/1999 |
| WO | 99/01136 A1 | 1/1999 |
| WO | 99/20624 A1 | 4/1999 |
| WO | 99/21859 A1 | 5/1999 |
| WO | 99/42592 A1 | 8/1999 |
| WO | 99/057101 A1 | 11/1999 |
| WO | 99/58502 A1 | 11/1999 |
| WO | 99/61426 A1 | 12/1999 |
| WO | 99/61437 A1 | 12/1999 |
| WO | 99/64400 A1 | 12/1999 |
| WO | 00/010563 A1 | 3/2000 |
| WO | 00/012497 A2 | 3/2000 |
| WO | 00/017175 A1 | 3/2000 |
| WO | 00/019824 A1 | 4/2000 |
| WO | 00/025791 A1 | 5/2000 |
| WO | 00/031063 A1 | 6/2000 |
| WO | 2000/43384 A1 | 7/2000 |
| WO | 00/059904 A2 | 10/2000 |
| WO | 00/071535 A1 | 11/2000 |
| WO | 01/004115 A2 | 1/2001 |
| WO | 01/019322 A2 | 3/2001 |
| WO | 01/021591 A1 | 3/2001 |
| WO | 01/029041 A1 | 4/2001 |
| WO | 01/029042 A1 | 4/2001 |

(56) References Cited

FOREIGN PATENT DOCUMENTS

| | | |
|---|---|---|
| WO | 01/037837 A1 | 5/2001 |
| WO | 01/038313 A1 | 5/2001 |
| WO | 01/038314 A1 | 5/2001 |
| WO | 01/047897 A1 | 7/2001 |
| WO | 01/064676 A2 | 9/2001 |
| WO | 01/064679 A1 | 9/2001 |
| WO | 01/038312 A2 | 11/2001 |
| WO | 02/007772 A2 | 1/2002 |
| WO | 02/016359 A1 | 2/2002 |
| WO | 02/018379 A2 | 3/2002 |
| WO | 02/018380 A1 | 3/2002 |
| WO | 02/032862 A2 | 4/2002 |
| WO | 02/040486 A2 | 5/2002 |
| WO | 02/042292 A2 | 5/2002 |
| WO | 02/044168 A2 | 6/2002 |
| WO | 02/045752 A2 | 6/2002 |
| WO | 02/046158 A2 | 6/2002 |
| WO | 02/058695 A1 | 8/2002 |
| WO | 02/059083 A2 | 8/2002 |
| WO | 02/060869 A2 | 8/2002 |
| WO | 02/064594 A2 | 8/2002 |
| WO | 02/069892 A2 | 9/2002 |
| WO | 02/072576 A1 | 9/2002 |
| WO | 02/072579 A1 | 9/2002 |
| WO | 02/076396 A2 | 10/2002 |
| WO | 02/076463 A1 | 10/2002 |
| WO | 02/076954 A1 | 10/2002 |
| WO | 02/076984 A1 | 10/2002 |
| WO | 02/076985 A1 | 10/2002 |
| WO | 02/085405 A2 | 10/2002 |
| WO | 02/090360 A1 | 11/2002 |
| WO | 02/092087 A1 | 11/2002 |
| WO | 02/094833 A1 | 11/2002 |
| WO | 02/100405 A1 | 12/2002 |
| WO | 03/000682 A1 | 1/2003 |
| WO | 03/002544 A1 | 1/2003 |
| WO | 03/005999 A2 | 1/2003 |
| WO | 03/015828 A1 | 2/2003 |
| WO | 03/020715 A1 | 3/2003 |
| WO | 03/026568 A2 | 4/2003 |
| WO | 03/032894 A2 | 4/2003 |
| WO | 03/032970 A1 | 4/2003 |
| WO | 03/032971 A1 | 4/2003 |
| WO | 03/032972 A1 | 4/2003 |
| WO | 03/032980 A1 | 4/2003 |
| WO | 03/032986 A1 | 4/2003 |
| WO | 03/032987 A1 | 4/2003 |
| WO | 03/033482 A1 | 4/2003 |
| WO | 03/033483 A1 | 4/2003 |
| WO | 03/039534 A1 | 5/2003 |
| WO | 03/041644 A2 | 5/2003 |
| WO | 03/048340 A2 | 6/2003 |
| WO | 03/049742 A1 | 6/2003 |
| WO | 03/057197 A1 | 7/2003 |
| WO | 03/059293 A2 | 7/2003 |
| WO | 03/064417 A1 | 8/2003 |
| WO | 03/064418 A1 | 8/2003 |
| WO | 03/064419 A1 | 8/2003 |
| WO | 03/068223 A1 | 8/2003 |
| WO | 03/068747 A1 | 8/2003 |
| WO | 03/074530 A1 | 9/2003 |
| WO | 03/077919 A1 | 9/2003 |
| WO | 03/082208 A2 | 10/2003 |
| WO | 03/082871 A1 | 10/2003 |
| WO | 03/084503 A2 | 10/2003 |
| WO | 03/084539 A2 | 10/2003 |
| WO | 03/087096 A1 | 10/2003 |
| WO | 03/087394 A1 | 10/2003 |
| WO | 03/088972 A1 | 10/2003 |
| WO | 03/090912 A1 | 11/2003 |
| WO | 03/091229 A1 | 11/2003 |
| WO | 03/092588 A2 | 11/2003 |
| WO | 03/093248 A1 | 11/2003 |
| WO | 03/097615 A1 | 11/2003 |
| WO | 03/099206 A2 | 12/2003 |
| WO | 03/099820 A1 | 12/2003 |
| WO | 03/103590 A2 | 12/2003 |
| WO | 2004/004725 A2 | 1/2004 |
| WO | 2004/010929 A2 | 2/2004 |
| WO | 2004/010995 A1 | 2/2004 |
| WO | 2004/014387 A1 | 2/2004 |
| WO | 2004/014870 A1 | 2/2004 |
| WO | 2004/014900 A1 | 2/2004 |
| WO | 2004/014907 A1 | 2/2004 |
| WO | 2004/019873 A2 | 3/2004 |
| WO | 2004/020438 A2 | 3/2004 |
| WO | 2004/020440 A1 | 3/2004 |
| WO | 2004/021979 A2 | 3/2004 |
| WO | 2004/021988 A2 | 3/2004 |
| WO | 2004/022712 A2 | 3/2004 |
| WO | 2004/024699 A1 | 3/2004 |
| WO | 2004/026871 A1 | 4/2004 |
| WO | 2004/029040 A1 | 4/2004 |
| WO | 2004/032874 A2 | 4/2004 |
| WO | 2004/041277 A1 | 5/2004 |
| WO | 2004/048373 A1 | 6/2004 |
| WO | 2004/053107 A2 | 6/2004 |
| WO | 2004/069793 A2 | 8/2004 |
| WO | 2004/072038 A1 | 8/2004 |
| WO | 2004/072072 A1 | 8/2004 |
| WO | 2004/073628 A2 | 9/2004 |
| WO | 2004/076450 A1 | 9/2004 |
| WO | 2004/089874 A1 | 10/2004 |
| WO | 2004/089875 A1 | 10/2004 |
| WO | 2004/089876 A1 | 10/2004 |
| WO | 2004/098518 A2 | 11/2004 |
| WO | 2004/098528 A2 | 11/2004 |
| WO | 2004/099156 A1 | 11/2004 |
| WO | 2004/100874 A2 | 11/2004 |
| WO | 2004/100946 A1 | 11/2004 |
| WO | 2004/108675 A1 | 12/2004 |
| WO | 2005/005380 A2 | 1/2005 |
| WO | 2005/005606 A2 | 1/2005 |
| WO | 2005/009367 A2 | 2/2005 |
| WO | 2005/009965 A1 | 2/2005 |
| WO | 2005/009966 A1 | 2/2005 |
| WO | 2005/009973 A1 | 2/2005 |
| WO | 2005/012875 A2 | 2/2005 |
| WO | 2005/014550 A1 | 2/2005 |
| WO | 2005/018557 A2 | 3/2005 |
| WO | 2005/018624 A2 | 3/2005 |
| WO | 2005/023201 A2 | 3/2005 |
| WO | 2005/023761 A2 | 3/2005 |
| WO | 2005/025572 A1 | 3/2005 |
| WO | 2005/032481 A2 | 4/2005 |
| WO | 2005/032551 A1 | 4/2005 |
| WO | 2005/033072 A2 | 4/2005 |
| WO | 2005/042537 A1 | 5/2005 |
| WO | 2005/058308 A2 | 6/2005 |
| WO | 2005/060967 A1 | 7/2005 |
| WO | 2005/063715 A1 | 7/2005 |
| WO | 2005/065691 A1 | 7/2005 |
| WO | 2005/073189 A1 | 8/2005 |
| WO | 2005/073217 A1 | 8/2005 |
| WO | 2005/073219 A1 | 8/2005 |
| WO | 2005/073232 A1 | 8/2005 |
| WO | 2005/075425 A2 | 8/2005 |
| WO | 2005/075478 A1 | 8/2005 |
| WO | 2005/077945 A2 | 8/2005 |
| WO | 2005/080380 A1 | 9/2005 |
| WO | 2005/082862 A2 | 9/2005 |
| WO | 2005/085206 A1 | 9/2005 |
| WO | 2005/085248 A1 | 9/2005 |
| WO | 2005/090288 A1 | 9/2005 |
| WO | 2005/091891 A2 | 10/2005 |
| WO | 2005/105091 A1 | 11/2005 |
| WO | 2005/110455 A2 | 11/2005 |
| WO | 2006/009741 A1 | 1/2006 |
| WO | 2006/015775 A2 | 2/2006 |
| WO | 2006/020904 A1 | 2/2006 |
| WO | 2006/026196 A2 | 3/2006 |
| WO | 2006/039718 A2 | 4/2006 |
| WO | 2006/040056 A1 | 4/2006 |
| WO | 2006/044860 A2 | 4/2006 |

(56) References Cited

FOREIGN PATENT DOCUMENTS

| | | |
|---|---|---|
| WO | 2006/048266 A2 | 5/2006 |
| WO | 2006/051373 A1 | 5/2006 |
| WO | 2006/051375 A1 | 5/2006 |
| WO | 2006/055302 A2 | 5/2006 |
| WO | 2006/055404 A2 | 5/2006 |
| WO | 2006/058023 A2 | 6/2006 |
| WO | 2006/060108 A1 | 6/2006 |
| WO | 2006/063856 A1 | 6/2006 |
| WO | 2006/067165 A2 | 6/2006 |
| WO | 2006/067168 A1 | 6/2006 |
| WO | 2006/067175 A1 | 6/2006 |
| WO | 2006/070927 A1 | 7/2006 |
| WO | 2006/084017 A2 | 8/2006 |
| WO | 2006/089798 A1 | 8/2006 |
| WO | 2006/094187 A2 | 9/2006 |
| WO | 2006/104889 A2 | 10/2006 |
| WO | 2006/104915 A2 | 10/2006 |
| WO | 2006/110173 A2 | 10/2006 |
| WO | 2006/122230 A1 | 11/2006 |
| WO | 2006/127678 A2 | 11/2006 |
| WO | 2006/134382 A1 | 12/2006 |
| WO | 2007/005863 A1 | 1/2007 |
| WO | 2007/016358 A1 | 2/2007 |
| WO | 2007/016392 A2 | 2/2007 |
| WO | 2007/021710 A1 | 2/2007 |
| WO | 2007/023105 A1 | 3/2007 |
| WO | 2007/023110 A2 | 3/2007 |
| WO | 2007/023111 A2 | 3/2007 |
| WO | 2007/023114 A1 | 3/2007 |
| WO | 2007/023115 A2 | 3/2007 |
| WO | 2007/024754 A1 | 3/2007 |
| WO | 2007/034325 A1 | 3/2007 |
| WO | 2007/038444 A2 | 4/2007 |
| WO | 2007/045989 A1 | 4/2007 |
| WO | 2007/052124 A1 | 5/2007 |
| WO | 2007/053346 A1 | 5/2007 |
| WO | 2007/053394 A1 | 5/2007 |
| WO | 2007/056016 A2 | 5/2007 |
| WO | 2007/059500 A2 | 5/2007 |
| WO | 2007/072163 A2 | 6/2007 |
| WO | 2007/075896 A2 | 7/2007 |
| WO | 2007/084391 A2 | 7/2007 |
| WO | 2007/089646 A1 | 8/2007 |
| WO | 2007/091152 A1 | 8/2007 |
| WO | 2007/091176 A1 | 8/2007 |
| WO | 2007/096151 A2 | 8/2007 |
| WO | 2007/103468 A2 | 9/2007 |
| WO | 2007/103839 A2 | 9/2007 |
| WO | 2007/107828 A2 | 9/2007 |
| WO | 2007/115670 A1 | 10/2007 |
| WO | 2007/124181 A2 | 11/2007 |
| WO | 2007/126871 A1 | 11/2007 |
| WO | 2007/144390 A1 | 12/2007 |
| WO | 2007/146712 A2 | 12/2007 |
| WO | 2007/147103 A2 | 12/2007 |
| WO | 2007/147104 A2 | 12/2007 |
| WO | 2007/147109 A2 | 12/2007 |
| WO | 2008/001929 A1 | 1/2008 |
| WO | 2008/001930 A1 | 1/2008 |
| WO | 2008/011032 A1 | 1/2008 |
| WO | 2008/013823 A2 | 1/2008 |
| WO | 2008/021388 A1 | 2/2008 |
| WO | 2008/024391 A1 | 2/2008 |
| WO | 2008/041095 A1 | 4/2008 |
| WO | 2008/045393 A2 | 4/2008 |
| WO | 2008/048540 A2 | 4/2008 |
| WO | 2008/049842 A2 | 5/2008 |
| WO | 2008/071664 A1 | 6/2008 |
| WO | 2008/071665 A1 | 6/2008 |
| WO | 2008/072079 A2 | 6/2008 |
| WO | 2008/076265 A1 | 6/2008 |
| WO | 2008/079857 A1 | 7/2008 |
| WO | 2008/089034 A2 | 7/2008 |
| WO | 2008/098096 A1 | 8/2008 |
| WO | 2008/099615 A1 | 8/2008 |
| WO | 2008/103276 A2 | 8/2008 |
| WO | 2008/105808 A2 | 9/2008 |
| WO | 2008/135819 A1 | 11/2008 |
| WO | 2008/136948 A1 | 11/2008 |
| WO | 2008/137176 A1 | 11/2008 |
| WO | 2009/011871 A2 | 1/2009 |
| WO | 2009/011880 A2 | 1/2009 |
| WO | 2009/015000 A1 | 1/2009 |
| WO | 2009/015169 A1 | 1/2009 |
| WO | 2009/034432 A2 | 3/2009 |
| WO | 2009/038784 A1 | 3/2009 |
| WO | 2009/069032 A2 | 6/2009 |
| WO | 2009/074518 A1 | 6/2009 |
| WO | 2009/074519 A1 | 6/2009 |
| WO | 2009/078992 A1 | 6/2009 |
| WO | 2009/094556 A2 | 7/2009 |
| WO | 2009/103336 A1 | 8/2009 |
| WO | 2009/117156 A1 | 9/2009 |
| WO | 2009/152072 A1 | 12/2009 |
| WO | 2009/155388 A1 | 12/2009 |
| WO | 2009/155389 A1 | 12/2009 |
| WO | 2009/158446 A2 | 12/2009 |
| WO | 2009/158450 A1 | 12/2009 |
| WO | 2010/004517 A1 | 1/2010 |
| WO | 2010/007552 A1 | 1/2010 |
| WO | 2010/007561 A1 | 1/2010 |
| WO | 2010/025201 A1 | 3/2010 |
| WO | 2010/025202 A1 | 3/2010 |
| WO | 2010/038428 A1 | 4/2010 |
| WO | 2010/040843 A2 | 4/2010 |
| WO | 2010/042646 A1 | 4/2010 |
| WO | 2010/042649 A2 | 4/2010 |
| WO | 2010/083246 A1 | 7/2010 |
| WO | 2010/089391 A1 | 8/2010 |
| WO | 2010/093889 A2 | 8/2010 |
| WO | 2010/093890 A2 | 8/2010 |
| WO | 2010/120963 A1 | 10/2010 |
| WO | 2010/129208 A1 | 11/2010 |
| WO | 2011/050192 A1 | 4/2011 |
| WO | 2011/083387 A1 | 7/2011 |
| WO | 2011/119848 A1 | 9/2011 |
| WO | 2011/119863 A1 | 9/2011 |
| WO | 2011/154738 A1 | 12/2011 |
| WO | 2012/000595 A1 | 1/2012 |
| WO | 2012/003912 A1 | 1/2012 |
| WO | 2012/031057 A1 | 3/2012 |
| WO | 2012/074761 A1 | 6/2012 |
| WO | 2012/074933 A1 | 6/2012 |
| WO | 2012/119690 A1 | 9/2012 |
| WO | 2012/154814 A1 | 11/2012 |
| WO | 2012/168359 A1 | 12/2012 |
| WO | 2013/007708 A1 | 1/2013 |
| WO | 2013/070460 A1 | 5/2013 |
| WO | 2013/083206 A1 | 6/2013 |
| WO | 2013/083604 A1 | 6/2013 |
| WO | 2013/083606 A1 | 6/2013 |
| WO | 2013/086002 A1 | 6/2013 |
| WO | 2013/106643 A2 | 7/2013 |
| WO | 2013/130573 A1 | 9/2013 |
| WO | 2013/139809 A1 | 9/2013 |
| WO | 2013/174780 A1 | 11/2013 |
| WO | 2014/014706 A1 | 1/2014 |
| WO | 2014/027209 A1 | 2/2014 |
| WO | 2014/033446 A1 | 3/2014 |
| WO | 2014/033447 A2 | 3/2014 |
| WO | 2014/033448 A1 | 3/2014 |
| WO | 2014/033449 A1 | 3/2014 |
| WO | 2014/076484 A1 | 5/2014 |
| WO | 2014/083026 A1 | 6/2014 |
| WO | 2014/134313 A1 | 9/2014 |
| WO | 2014/140582 A1 | 9/2014 |
| WO | 2014/155135 A1 | 10/2014 |
| WO | 2014/181213 A1 | 11/2014 |
| WO | 2014/194956 A1 | 12/2014 |
| WO | 2014/195400 A1 | 12/2014 |
| WO | 2014/195402 A1 | 12/2014 |
| WO | 2015/004089 A1 | 1/2015 |
| WO | 2015/006752 A1 | 1/2015 |
| WO | 2015/006753 A2 | 1/2015 |

(56) References Cited

FOREIGN PATENT DOCUMENTS

| | | |
|---|---|---|
| WO | 2015/091889 A1 | 6/2015 |
| WO | 2015/092423 A1 | 6/2015 |
| WO | 2015/121444 A1 | 8/2015 |
| WO | 2015/121660 A1 | 8/2015 |
| WO | 2015/191986 A1 | 12/2015 |
| WO | 2015/191996 A1 | 12/2015 |
| WO | 2016/007616 A1 | 1/2016 |
| WO | 2016/049677 A1 | 4/2016 |
| WO | 2016/051186 A1 | 4/2016 |
| WO | 2016/051187 A1 | 4/2016 |
| WO | 2016/051188 A1 | 4/2016 |
| WO | 2016/066687 A1 | 5/2016 |
| WO | 2016/114655 A1 † | 7/2016 |
| WO | 2016/115490 A1 | 7/2016 |
| WO | 2016/124793 A1 | 8/2016 |
| WO | 2016/128456 A1 | 8/2016 |
| WO | 2016/142310 A1 | 9/2016 |
| WO | 2016/159301 A1 | 10/2016 |
| WO | 2016/166239 A1 | 10/2016 |
| WO | 2016/198698 A2 | 12/2016 |
| WO | 2017/075013 A1 | 5/2017 |
| WO | 2017/093208 A1 | 6/2017 |
| WO | 2017/108736 A1 | 6/2017 |
| WO | 2017/110093 A1 | 6/2017 |
| WO | 2017/117182 A1 | 7/2017 |
| WO | 2017/134053 A1 | 8/2017 |
| WO | 2017/136480 A1 | 8/2017 |
| WO | 2017/211830 A1 | 12/2017 |
| WO | 2018/007788 A1 | 1/2018 |
| WO | 2018/148797 A1 | 8/2018 |
| WO | 2019/103926 A1 | 5/2019 |
| WO | 2020/106876 A2 | 5/2020 |

OTHER PUBLICATIONS

Barbour et al (BJCP, vol. 76, No. 1, pp. 99-106 (2012)). (Year: 2012).*
Aouadi, M. et al., "Role of MAPKs in development and differentiation: lessons from knockout mice," Biochimie. 88(9):1091-1098 (2006).
Aston, N. M. et al., "p38a Mitogen-Activated Protein Kinase Inhibitors: Optimization of a Series of Biphenylamides to Give a Molecule Suitable for Clinical Progression," J. Med. Chem. 52(20):6257-6269 (2009).
Bosnakovski, D. et al., "High-throughput screening identifies inhibitors of DUX4-induced myoblast toxicity," Skeletal Muscle, 4(4) (2014), 11 pages; Retrieved from http://www.skeletalmusclejournal.com/contenUl/1/1.
Boudou, T. et al., "A Microfabricated Platform to Measure and Manipulate the Mechanics of Engineered Cardiac Microtissues," Tissue Engineering: Part A, 18(9,10):910-616 (2012).
Cuadrado, A & Nebreda, AR., "Mechanisms and functions of p38 MAPK signalling," Biochem J., 429(3):403-417 (2010).
Cuenda, A & Rousseau, S., "p38 MAP-Kinases pathway regulation, function and role in human diseases," Biochimica et Biophysica Acta 1773:1358-1375 (2007).
Dalkilic, I. & Kunkel, L. M., "Muscular dystrophies: genes to pathogenesis," Current Opinion in Genetics & Development, 13:231-238 (2003).
Dandapat, A et al., "Expression of the Human FSHD-Linked DUX4 Gene Induces Neurogenesis During Differentiation of Murine Embryonic Stem Cells," Stem Cells and Development, 22(17):2440-2448 (2013).
Ehrlich, M. & Lacey, M., "Deciphering transcription dysregulation in FSH muscular dystrophy," Journal of Human Genetics, 57(8):477-484 (2012).
Esvelt, K. M. et al., "Orthogonal Cas9 Proteins for RNA-Guided Gene Regulation and Editing," Nat Methods, 10(11):1116-1121 (2013).
GenBank Accession No. NC_000019.10, Mar. 26, 2018.
GenBank Accession No. NG_034189.2, Dec. 24, 2018.
GenBank Accession No. NM_001126063.2, Jun. 23, 2018.
GenBank Accession No. NM_001143832.1, Jun. 24, 2018.
GenBank Accession No. NM_001293798.2, Dec. 23, 2018.
GenBank Accession No. NM_001315.2, Dec. 23, 2018.
GenBank Accession No. NM_002751.6, Aug. 19, 2018.
GenBank Accession No. NM_023014.1, Jun. 23, 2018.
GenBank Accession No. NM_144614.3, Jun. 23, 2018.
GenBank Accession No. NM_152677.2, Dec. 23, 2018.
GenBank Accession No. NP_001119535.1, Dec. 23, 2018.
GenBank Accession No. NP_001137304.1, Jun. 24, 2018.
GenBank Accession No. NP_001280727.1, Dec. 23, 2018.
GenBank Accession No. NP_001306.1, Dec. 23, 2018.
GenBank Accession No. NP_002742.3, Nov. 23, 2018.
GenBank Accession No. NP_075390.1, Jun. 23, 2018.
GenBank Accession No. NP_620155.1, Jul. 1, 2018.
GenBank Accession No. NP_653215.2, Jun. 23, 2018.
GenBank Accession No. NP_689890.1, Dec. 23, 2018.
GenBank Accession No. NC_000001.11, Mar. 26, 2018.
GenBank Accession No. NC_000002.12, Mar. 26, 2018.
GenBank Accession No. NC_000006.12, Mar. 26, 2018.
GenBank Accession No. NM_138800.2, Jul. 1, 2018.
Geng, L. N. et al., "DUX4 Activates Germline Genes, Retroelements, and Immune Mediators: Implications for Facioscapulohumeral Dystrophy," Developmental Cell, 22(1):38-51 (2012).
Himeda, C. L. et al., "CRISPR/dCas9-mediated Transcriptional Inhibition Ameliorates the Epigenetic Dysregulation of D4Z4 and Represses DUX4-fl in FSH Muscular Dystrophy," Molecular Therapy, 24(3):527-533 (2016).
Himeda, C. L. et al., "Facioscapulohumeral Muscular Dystrophy as a Model for Epigenetic Regulation and Disease," Antioxidants & Redox Signaling, 22(16):1463-1482 (2015).
Himeda, C. L. et al., "Myogenic enhancers regulate expression of the Facioscapulohumeral muscular dystrophy associated DUX4 gene," Mol. Cell. Biol., 34(11):1942-1955 (2014).
Homma, S. et al., "Expression of FSHD-related DUX4-FL alters proteostasis and induces TDP-43 aggregation," Annals of Clinical and Translational Neurology, 2(2):151-166 (2015).
https://www.fishersci.com/shop/products/eo-1 428-tocris-2/29081 0. Accessed Apr. 26, 2019.
International Search Report and Written Opinion dated Jan. 25, 2019 for International Application No. PCT/US2018/054638, 16 pages.
International Search Report and Written Opinion dated Jan. 30, 2019 for International Application No. PCT/US2018/054642, 11 pages.
Ishizawa, T. et al., "Substituent Effects of Benzopyran-4-(N-Cyano)-Carboxamidine Potassium Channel Openers for Selectivity to Guinea Pig Trachealis," Bioorganic & Medicinal Chemistry Letters, 4(16):1995-1998 (1994).
Keren, A. et al., "The p38 MAPK signaling pathway: A major regulator of skeletal muscle development," Molecular and Cellular Endocrinology, 252:224-230 (2006).
Kim, D. et al., "TopHat2: accurate alignment of transcriptomes in the presence of insertions, deletions and gene fusions," Genome Biology, 14:R36, (2013), 13 pages; Retrieved from http://qenomebioloqv.com/2013/14/4/R36.
Kimmel, A. R., "Identification and Characterization of Specific Clones: Strategy for Confirming the Validity of Presumptive Clones," Methods in Enzymology, 152:507-511 (1987).
Krementsov, D. N et al., "The Emerging Role of p38 Mitogen-Activated Protein Kinase in Multiple Sclerosis and Its Models," Molecular and Cellular Biology, 33(19):3728-3734 (2013).
Kyriakis, J. M. & Avruch, J., "Mammalian Mitogen-Activated Protein Kinase Signal Transduction Pathways Activated by Stress and Inflammation," Physiological Review, 81(2):807-869 (2001).
Lemmers, R. J. F., et al., "Digenic Inheritance of an SMCHDJ Mutation and an FSHD-Permissive D4Z4 Allele Causes Facioscapulohumeral Muscular Dystrophy Type 2" Nat Genet 2012, 44, 1370 1376.
Lemmers, R. J. L. F., et al., "A Unifying Genetic Model for Facioscapulohumeral Muscular Dystrophy" Science 2010, 329, 1650-1653.

(56) References Cited

OTHER PUBLICATIONS

Mamchaoui, K. et al., "Immortalized pathological human myoblasts: towards a universal tool for the study of neuromuscular disorders," Skeletal Muscle, 1:34 (2011), 11 pages; Retrieved from http://www.skeletalmusclejournal.com/contenl/1/1/31.
Martin, E. D. et al., "p38 MAPK in cardioprotection—are we there yet?," British Journal of Pharmacology, 172:2101-2113 (2015).
Masson, D., et al., "Increased HDL Cholesterol and ApoA-I in Humans and Mice Treated With a Novel SR-BI Inhibitor" Arterioscler Thromb Vase Biol 2009, 29, 2054-2060.
Perdiguero, E. et al., "Genetic analysis of p38 MAP kinases in myogenesis: fundamental role of p38a in abrogating myoblast proliferation," The EMBO Journal, 26(5):1245-1256 (2007).
Rautio, J. et al., "Prodrugs: design and clinical applications," Nature Reviews of Drug Discovery, 7:255- 270 (2008).
Rickard, A. M. et al., "Endogenous DUX4 expression in FSHD myotubes is sufficient to cause cell death and disrupts RNA splicing and cell migration pathways," Human Molecular Genetics, 24(20):5901-5914 (2015).
Sakellariou, P. et al., "Neuromuscular electrical stimulation promotes development in mice of mature human muscle from immortalized human myoblasts," Skeletal Muscle, 6:4 (2016), 14 pages; doi: 10.1186/s13395-016-0078-6.
Shadle, S. C. et al., "DUX4-induced dsRNA and MYC mRNA stabilization activate apoptotic pathways in human cell models of Facioscapulohumeral dystrophy," PLoS Genetics (2017), 25 pages; Retrieved from https://doi.org/10.1371/oumal.oaen.1006658.
Statland, J.M. & Tawil, R., "Facioscapulohumeral Muscular Dystrophy," Neural Clin., 32(3):721-ix (2014), 10 pages; doi: 10.1016/j.ncl.2014.04.003.
Tawil, R. et al., "Facioscapulohumeral dystrophy: the path to consensus on pathophysiology," Skeletal Muscle, 4:12 (2014), 15 pages; doi:10.1186/2044-5040-4-12.
Third party observations in European Patent Application 18792812.2. Filed on Mar. 30, 2021.
Third party observations in European Patent Application 18797227.8. Filed on Mar. 12, 2021.
Thorley, M. et al., "Skeletal muscle characteristics are preserved in hTERT/cdk4 human myogenic cell lines," Skeletal Muscle, 6:43 (2016), 12 pages; doi: 10.1186/s13395-016-0115-5.
Van Der Maarel, S. M. et al., "Facioscapulohumeral muscular dystrophy," Biochimica et Biophysica Acta, 1772:186-194 (2007).
Viemann, D. et al., "Transcriptional profiling of IKK2/NF-κB- and p38 MAPkinase-dependent gene expression in TNF-α-stimulated primary human endothelial cells," Blood, 103(9):3365-3373 (2004).
Wahl, G. M. et al., "Molecular Hybridization of Immobilized Nucleic Acids: Theoretical Concepts and Practical Considerations," Methods in Enzymology, 152:399-407 (1987).
Wallace, L. M. et al., "DUX4, a Candidate Gene for Facioscapulohumeral Muscular Dystrophy, Causes p53-Dependent Myopathy In Vivo," Ann Neural, 69(3):540-552 (2011).
Welsh, S. et al., "Antitumor activity and pharmacodynamic properties of PX-478, an inhibitor of hypoxia-inducible factor-1a," Molecular Cancer Therapeutics, 3(3):233 244 (2004).
Whitmarsh, A. J., "A central role for p38 MAPK in the early transcriptional response to stress," BMC Biology, 8:47 (2010), 3 pages; doi: 10.1186/17 41-7007-8-47.
Wissing, E. R. et al., "P38a MAPK underlies muscular dystrophy and myofiber death through a Bax-dependent mechanism," Human Molecular Genetics, 23(20):5452-5463 (2014).
Yang, T., et al., "Functional Roles of p38 Mitogen-Activated Protein Kinase in Macrophage-Mediated Inflammatory Responses" Mediat Injlamm 2014, Article ID 352371, 13 pages.
Yao, Z. et al., "DUX4-induced gene expression is the major molecular signature in FSHD skeletal muscle," Human Molecular Genetics, 23(20):5342-5352 (2014).
Yong, H.-Y. et al.,"The p38 MAPK inhibitors for the treatment of inflammatory diseases and cancer," Expert Opin Investig Drugs, 18(12):1893-1905 (2009).

Zarubin, T. & Han, J., "Activation and signaling of the p38 MAP kinase pathway," Cell Research, 15(1):11-18 (2005).
Zhang, Y. et al., "Comparison of non-canonical PAMs for CRISPR/Cas9-mediated DNA cleavage in human cells," Scientific Reports, 4:5405 (2005), 5 pages; doi: 10.1038/srep05405.
U.S. Appl. No. 16/166,031, filed Oct. 19, 2018, U.S. Pat. No. 10,342,786.
U.S. Appl. No. 16/195,361, filed Nov. 19, 2018, U.S. Pat. No. 10,537,560.
U.S. Appl. No. 16/748,217, filed Jan. 21, 2020, US 2020-0383963 A1.
Down et al., "The discovery and initial optimisation of pyrrole-2-carboxamides as inhibitors of p38a MAP kinase," Bioorganic & Medicinal Chemistry letters 20:3936-3940 (2010).
Kong et al. (2013) "Recent Developments of p38α MAP Kinase Inhibitors as Antiinflammatory Agents Based on the Imidazole Scaffolds," Curr Med Chem. 20(15):1997-2016. doi: 10.2174/09298673 11320150006.
Ariey-Bonnet, J et al., In silico molecular target prediction unveils mebendazole as a potent MAPK14 inhibitor. Mol Oncol (Sep. 2020).†
Pi, R. et al., Minocycline prevents glutamate-induced apoptosis of cerebellar granule neurons by differential regulation of p38 and Akt pathways. J Neurochem, vol. 91, Issue No. 5, pp. 1219-1230 (Dec. 2004).†
Hammaker, D. et al., "Go upstream, young man": lessons learned from the p38 saga. Ann Rheum Dis, vol. 69, Issue No. Suppl. 1, pp. i77-i82 (Jan. 2010).†
Barbour, A.M. et al., Safety, tolerability, pharmacokinetics and pharmacodynamics of losmapimod following a single intravenous or oral does in healthy volunteers. BR J Clin Pharmacol, vol. 76, Issue No. 1, pp. 99-106 (Jul. 2013).†
Campbell, A.E. et al., BET bromodomain inhibitors and agonists of the beta-2 adrenergic receptor identified in screens for compounds that inhibit DUX4 expression in FSHD muscle cells. Skelet Muscle, vol. 7, Issue No. 1, p. 16 (Sep. 2017).†
Keränen, T. et al., Anti-Inflammtory Effects of beta-2-recepter agonists salbutamol and terbutaline are mediated by MKP-1. PLoS One, vol. 11, Issue No. 2, p. e0148144 (Feb. 2016).†
Ariey-Bonnet, J. et al., in silico molecular target prediction unveils mebendazole as a potent MAPK14 inhibitor. Mol. Oncol., vol. 14, Issue No. 12, pp. 3083-3099 (Dec. 2020).†
Ozbek, E. et al., Atorvastatin prevents gentamicin-induced renal damage in rats through the inhibition of p38-MAPK and NF-kB pathways. Renal Failure, vol. 31, Issue No. 5, pp. 382-392 (2009).†
McElroy, P.B. et al., Post-translational activation of glutamate cysteine ligase with dimercaprol: a novel mechanism of inhibiting neuroinflammation in vitro. J Bio. Chem, vol. 292, Issue No. 13, pp. 5532-5545 (Mar. 2017).†
Ferreira Lima, G. et al., Inosine, an endogenous purine nucleoside, avoids early stages of atherosclerosis development associated to eNOS activation and p38 MAPK/NF-kB inhibition in rats. Eur J Pharmacol, vol. 882, p. 173289 (Sep. 2020).†
Ali, N. et al., Ebselen inhibits p38 mitogen-activated protein kinase-mediated endothelial cell death by hydrogen peroxide. Eur J Pharmacol, VI. 485, Issue No. 1-3, pp. 127-135 (Feb. 2004).†
Stone, A.A. et al., Microtubule inhibitors elicit differential effects on MAP kinase (JNK, ERK, and p38) signaling pathways in human KB-3 carcinoma cells. Exp Cell Res, vol. 254, Issue No. 1, pp. 110-119 (Jan. 2000).†
Hammaker D. et al., "Go upstream, you man": lessons learned from the p38 saga. Ann Rheum Dis, vol. 69, Issue No. Suppl 1, pp. i77-i82 (Jan. 2010).†
Barbour, A. M. et al., Safety, tolerability, pharmacokinetics and pharmacodynamics of losmapimod following single intravenous or oral dose in healthy volunteers. BR J Clin Pharmacol, vol. 76, Issue No. 1, pp. 99-106 (Dec. 2012).†
Ozbek, E. et al., Atorvastatin Prevents Gentamicin-Induced Renal Damage in Rats through the Inhibition of p38-MAPK and NF-kB Pathways. Renal Failure, vol. 31, pp. 382-392 (2009).†
Keränen, T. et al., Anti-Inflammatory Effects of β2-Receptor Agonists Salbutamol and Terbutaline are Mediated by MKP-1. PLoS One, vol. 11, Issue No. 2, p. e0148144 (Feb. 2016).†

(56) References Cited

OTHER PUBLICATIONS

Ali, N. et al., Ebselen inhibits p38 mitogen-activated protein kinase-mediated endothelial cell death by hydrogen peroxide. Eur J Pharmacol, vol. 485, Issue vol. 1-3, pp. 127-135 (Feb. 2004).†

\* cited by examiner
† cited by third party

FIG. 6C
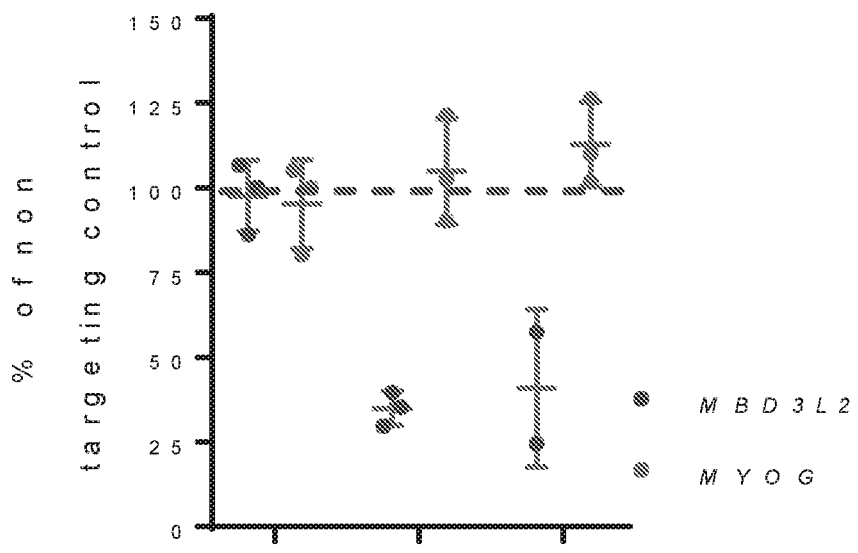
FIG. 7
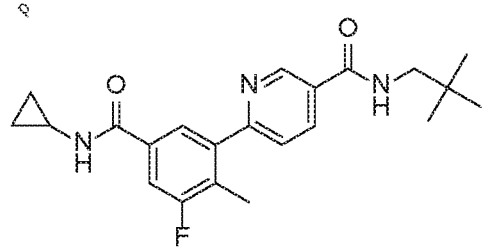
FTX-1821
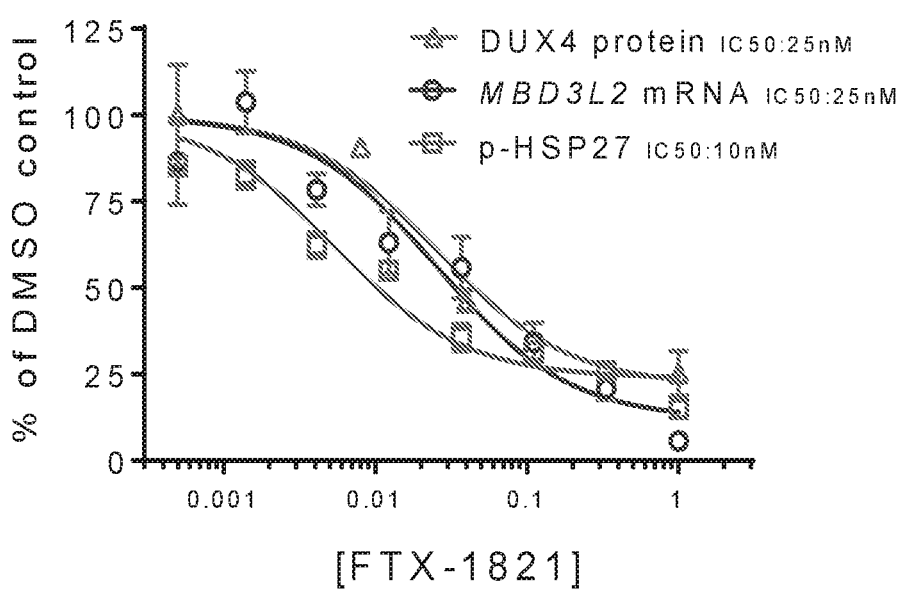

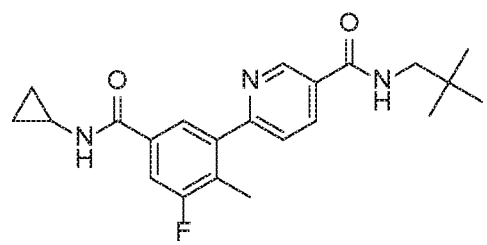
FTX-1821
Quantification of nuclei in MHC+ myotubes after FTX-1821
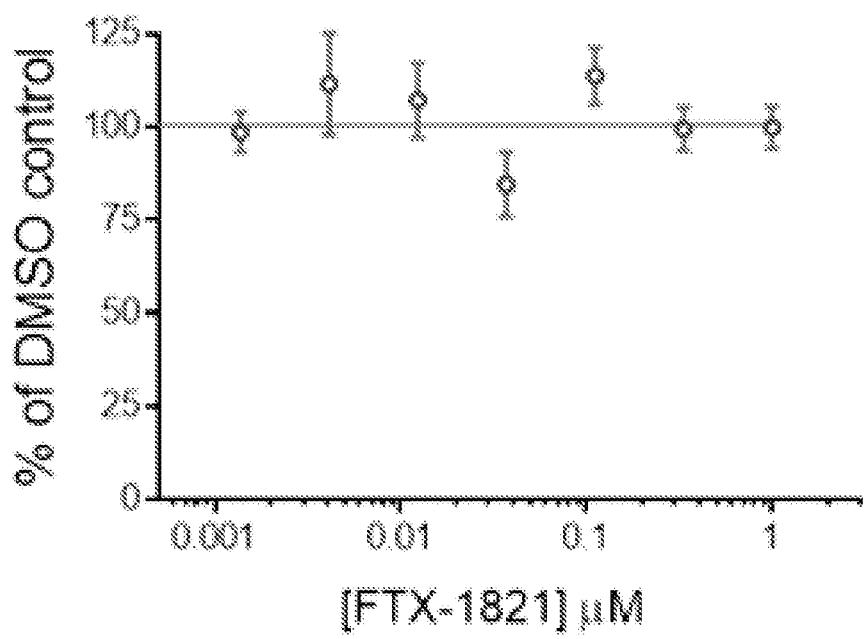
FIG. 8B

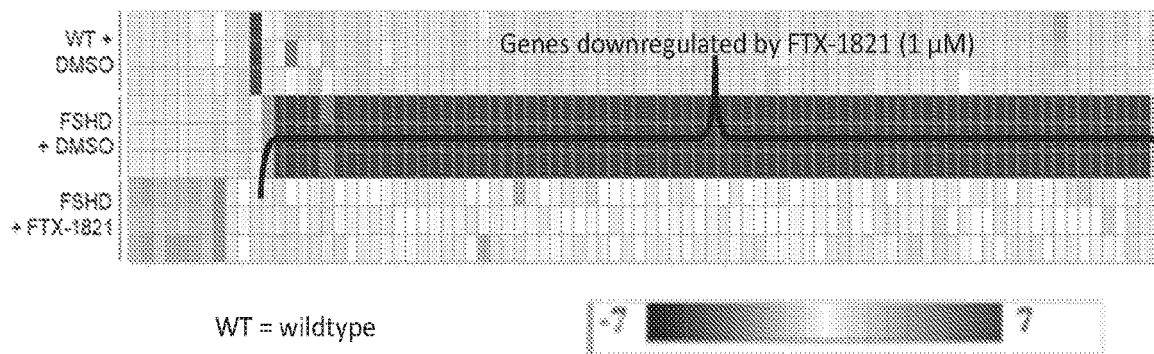

Genes downregulated by FTX-1821:

| | | | | | |
|---|---|---|---|---|---|
| ZSCAN4 | TRIM51BP | MBD3L3 | UBTFL5 | AP001043.1 | ABRA |
| PRAMEF20 | KHDC1P1 | KDM4F | HNRNPCL3 | MBD3L5 | WIPF3 |
| PRAMEF6 | RFPL4A | DUXA | ZIM3 | TRIM51CP | UBTFL1 |
| PRAMEF17 | ZSCAN5DP | TPRX1 | TRIM53BP | TRIM53CP | POU5F1B |
| PRAMEF1 | PRAMEF9 | PRAMEF13 | TRIM53AP | CILP | UBTFL2 |
| ZNF705E | KLF17 | TRIM43 | DPPA3 | SLC2A3 | FAM151A |
| LEUTX | RFPL2 | MBD3L2 | MBD3L2B | TRIM49 | TRIM60 |
| PRAMEF15 | CCNA1 | PRAMEF11 | USP29 | ZNF705G | PRAMEF28P |
| ZNF705A | PRAMEF2 | PRAMEF14 | ZNF296 | TRIM43CP | KLF18 |
| PRAMEF12 | HNRNPCL1 | KHDC1L | F2RL1 | TRIM48 | SNAI1P1 |
| SLC34A2 | DUXB | PRAMEF19 | FREM2 | UBTFL6 | HUNK |
| HNRNPCL2 | HSPA6 | PRAMEF4 | PRAMEF8 | PRAMEF33 | P2RX1 |
| PRAMEF18 | TRIM43B | KDM4E | TRIM51 | C1DP2 | TPRX2P |
| TRIM49C | TC2N | TRIM49B | IGFN1 | DPYSL5 | FAM9C |
| | | | | | GJA5 |
| | | | | | IMPG2 |

FIG. 10A

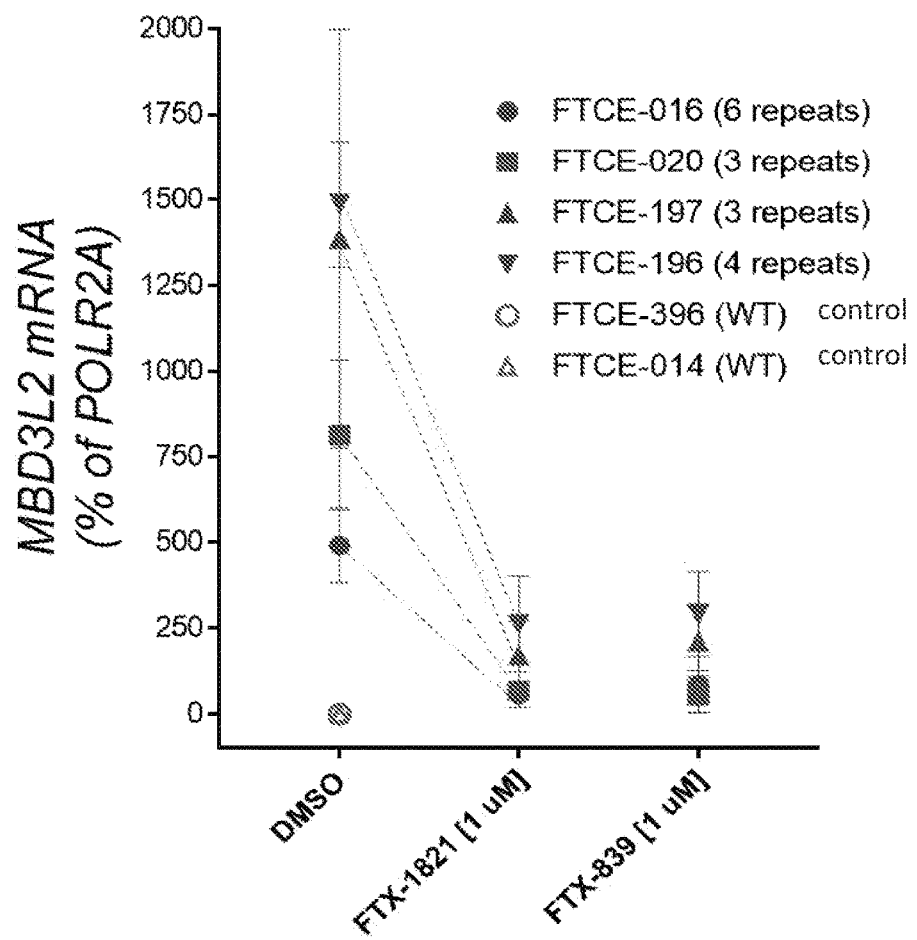
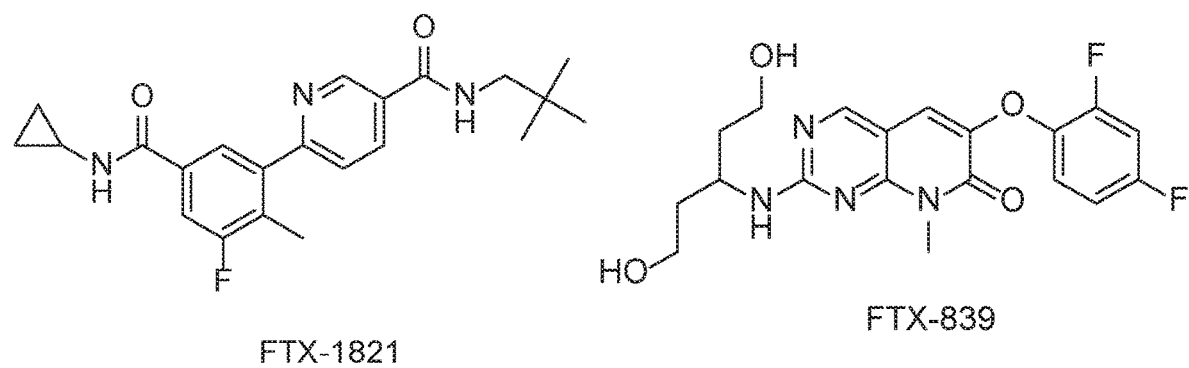
FIG. 11

Table 1.

| DRUG_NAME | Formatted ID | IC50 *MBD3L2* (nM) |
|---|---|---|
| TAK-715 | FTX000500 | 48 |
| VX-702 | FTX000638 | 41 |
| R1487 | FTX000830 | 6 |
| Pamapimod | FTX000839 | 10 |
| AS1940477 | FTX001341 | 20 |
| Losmapimod | FTX001821 | 30 |
| LY2228820 | FTX002865 | 10 |
| SCIO-469 | FTX004078 | 25 |
| Doramapimod | FTX004385 | 42 |
| BMS-582949 | FTX005041 | 68 |
| PH-797804 | FTX005042 | 10 |
| Pexmetinib | FTX005043 | 5 |

FIG. 12A

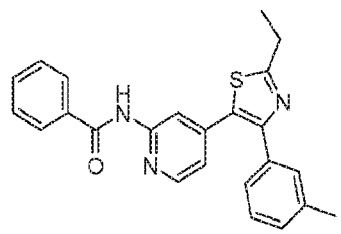
FTX-500
"TAK-715"
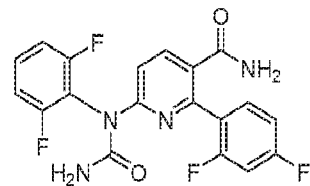
FTX-638
"VX-702"
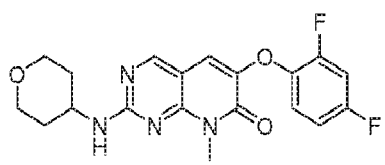
FTX-830
"R1487"
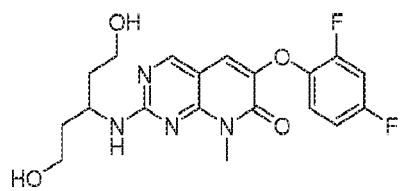
FTX-839
"Pamapimod"
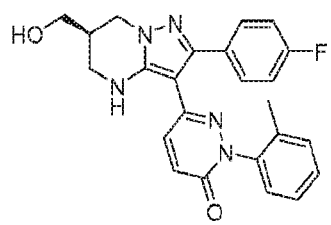
FTX-1341
"AS1940477"
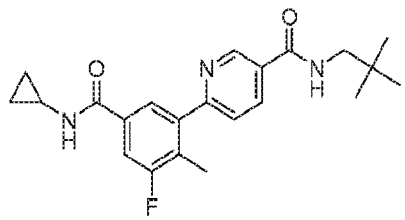
FTX-1821
"Losmapimod"
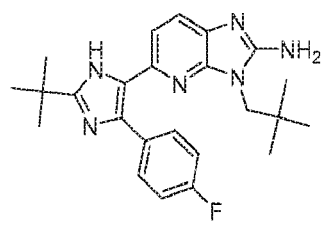
FTX-2865
"LY2228820"
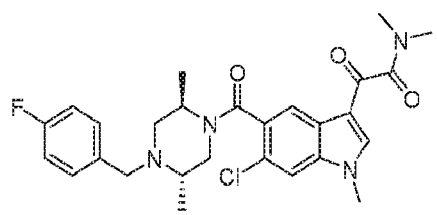
FTX-4078
"SCIO-469"
FIG. 12B

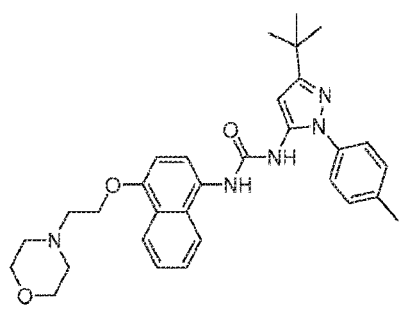
FTX-4385
"Doramapimod"
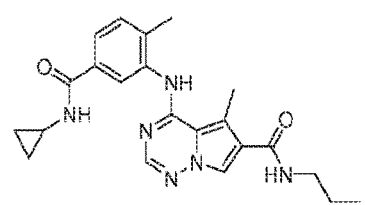
FTX-5041
"BMS-582949"
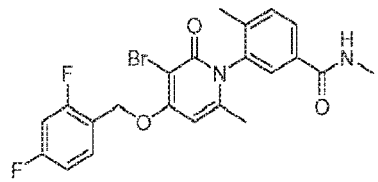
FTX-5042
"PH-797804"
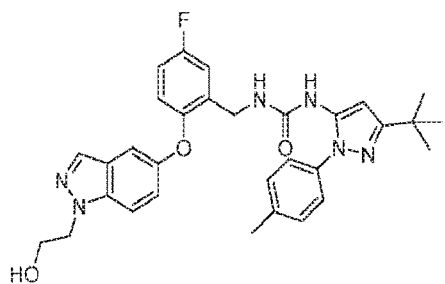
FTX-5043
"Pexmetinib"
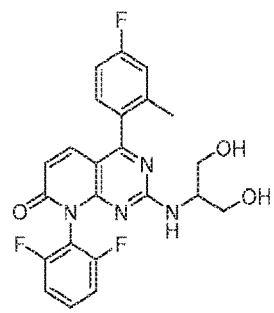
"Dilmapimod"
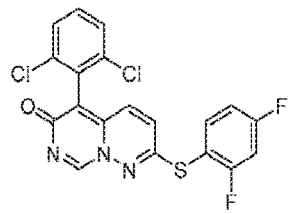
FTX-4384
"Neflamapimod"
"VX-745"
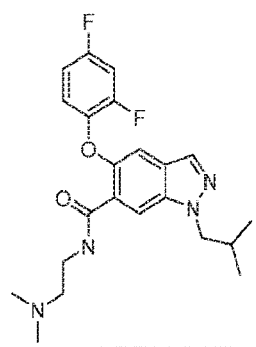
"ARRY-797"
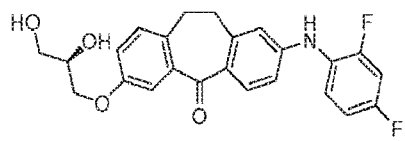
"Skepinone-L"
FIG. 12B (cont.)

Table 2.

| CTID # | ID | p/i | Cell type | Repeat # | Cntrl/FSHD |
|---|---|---|---|---|---|
| CTID-001 | FTCE-204 | primary | Fibroblast | 39 | Control |
| CTID-002 | FTCE-425 | primary | Myoblast | 5.5 | FSHD |
| CTID-003 | FTCE-423 | primary | Myoblast | 3 | FSHD |
| CTID-004 | FTCE-396 | primary | Myoblast | n/a | Control |
| CTID-005 | FTCE-422 | primary | Myoblast | 2 | FSHD |
| CTID-006 | FTCE-424 | primary | Myoblast | 4.5 | FSHD |
| CTID-007 | FTCE-426 | primary | Myoblast | 4.5 | FSHD |
| CTID-008 | FTCE-428 | primary | Myoblast | SMCHD1 | FSHD2 |
| CTID-009 | FTCE-197 | primary | Myoblast | 2 | FSHD |
| CTID-010 | FTCE-196 | primary | Myoblast | 3 | FSHD |
| CTID-011 | FTCE-429 | primary | Myoblast | SMCHD1 | FSHD2 |
| CTID-012 | FTCE-421 | primary | Myoblast | 7 | FSHD |
| CTID-013 | FTCE-205 | primary | Myoblast | 12 | Control |
| CTID-014 | FTCE-427 | primary | Myoblast | SMCHD1 | FSHD2 |
| CTID-015 | FTCE-16 | immortalized | Myoblast | 6.5 | FSHD |
| C6 Control | FTCE-20 | immortalized | Myoblast | 3 | FSHD |
| WT Control | FTCE-14 | immortalized | Myoblast | n/a | Control |
| A4 Control | FTCE-18 | immortalized | Myoblast | n/a | Control |

FIG. 13

Treatment of FSHD mice with the potent and selective p38 inhibitor, FTX-2865, produces p38 target engagement in the trapezius muscles

USE OF P38 INHIBITORS TO REDUCE EXPRESSION OF DUX4

CROSS REFERENCE TO RELATED APPLICATIONS

This application is a U.S. National Phase Application, filed under 35 U.S.C. 371, of International Application No. PCT/US2018/054638, filed on Oct. 5, 2018, which claims priority to U.S. Provisional Application No. 62/568,673, filed on Oct. 5, 2017; U.S. Provisional Application No. 62/568,754, filed on Oct. 5, 2017; U.S. Provisional Application No. 62/682,563, filed on Jun. 8, 2018; and U.S. Provisional Application No. 62/682,565, filed on Jun. 8, 2018; all of which are incorporated by reference herein in their entireties.

SEQUENCE LISTING

The instant application contains a Sequence Listing that has been submitted electronically in ASCII format and is hereby incorporated by reference in its entirety. Said ASCII copy, created on Oct. 4, 2018, is named FULC_027_02WO_ST25.txt and is 27 KB in size.

FIELD OF THE DISCLOSURE

The present invention relates to compositions and methods of inhibiting p38 kinase to reduce gene and protein expression of DUX4 and downstream genes regulated by DUX4. The present invention further relates to methods for treating subjects with disease and disorders associated with increased expression of DUX4 or expression of an aberrant form of DUX4, such as Facioscapulohumeral muscular dystrophy (FSHD).

BACKGROUND

The muscular dystrophies (MD) are a group of more than 30 different genetic diseases characterized by progressive weakness and degeneration of the skeletal muscles that control movement. Some forms of MD occur in infancy or childhood, while others may not appear until middle age or older. The various MD diseases differ in terms of the distribution and extent of muscle weakness (some forms of MD also affect cardiac muscle), age of onset, rate of progression, and pattern of inheritance.

Facioscapulohumeral muscular dystrophy (FSHD) is the third most common form of muscular dystrophy and affects approximately 1 in 15,000 people worldwide. FSHD is caused by genetic mutations resulting in the epigenetic derepression of the DUX4 gene, which makes this disease unique among muscular dystrophies. FSHD's primary manifestations are weakness and wasting of muscles of the face, shoulder girdle, upper arms, and trunk, and impacts lower extremities in more severe cases.

Genetic mutations associated with FSHD lead to a partial decompaction of the D4Z4 chromatin structure and a resulting failure to repress DUX4, a transcription factor encoded by the D4Z4 unit, in skeletal muscle. FSHD1, representing about 95% of FSHD cases reported, is associated with deletions of macrosatellite D4Z4 repeats in the subtelomeric region of chromosome 4q35, leaving 1-10 D4Z4 repeats (reviewed in Tawil et. al., 2014). FSHD2 is caused by mutations in Structural Maintenance of Chromosomes Flexible Hinge Domain Containing 1 gene (SMCHD1) on chromosome 18 (reviewed in van der Maarel et. al., 2007). Both FSHD1 and FSHD2 mutations lead to loss of repression at the 4q35 D4Z4 repeat array, allowing aberrant transcription in muscle of a full-length form of Double homeobox 4, DUX4, mRNA (DUX4-fl), which encodes the double homeobox 4 (DUX4) transcription factor (Tawil et. al., 2014). DUX4-fl RNA isoforms found associated with FSHD vary only in the 3' untranslated region and have no identified functional distinction.

There is currently no approved treatment that can halt or reverse the effects of FSHD, although nonsteroidal anti-inflammatory drug are often prescribed to improve comfort and mobility. Clearly, therefore, there is a need in the art for new methods for reducing the expression levels of DUX4, e.g., DUX4-fl mRNA and/or DUX4 protein, e.g., to treat FSHD and other diseases. The present invention meets this need.

BRIEF DESCRIPTION OF THE DRAWINGS

FIG. 1A includes micrographs of FSHD myotubes stained using an antibody that binds DUX4 protein and/or 4',6-diamidino-2-phenylindole (DAPI; to detect nuclei). Mature FSHD myotubes showed actin striations in culture (not shown) and expressed DUX4 protein in discrete sets of nuclei contained within a differentiated myotube (FIG. 1A). FIG. 1B is a graph showing relative expression of DUX4 mRNA in FSHD myotubes and myotubes from an isogenic wild type (healthy) control.

FIG. 3A is a graph showing grouped plate quality control data comparing MBD3L2 expression in FSHD myotubes treated with DMSO control or 1 µM DUX4-targeted ASOs, and healthy normal isogenic wild-type myotubes (WT). FIG. 3B is a graph showing dose-dependent reduction of MBD3L2 mRNA expression in FSHD myotubes treated with different dilutions of the DUX4-targeted ASO (FTX-2). FIG. 3C shows plate-based assay statistics comparing MBD3L2 signal in FSHD myotubes treated with DMSO to DUX4-targeted ASOs or wild-type myotubes treated with DMSO.

FIG. 5A is a graph showing that dose-dependent reduction in DUX4 fl mRNA (filled circles) and MBD3L2 mRNA (open circles). FIG. 5B shows micrographs of FSHD myotubes treated with either DMSO or Pamapimod.

FIGS. 6A-6C are graphs showing mRNA levels of MAPK14 (FIG. 6A) and MBD3L2 (FIG. 6B and FIG. 6C) in FSHD myotubes treated with siRNAs targeting p38a MAPK14 (siMAPK14 85 and siMAPK14 86; FIG. 6A and FIG. 6B) or treated with p38a kinase (MAPK14 and DUX4 pLAM) Cas9/sgRNA RNPs (FIG. 6C), as compared to non-targeting control (NT CTRL). In FIG. 6C, for each treatment, the results shown left to right correspond to MBD3L2 and MYOG, respectively.

FIG. 7 is a graph showing expression levels of DUX4 protein, MBD3L2 mRNA, and p-HSP27 protein in FSHD myotubes following treatment with increasing dosages of FTX-1821 (structure shown), as a percentage of DMSO control treatment levels. Bars represent standard deviation.

FIGS. 8A and 8B show the effect of FTX-1821 on myotube formation. FIG. 8A provides representative images of morphology of immortalized FSHD myotubes obtained after treatment with vehicle (DMSO) or the indicated concentrations of FTX-1821, and staining with antibodies against MHC and DAPI (nuclear stain). FIG. 8B is a graph showing quantification of nuclei in myotubes, as defined by MHC staining, after treatment with FTX-1821 at concentrations tested. Bars represent standard deviation of three replicates.

FIG. 9A provides micrographs of FSHD myotubes stained for active caspase-3 (as a marker of apoptosis) or DAPI. Apoptosis was detected in a sporadic manner in a subset of myotubes in culture as shown by white circles in the left panel and in the magnified region to the right. FIG. 9B is a graph showing quantification of active caspase-3 signal in FSHD myotubes treated with the indicated concentrations of FTX 1821.

FIGS. 10A and 10B illustrate the identification of genes downregulated in FSHD myotubes by FTX-1821. FIG. 10A is a heatmap, which illustrates differentially expressed genes identified by RNA-seq profiling. Three replicates for each condition were analyzed by RNA-seq and genes were clustered by the direction and intensity of change as indicated. The color bar indicates the normalized changes observed, e.g., genes that were downregulated by FTX-1821 are enriched in samples treated with only DMSO. Down-regulated genes are listed in FIG. 10A. FIG. 10B is a graph showing the normalized expression level reads of the DUX4 target genes that were downregulated upon treatment with FTX-1821 in wild type cells treated with vehicle control DMSO, FSHD cells treated with DMSO, or FSHD cells treated with FTX-1821.

FIG. 11 is a graph showing mRNA expression levels by qRT-PCR of the DUX4 target gene, MBD3L2 (normalized to POLR2A), in myotubes derived from four distinct FSHD patient myoblast lines, FTCE-016, -020, -197, -196 and two wild type (WT) control lines, following the indicated treatment with DMSO vehicle control, FTX-1821 or FTX-839.

FIGS. 12A and 12B provide information on various p38 inhibitors. FIG. 12A is a table of data summarizing pharmacology for the indicated p38α and β inhibitors, including IC50 for reducing MBD3L2 expression in FSHD cells. Comparable MBD3L2 $IC_{50}$ values are shown, indicating inhibition of DUX4 downstream gene expression in FSHD myotubes across a broad structural panel of p38α and β inhibitors reported to have similar enzyme potencies. These data indicate that p38 inhibition result in DUX4 target gene, MBD3L2, reduction $IC_{50}$ values in the range of ~6-68 nM. FIG. 12B provides the compound structures of the p38 inhibitors listed in FIG. 12A.

FIG. 13 is a table of various cell lines utilized in "clinical trial in a dish," which shows diversity of genotypes, and includes both primary and immortalized lines, as well as FSHD1 and FSHD2 patient lines.

SUMMARY OF THE INVENTION

Figure 1A:
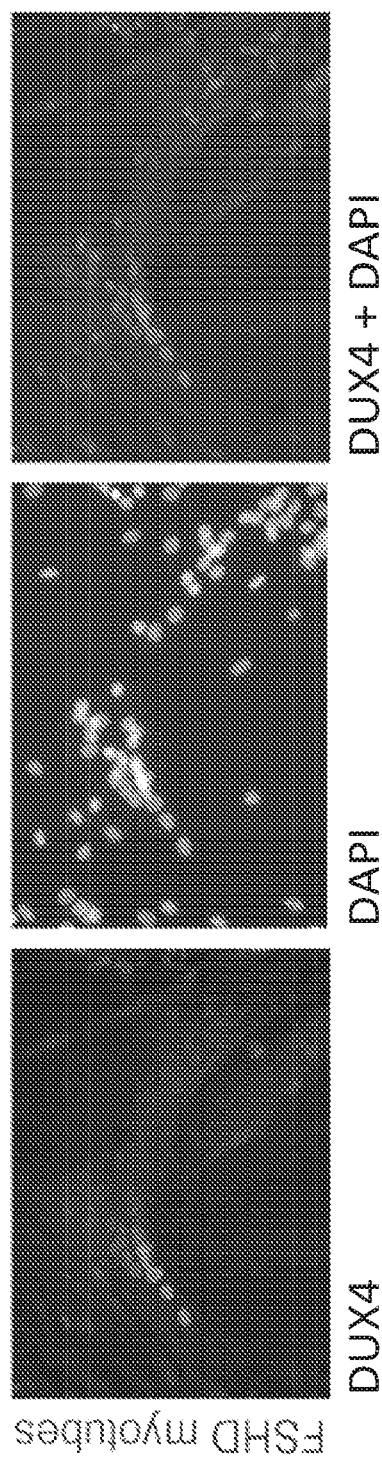
FIGS. 1A and 1B show expression of DUX4 protein and RNA in FSHD myotubes.
Figure 1B:
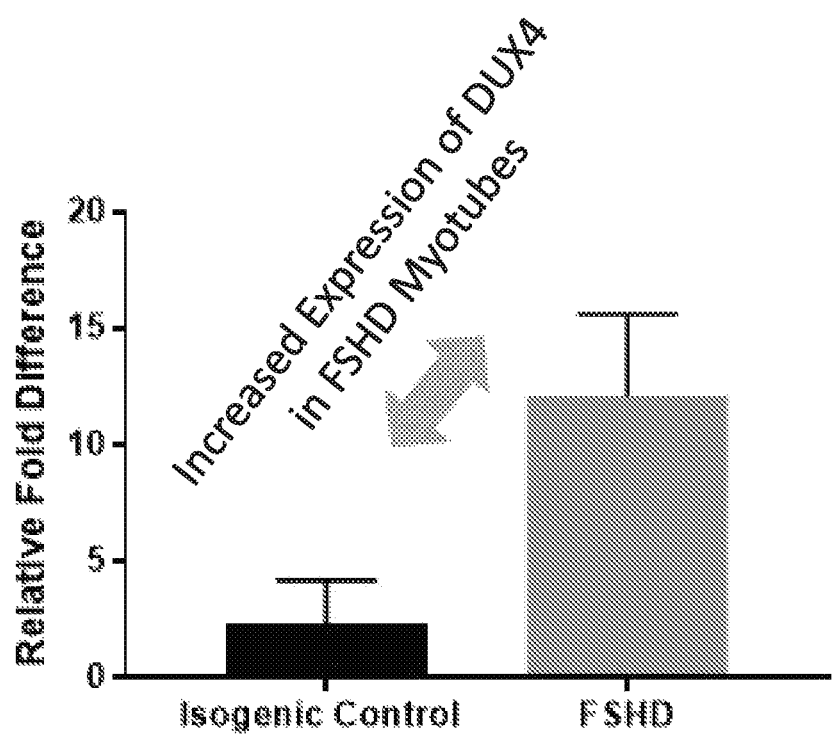

The present disclosure provides methods of reducing the expression a DUX4-fl mRNA, a DUX4 polypeptide, or a polypeptide encoded by a downstream target gene of DUX4, in cells, comprising contacting the cells with an agent that results in a reduction of active p38 protein in the cell, thereby reducing expression the DUX4 polypeptide or the polypeptide encoded by the downstream target gene of DUX4. These methods may be practiced using a variety of different types of agents, and for modulating a variety of different biological processes in the cell, as well as for treating subjects for diseases associated with aberrant DUX4 expression, such as FSHD.

In certain embodiments of any of the methods disclosed herein, the cell is a muscle cell, optionally a terminally differentiated muscle cell. In some embodiments, the cell has an increased expression level of the DUX4-fl mRNA, the DUX4 polypeptide, or the polypeptide encoded by the downstream target gene, as compared to the expression level of the DUX4-fl mRNA, the DUX4 polypeptide, or the polypeptide encoded by the downstream target gene, in a control cell, e.g., a cell obtained from a healthy subject. In some embodiments, the increased expression level of the DUX4-fl mRNA, the DUX4 polypeptide, or the polypeptide encoded by the downstream target gene, is due to reduced repression at a D4Z4 locus in the cell. In certain embodiments, the cell is associated with facioscapulohumeral muscular dystrophy (FSHD), e.g., it was obtained from a subject diagnosed with FSHD or is present within a subject diagnosed with FSHD. In some embodiments, the cell comprises a deletion of one or more macrosatellite D4Z4 repeats in the subtelomeric region of chromosome 4q35, optionally wherein the cell comprises ≤7 macrosatellite D4Z4 repeats in the subtelomeric region of chromosome 4q35. In some embodiments, the cell comprises one or more mutations in a Structural Maintenance Of Chromosomes Flexible Hinge Domain Containing 1 (SMCHD1) gene. In some embodiments, the cell comprises at least one non-deleted 4qA allele.

In certain embodiments of the methods disclosed herein, the agent inhibits the expression or activity, or reduces the amount, of the p38 protein, wherein the activity is optionally kinase activity.

In some embodiments, the agent inhibits the expression of the p38 protein. In particular embodiments, the agent binds a polynucleotide encoding the p38 protein, or binds an antisense polynucleotide thereof. In particular embodiments, the agent comprises or consists of a nucleic acid, optionally a DNA, RNA, gRNA, shRNA, siRNA, or antisense oligonucleotide.

In some embodiments, the agent inhibits the activity of the p38 protein. In particular embodiments, the agent binds the p38 protein. In particular embodiments, the agent comprises or consists of a polypeptide, optionally a protein, a peptide, a protein mimetic, a peptidomimetic, or an antibody or functional fragment thereof. In some embodiments, the agent comprises a small molecule, optionally a small organic molecule or a small inorganic molecule.

In certain embodiments of any of the methods disclosed herein, the downstream target gene is RFPL2, CCNA1, SLC34A2, TPRX1, KHDC1L, ZSCAN4, PRAMEF20, TRIM49, PRAMEF4, PRAME6, PRAMEF15 or ZNF280A.

In particular embodiments of any of the methods disclosed herein, the expression or the activity of the p38 protein, or the amount of the p38 protein, is reduced by at least 10%, at least 20%, at least 30%, at least 40%, at least 50%, at least 60%, at least 70%, at least 80%, at least 90%, at least 95%, at least 98%, at least 99%, or 100%.

In a related embodiment, the present disclosure provides a method of treating or preventing a disease or disorder associated with increased expression of a DUX4-fl mRNA, a DUX4 protein, or a polypeptide encoded by a downstream target gene of DUX4, in a subject in need thereof, comprising providing to the subject a pharmaceutical composition comprising an agent that results in a reduction in the amount of active p38 protein in one or more tissue of the subject, thereby reducing expression of the DUX4-fl mRNA, the DUX4 protein, or the polypeptide encoding the downstream target gene in one or more tissue of the subject. In some embodiments, the disease or disorder is a facioscapulohumeral muscular dystrophy (FSHD), optionally FSHD1 or FSHD2. In certain embodiments, the subject comprises reduced repression at a D4Z4 locus. In some embodiments, the subject comprises a deletion of one or more macrosatellite D4Z4 repeats in the subtelomeric region of chromosome 4q35, optionally wherein the cell comprises ≤7 macrosatellite D4Z4 repeats in the subtelomeric region of chromosome 4q35. In some embodiments, the subject comprises one or more mutations in a Structural Maintenance Of Chromosomes Flexible Hinge Domain Containing 1 (SMCHD1) gene. In some embodiments, the subject comprises at least one non-deleted 4qA allele. In certain embodiments, the expression or the activity of, or the amount of, the p38 protein is reduced by at least 10%, at least 20%, at least 30%, at least 40%, at least 50%, at least 60%, at least 70%, at least 80%, at least 90%, at least 95%, at least 98%, at least 99%, or 100% in a muscle tissue of the subject. In some embodiments, the method decreases muscle degeneration in the subject. In some embodiments, the method reduces apoptosis of muscle cells in the subject. In some embodiments, the muscle tissue is terminally differentiated. In particular embodiments, the pharmaceutical composition is provided to the subject parenterally or orally. In certain embodiments, the pharmaceutical composition is provided to a muscle tissue of the subject, optionally parenterally or intramuscularly. In particular embodiments, the method further comprises providing to the subject a second agent or therapy for treating the disease or disorder associated with increased expression of a DUX4 protein, or a polypeptide encoded by a downstream target gene of DUX4.

The present disclosure also provides a unit dosage form of a pharmaceutical composition comprising an agent that results in a reduction in the amount of active p38 protein in a cell, and a pharmaceutically acceptable carrier, diluent or excipient, wherein the unit dosage form is effective to reduce expression or activity of a DUX4-fl mRNA, a DUX4 polypeptide, or a polypeptide encoded by a downstream target gene of DUX4, in one or more cell or tissue in a subject to whom the unit dosage form is administered. In particular embodiments, the agent binds the DUX4 polypeptide or binds a polynucleotide encoding the DUX4 polypeptide. In some embodiments, the agent comprises or consists of a nucleic acid, optionally a DNA, RNA, gRNA, shRNA, siRNA, or antisense oligonucleotide. In some embodiments, the agent comprises or consists of a polypeptide, optionally a protein, a peptide, a protein mimetic, a peptidomimetic, or an antibody or functional fragment thereof. In some embodiments, the agent comprises a small molecule, optionally an organic molecule or an inorganic molecule. In certain embodiments, the tissue is muscle tissue, optionally wherein the tissue comprises cells comprising a mutation associated with facioscapulohumeral muscular dystrophy (FSHD).

In a further related embodiment, the present disclosure provides a method of reducing apoptosis of a cell, e.g., a muscle cell, comprising contacting the cell with an agent that results in a reduction in the amount of active p38 protein in the cell, optionally wherein the muscle cell is terminally differentiated, thereby reducing expression of a DUX4-fl mRNA, a DUX4 protein, or a polypeptide encoded by a downstream target gene of DUX4, in the cell. In some embodiments, the cell has an increased expression level of the DUX4-fl mRNA, the DUX4 polypeptide, or the polypeptide encoded by the downstream target gene, as compared to the expression level of the DUX4 polypeptide, or the polypeptide encoded by the downstream target gene, in a control cell. In some embodiments, the increased expression level of the DUX4-fl mRNA, the DUX4 polypeptide, or the polypeptide encoded by the downstream target gene, is due to reduced repression at a D4Z4 locus in the cell. In particular embodiments, the cell comprises one or more mutations associated with FSHD. In certain embodiments, the agent inhibits the expression of the p38 protein, optionally wherein the agent binds a polynucleotide encoding the p38 protein, or an antisense polynucleotide thereof. For instance, in some embodiments, the agent comprises or consists of a nucleic acid, optionally a DNA, RNA, shRNA, siRNA, or antisense oligonucleotide, e.g., which targets p38. In some embodiments, the agent inhibits the activity of the p38 protein, optionally wherein the agent binds the p38 protein. In some embodiments, the agent comprises or consists of a polypeptide, optionally a protein, a peptide, a protein mimetic, a peptidomimetic, or an antibody or functional fragment thereof. In some embodiments, the agent comprises a small molecule, optionally a small organic molecule or a small inorganic molecule. In particular embodiments, the expression or the activity of the p38 protein, the DUX4 protein, or the polypeptide encoded by the DUX4 downstream gene is reduced by at least 10%, at least 20%, at least 30%, at least 40%, at least 50%, at least 60%, at least 70%, at least 80%, at least 90%, at least 95%, at least 98%, at least 99%, or 100%. In particular embodiments, the method reduces apoptosis of muscle cells in a muscle tissue at least 10%, at least 20%, at least 30%, at least 40%, at least 50%, at least 60%, at least 70%, at least 80%, at least 90%, at least 95%, at least 98%, at least 99%, or 100% as compared to a control, e.g., an untreated cell.

In certain embodiments of any of the methods disclosed herein, the agent reduces expression of DUX4 or the downstream target gene. In certain embodiments, the agent binds a p38 protein, e.g., p38-α or p38-β, or binds a polynucleotide encoding the p38 protein, e.g., p38-α or p38-β, or an antisense polynucleotide thereof. In particular embodiments, the agent comprises or consists of: a nucleic acid, optionally a DNA, RNA, shRNA, siRNA, CRISPR gRNA, or antisense oligonucleotide. In particular embodiments, the agent comprises or consists of: a polypeptide, optionally a protein, a peptide, a protein mimetic, a peptidomimetic, or an antibody or functional fragment thereof. In particular embodiments, the agent comprises: a small molecule, optionally an organic molecule or an inorganic molecule. In some embodiments, the downstream target gene is RFPL2, CCNA1, SLC34A2, TPRX1, KHDC1L, ZSCAN4, PRAMEF20, TRIM49, PRAMEF4, PRAME6, PRAMEF15 or ZNF280A. In particular embodiments, the downstream target gene is MBD3L2, ZSCAN4, LEUTX, PRAMEF2, TRIM43, or KHDC1L.

In certain embodiments of any of the methods disclosed herein, the agent binds a p38 protein, e.g., p38-α or p38-β, or binds a polynucleotide encoding a p38 protein e.g., p38-α or p38-β. In some embodiments, the agent comprises or consists of: a nucleic acid, optionally a DNA, RNA, shRNA, siRNA, mRNA, CRISPR gRNA, modified mRNA, morpholino, or antisense oligonucleotide. In some embodiments, the mRNA or modified mRNA encodes an antibody or a functional fragment thereof. In some embodiments, the agent comprises or consists of: a polypeptide, optionally a protein, a peptide, a protein mimetic, a peptidomimetic, or an antibody or functional fragment thereof. In some embodiments, the agent comprises or consists of a gene therapy vector, e.g., a viral vector comprising a nucleic acid sequence encoding a polynucleotide or polypeptide inhibitor of p38, e.g., p38-α or p38-β, or other target. In some embodiments, the agent comprises or consists of a small molecule, optionally an organic molecule or an inorganic molecule. In some embodiments, the downstream target is RFPL2, CCNA1, SLC34A2, TPRX1, KHDC1L, ZSCAN4, PRAMEF20, TRIM49, PRAMEF4, PRAME6, PRAMEF15 or ZNF280A. In some embodiments, the downstream target gene is MBD3L2, ZSCAN4, LEUTX, PRAMEF2, TRIM43, or KHDC1L. In some embodiments, the downstream target gene is CCNA1.

DETAILED DESCRIPTION OF THE INVENTION

The present invention is based, in part, on the discovery that inhibition of p38 kinase, e.g., p38-α, results in reduced expression of DUX4 and downstream genes regulated by DUX4. Accordingly, the invention includes methods and compositions related to using an inhibitor of p38, e.g., p38-α, (alone or in combination with another agent) to reduce the expression and/or activity levels of DUX4 and/or any of its downstream target genes, e.g., in the treatment or prevention of diseases associated with aberrant DUX4 expression, such as FSHD, a type of muscular dystrophy. This may be accomplished in a variety of ways, e.g., reducing expression of the DUX4-fl mRNA, reducing expression of the DUX4 protein, inhibiting DUX4 protein activity; CRISPR genome editing, and/or inducing degradation of the DUX4 protein.

The muscular dystrophies are a diverse group of genetic diseases that cause progressive weakness of the body's muscles. Some types of muscular dystrophy will present symptoms in early childhood, while other types will appear in adulthood. Different muscle groups also may be affected depending on the type of muscular dystrophy. See, e.g., Isin Dalkilic and Louis M Kunkel. Nearly 30 genes are known to give rise to various forms of muscular dystrophy, which differ in age of onset, severity, and muscle groups affected. The number of genes identified increases each year, adding to our understanding as well as revealing the overall complexity of the pathogenesis of these diseases.

For example, two common muscular dystrophies—Duchenne Muscular Dystrophy (DMD) and Facioscapulohumeral dystrophy (FSHD)—are considered to be unique diseases with some shared characteristics. Similarities between DMD and FSHD include that both are genetic diseases and symptoms include muscle loss with muscle weakness leading to disability (therefore both DMD and FSHD are grouped in the large category of muscular dystrophies, which means muscle degeneration). However, DMD and FSHD have very different etiology and disease diagnosis (dystrophin loss in DMD vs expression of DUX4-myotoxin in FSHD). For example, in DMD, mutations in the DMD gene (>2000 known) result in dysfunctional or missing dystrophin. In FSHD, the disease is due to overexpression of the DUX4 gene in muscle tissue; it is not due to point mutations in the gene (DUX4 protein is expressed when the number of D4Z4 repeats in the DUX4 gene is between 1 and 8, or when repression is lost at the D4Z4 by mutations in other silencing machinery). Other differences include that only skeletal muscle is involved in FSHD, whereas both skeletal and cardiac muscle are affected in DMD; the diaphragm is involved in DMD but not FSHD; generally there is childhood onset in DMD but adult/adolescent onset in FSHD; and onset with ambulatory involvement in DMD but onset with face and proximal arm/shoulders in FSHD. Another important distinction is that there is response to steroids in DMD but not in FSHD. In addition, the approved treatment for DMD (Exondys-51 in the US; Ataluren in the EU) will not have any effect in FSHD. Finally, only males are affected in DMD while there is equal involvement of both sexes in FSHD.

FSHD also has an unusual pathology, and it is unique among muscular dystrophies in that its development requires both genetic and epigenetic conditions. The genetic condition is the presence of a complete DUX4 gene. The DUX4 gene is a retrogene normally expressed in germ line and early embryonic cells, but it is repressed by D4Z4 repeat-induced silencing in adult tissues (Ehrlich and Lacey, 2012). Each D4Z4 element contains a promoter and the DUX4 ORF, but lacks a polyadenylation signal (PAS), resulting in rapid DUX4 mRNA degradation. In contrast, transcripts initiated in the distal D4Z4 unit on a 4qA permissive allele extend outside of the repeat array and reach a PAS in the flanking pLAM sequence (reviewed in Tawil et al., 2014; Himeda et al., 2015). The resulting poly-A tail stabilizes the DUX4 mRNAs and allows for their translation into a protein that is not normally expressed in healthy muscle and is toxic to skeletal muscle function. Two enhancers, DUX4 myogenic enhancer 1 (DME1) and DME2, which activate DUX4-fl expression in skeletal myocytes, have been described to regulate DUX4-fl expression in FSHD (Himeda et al., 2014).

FSHD1, FSHD2 stages in early development as well as germline formation stages appear to confer a transcriptionally permissive conformation to D4Z4 chromatin. This is evidenced by changes in histone modification, partial but variable hypomethylation of D4Z4 in FSHD1, and more extensive hypomethylation in FSHD2 (Himeda et al., 2015). However, D4Z4 hypomethylation does not suffice for the disease, since there is an absence of muscular dystrophy symptoms in patients with ICF (immunodeficiency, centromeric region instability and facial anomalies), a rare, unrelated DNA hypomethylation-associated disease in which D4Z4 is strongly hypomethylated (OMIM Entry-#614069).

DUX4 is a homeobox transcription factor protein, and expression of DUX4 in muscle induces a transcriptional program leading to expression of downstream genes and protein products that are not normally expressed in skeletal muscle. For example, DUX4 expression results in the induction of several germline genes in FSHD skeletal muscles and in transfected cells (Yao et al, 2014; Ehrlich and Lacey, 2012). Many of these novel transcripts are expressed in FSHD muscle cells but not in control muscle cells (Yao et al., 2014; Homma et al., 2015; Shadle et al., 2017; Bosnakovski et al., 2014). Since some of the downstream target genes of DUX4 encode transcription factors, DUX4 pathological activation leads to a large gene expression deregulation cascade in muscle, which causes the disease (Yao et al., 2014; Homma et al., 2015; Shadle et al., 2017; Bosnakovski et al., 2014).

Endogenous (in the FSHD myofiber) and forced DUX4 expression in muscle cells is toxic, leads to apoptosis and oxidative stress, and interferes with myogenesis and sarcomere function (Rickard et al., 2015; Homma et al., 2015; Bosnokovski et al., 2014; Tawil et al., 2014; Himeda et al., 2015). Clinical heterogeneity in both disease progression and age of onset can be accounted for, in part, by epigenetic instability leading to progressive changes in DUX4 transcription. The role of DNA hypomethylation and permissive DUX4 transcription is exemplified by the high clinical severity observed in patients who inherited combined FSHD1 and 2 defects (reviewed in Tawil et al., 2014; van der Maarel et al., 2007). Clinical heterogeneity is also explained by differences in the severity of D4Z4 repeat shortening, with more severe phenotype and younger age at onset in patients with shorter repeats (1-3) compared to patients with less severely contracted repeats (4-7).

DUX4 is now recognized as the cause of the pathology of FSHD, since activation of its target genes is the main molecular signature in FSHD muscle (Reviewed in Tawil et al., 2014; Himeda et al., 2015). Major downstream target genes are members of highly homologous gene families that are clustered spatially on chromosomes, including PRAMEF (preferentially expressed in melanoma), TRIM (tripartite motif-containing), MBDL (methyl-CpG binding protein-like), ZSCAN (zinc finger and SCAN domain containing) and RFPL (ret-finger protein-like) families (Geng et al., 2012; Yao et al., 2014; Shadle et al., 2017; Ehrlich and Lacey, 2012; Tawil et al., 2014; van der Maarel et al., 2007). Discrimination between FSHD and control skeletal muscle can be made using ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, ZNF280A etc. (described in but not limited to Yao et al., 2014; Shadle et al., 2017; Ehrlich and Lacey, 2012).

Annotated chemical probes were screened to identify disease-modifying small molecule drug targets that reduce DUX4 expression in FSHD myotubes. These screens identified multiple chemical scaffolds that inhibit the activity of p38 mitogen-activated protein kinase alpha (MAPK14 or p38α). As described in the accompanying Examples, it has been shown that knockdown of the MAPK14 gene using small interfering RNA (siRNA) technology or CRISPR-mediated genome editing with specific guide RNA's (gRNAs) that selectively target the alpha isoform of p38 kinase also reduces DUX4 and DUX4-related downstream gene expression in FSHD myotubes. It was also found that selective p38α and β kinase inhibitors specifically reduced DUX4 and its downstream genes in FSHD myotubes, thereby impacting the core pathophysiology of the FSHD disease process (data exemplified herein). The same experiments revealed that p38α and β kinase inhibitors do not impact myogenin or the expression of other myogenic factors, nor do they impact proliferation of myoblasts or differentiation of myoblasts exhibited by myogenic fusion in FSHD myotubes, thereby demonstrating that the effect is not due to overall toxicity to muscle. These p38 kinase inhibitor small molecules reduce the expression of DUX4 and related downstream genes, thereby impacting pathophysiology of the FSHD disease process, including reducing apoptotic cell death. p38-mediated DUX4 reduction would be expected to impact downstream inflammatory, fatty infiltration, and fibrotic processes in FSHD.

Members of the p38 MAPK family, composed of α, β, γ and δ, isoforms are encoded by separate genes that play a critical role in cellular responses needed for adaptation to stress and survival (reviewed in Whitmarsh 2010; Martin et al., 2014; Krementsov et al., 2013). In many inflammatory diseases, including cardiovascular and other chronic diseases, these same p38 MAPK stress-induced signals can trigger maladaptive responses that aggravate, rather than alleviate, the disease (reviewed in Whitmarsh 2010; Martin et al., 2014). Indeed, in skeletal muscle, a variety of cellular stresses including chronic exercise, insulin exposure and altered endocrine states, myoblast differentiation into myocytes, reactive oxygen species, as well as apoptosis, have all been shown to induce the p38 kinase pathway (Keren, et. al., 2006; Zarubin et al., 2006). In fact, the p38 kinase pathway can be activated by a number of external stimuli, including pro-inflammatory cytokines and cellular stress, leading to activation of the dual-specificity MAPK kinases MKK3 and MKK6. Activation of MKK3 and MKK6, which in turn phosphorylate p38 in its activation loop, trigger downstream phosphorylation events. These include phosphorylation of HSP27, MAPKAPK2 (MK2) and a variety of transcription factors, culminating in transcriptional changes in the nucleus. A modest number of p38-regulated transcripts and a large number of downstream effectors of p38 kinase have been identified (described in Cuenda et al., 2007 and Kyriakis et.al., 2001, Viemann et al. 2004).

Several compounds from different chemical scaffolds that inhibit the p38α MAPK signaling pathway have entered clinical trials in diverse (non-neuromuscular) indications, including rheumatoid arthritis, chronic obstructive pulmonary disease, pain, cardiovascular diseases, and cancer. Inhibition of p38α and β in clinical trials has proven to be safe. In vitro and in vivo pharmacology suggest that p38α target engagement in these clinical studies was robust, as demonstrated by measuring reduction in phosphorylation of HSP27 (an indirect target) and pMK2 (a direct target).

p38α MAPK is known to play critical roles in skeletal muscle biology, specifically in abrogating proliferating myoblasts to differentiation and subsequently fusion to form multi-nucleated myotubes. Treatment of muscular dystrophy patients that are constitutively undergoing processes of degeneration and regeneration with p38α inhibitors would not be obvious. Complete knockout (KO) of p38α is embryonically lethal. Embryonic rescue allows for survival of pups to a few days postnatal and isolation of satellite cells to study myogenic precursors lacking p38α. Myoblasts completely lacking p38α express significantly less critical differentiation genes and show severe deficits in fusion. Histology of P2 pups show significantly increased cycling satellite cells and a left-shifted fiber distribution. (Perdiguero et. al, 2007). Importantly, KO of p38α in mature muscle (cre driven by Myl1 promoter) shows no deficiencies in early time points, but mice deficient in p38α at 6 months of age show significantly greater regeneration and type I fibers, as well as a smaller fiber distribution compared to controls (Wissing et. al, 2014). These data suggest that inhibition of p38α would trigger skeletal muscle regeneration in diseases deficient in regeneration in addition to FSHD by a mechanism independent of regulation of DUX4 expression.

In skeletal muscle, p38 has been shown to regulate gene expression during myogenesis. p38γ has been shown to be required for myogenesis using both specific gene knock out and conditional knock out approaches (Cuenda et.al., 2007; Kerin et.al., 2006; Aouadi et.al., 2006). In the adult, selective inhibitors of p38α and β avoid p38γ-related impact to myogenesis.

The present disclosure finds that p38 is activated during myogenesis, and that inhibition of p38α and β by molecules exemplified herein, including FTX-839, FTX-1821, etc., profoundly reduces DUX4 expression and its downstream gene program in FSHD myotubes (data exemplified herein). Without wishing to be bound by theory, p38α appears to directly regulate DUX4 expression by impacting the activity of critical myogenic enhancers required for pathologic DUX4 expression at the level of the mutated D4Z4 locus with shorter repeats (FSHD1) or SMCHD1 mutations (FSHD2) or when repression is lost by other mechanisms in the muscle of FSHD patients. This is a differentiated mechanism from the previous clinical studies, which targeted functions of p38 in the cytoplasm and failed to show efficacy in numerous diseases, including rheumatoid arthritis, pain, depression, chronic obstructive pulmonary disease, and cardiovascular disease. Inhibitors of p38 have never been explored clinically for FSHD.

As used in this specification and the appended claims, the singular forms "a," "an" and "the" include plural references unless the content clearly dictates otherwise.

As used in this specification, the term "and/or" is used in this disclosure to either "and" or "or" unless indicated otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration" refers herein to introducing an agent or composition into a subject or contacting an agent or composition with a cell and/or tissue.

In certain aspects, the disclosure includes a method for reducing the expression or activity of a DUX4 gene, mRNA, or polypeptide, or for reducing the expression or activity of a DUX4 downstream gene or polypeptide, including but not limited to any of those disclosed herein, in a cell, tissue, organ, or subject. In particular embodiments, the DUX4 mRNA is DUX4-fl. As used herein, the term "DUX4 downstream gene" refers to a gene that is transcriptionally activated (i.e., its expression is increased) by DUX4, and the term "DUX4 downstream polypeptide" refers to the encoded polypeptide. Illustrative examples if DUX4 downstream genes are provided herein. In certain embodiments, the DUX4 downstream gene is selected from those shown in FIG. 10A.

The methods disclosed herein may be practiced in vitro or in vivo, and in certain embodiments, the methods comprise contacting a cell, tissue, organ or subject with a p38 inhibitor, resulting in a reduced amount of active p38 protein in the cell, tissue, organ or subject. The term "p38 inhibitor" may refer to any agents that results in a reduced amount of active p38 protein in the cell, tissue, organ, or subject. The amount of active p38 protein in a cell may be reduced via a variety of means, including but not limited to reducing the total amount of p38 protein or inhibiting one or more activity of the p38 protein. In various embodiments, a p38 inhibitor may inhibit the expression of a p38 gene, a p38 mRNA, or a p38 protein, and/or a p38 inhibitor may inhibit a biological activity of a p38 protein. In certain embodiments, the biological activity is kinase activity. For example, a p38 inhibitor may competitively bind to the ATP-binding site of p38 MAPK and inhibit its kinase activity, or it may allosterically block the kinase activity of the p38 MAPK. In certain embodiments, a p38 inhibitor causes increased degradation of a p38 protein. In particular embodiments, the p38 gene or p38 protein is a mammalian p38 gene or mammalian p38 protein, e.g., a human p38 gene or human p38 protein, e.g., a human p38-α (MAPK14) or p38-β (MAPK11) gene or protein.

p38 MAP Kinase (MAPK), also called RK or CSBP (Cytokinin Specific Binding Protein), is the mammalian orthologue of the yeast Hog1p MAP kinase, which participates in a signaling cascade controlling cellular responses to cytokines and stress. Four p38 MAP kinases, p38-α (MAPK14), -β (MAPK11), -γ (MAPK12/ERK6), and δ (MAPK13/SAPK4), have been identified. These include various isoforms. In particular embodiments, any of these may be targeted by the methods disclosed herein. In certain embodiments, the p38 inhibitor inhibits p38-α (MAPK14) or p38-β (MAPK11), e.g., human versions of these genes or proteins.

In certain embodiment, the targeted p38 protein comprises the amino acid sequence set forth below or disclosed in GenBank accession NP_001306.1 for p38 kinase (mitogen-activated protein kinase 14 isoform 1, *Homo sapiens*):

```
                                             (SEQ ID NO: 1)
MSQERPTFYRQELNKTIWEVPERYQNLSPVGSGAYGSVCAAFDTKTG

LRVAVKKLSRPFQSIIHAKRTYRELRLLKHMKHENVIGLLDVFTPAR

SLEEFNDVYLVTHLMGADLNNIVKCQKLTDDHVQFLIYQILRGLKYI

HSADIIHRDLKPSNLAVNEDCELKILDFGLARHTDDEMTGYVATRWY

RAPEIMLNWMHYNQTVDIWSVGCIMAELLTGRTLFPGTDHIDQLKLI

LRLVGTPGAELLKKISSESARNYIQSLTQMPKMNFANVFIGANPLAV

DLLEKMLVLDSDKRITAAQALAHAYFAQYHDPDDEPVADPYDQSFES

RDLLIDEWKSLTYDEVISFVPPPLDQEEMES.
```

In certain embodiments, the targeted p38 gene, cDNA, mRNA or coding sequence comprises the p38-α nucleic acid sequence set forth below or disclosed in GenBank accession NM_001315.2, or a complement thereof:

(SEQ ID NO: 2)
TTCTCTCACGAAGCCCCGCCCGCGGAGAGGTTCCATATTGGGTAAA

ATCTCGGCTCTCGGAGAGTCCCGGGAGCTGTTCTCGCGAGAGTACT

GCGGGAGGCTCCCGTTTGCTGGCTCTTGGAACCGCGACCACTGGAG

CCTTAGCGGGCGCAGCAGCTGGAACGGGAGTACTGCGACGCAGCCC

GGAGTCGGCCTTGTAGGGGCGAAGGTGCAGGGAGATCGCGGCGGGC

GCAGTCTTGAGCGCCGGAGCGCGTCCCTGCCCTTAGCGGGGCTTGC

CCCAGTCGCAGGGGCACATCCAGCCGCTGCGGCTGACAGCAGCCGC

GCGCGCGGGAGTCTGCGGGGTCGCGGCAGCCGCACCTGCGCGGGCG

ACCAGCGCAAGGTCCCCGCCCGGCTGGGCGGGCAGCAAGGGCCGGG

GAGAGGGTGCGGGTGCAGGCGGGGGCCCCACAGGGCCACCTTCTTG

CCCGGCGGCTGCCGCTGGAAAATGTCTCAGGAGAGGCCCACGTTCT

ACCGGCAGGAGCTGAACAAGACAATCTGGGAGGTGCCCGAGCGTTA

CCAGAACCTGTCTCCAGTGGGCTCTGGCGCCTATGGCTCTGTGTGT

GCTGCTTTTGACACAAAAACGGGGTTACGTGTGGCAGTGAAGAAGC

TCTCCAGACCATTTCAGTCCATCATTCATGCGAAAAGAACCTACAG

AGAACTGCGGTTACTTAAACATATGAAACATGAAAATGTGATTGGT

CTGTTGGACGTTTTTACACCTGCAAGGTCTCTGGAGGAATTCAATG

ATGTGTATCTGGTGACCCATCTCATGGGGGCAGATCTGAACAACAT

TGTGAAATGTCAGAAGCTTACAGATGACCATGTTCAGTTCCTTATC

TACCAAATTCTCCGAGGTCTAAAGTATATACATTCAGCTGACATAA

TTCACAGGGACCTAAAACCTAGTAATCTAGCTGTGAATGAAGACTG

TGAGCTGAAGATTCTGGATTTTGGACTGGCTCGGCACACAGATGAT

GAAATGACAGGCTACGTGGCCACTAGGTGGTACAGGGCTCCTGAGA

TCATGCTGAACTGGATGCATTACAACCAGACAGTTGATATTTGGTC

AGTGGGATGCATAATGGCCGAGCTGTTGACTGGAAGAACATTGTTT

CCTGGTACAGACCATATTAACCAGCTTCAGCAGATTATGCGTCTGA

CAGGAACACCCCCGCTTATCTCATTAACAGGATGCCAAGCCATGA

GGCAAGAAACTATATTCAGTCTTTGACTCAGATGCCGAAGATGAAC

TTTGCGAATGTATTTATTGGTGCCAATCCCCTGGCTGTCGACTTGC

TGGAGAAGATGCTTGTATTGGACTCAGATAAGAGAATTACAGCGGC

CCAAGCCCTTGCACATGCCTACTTTGCTCAGTACCACGATCCTGAT

GATGAACCAGTGGCCGATCCTTATGATCAGTCCTTTGAAAGCAGGG

ACCTCCTTATAGATGAGTGGAAAAGCCTGACCTATGATGAAGTCAT

CAGCTTTGTGCCACCACCCCTTGACCAAGAAGAGATGGAGTCCTGA

GCACCTGGTTTCTGTTCTGTTGATCCCACTTCACTGTGAGGGGAAG

GCCTTTTCACGGGAACTCTCCAAATATTATTCAAGTGCCTCTTGTT

GCAGAGATTTCCTCCATGGTGGAAGGGGGTGTGCGTGCGTGTGCGT

GCGTGTTAGTGTGTGTGCATGTGTGTGTCTGTCTTTGTGGGAGGGT

AAGACAATATGAACAAACTATGATCACAGTGACTTTACAGGAGGTT

GTGGATGCTCCAGGGCAGCCTCCACCTTGCTCTTCTTTCTGAGAGT

TGGCTCAGGCAGACAAGAGCTGCTGTCCTTTTAGGAATATGTTCAA

TGCAAAGTAAAAAAATATGAATTGTCCCCAATCCCGGTCATGCTTT

TGCCACTTTGGCTTCTCCTGTGACCCCACCTTGACGGTGGGGCGTA

GACTTGACAACATCCCACAGTGGCACGGAGAGAAGGCCCATACCTT

CTGGTTGCTTCAGACCTGACACCGTCCCTCAGTGATACGTACAGCC

AAAAAGGACCAACTGGCTTCTGTGCACTAGCCTGTGATTAACTTGC

TTAGTATGGTTCTCAGATCTTGACAGTATATTTGAAACTGTAAATA

TGTTTGTGCCTTAAAAGGAGAGAAGAAAGTGTAGATAGTTAAAAGA

CTGCAGCTGCTGAAGTTCTGAGCCGGGCAAGTCGAGAGGGCTGTTG

GACAGCTGCTTGTGGGCCCGGAGTAATCAGGCAGCCTTCATAGGCG

GTCATGTGTGCATGTGAGCACATGCGTATATGTGCGTCTCTCTTTC

TCCCTCACCCCCAGGTGTTGCCATTTCTCTGCTTACCCTTCACCTT

TGGTGCAGAGGTTTCTTGAATATCTGCCCCAGTAGTCAGAAGCAGG

TTCTTGATGTCATGTACTTCCTGTGTACTCTTTATTTCTAGCAGAG

TGAGGATGTGTTTTGCACGTCTTGCTATTTGAGCATGCACAGCTGC

TTGTCCTGCTCTCTTCAGGAGGCCCTGGTGTCAGGCAGGTTTGCCA

GTGAAGACTTCTTGGGTAGTTTAGATCCCATGTCACCTCAGCTGAT

ATTATGGCAAGTGATATCACCTCTCTTCAGCCCCTAGTGCTATTCT

GTGTTGAACACAATTGATACTTCAGGTGCTTTTGATGTGAAAATCA

TGAAAAGAGGAACAGGTGGATGTATAGCATTTTTATTCATGCCATC

TGTTTTCAACCAACTATTTTTGAGGAATTATCATGGGAAAAGACCA

GGGCTTTTCCCAGGAATATCCCAAACTTCGGAAACAAGTTATTCTC

TTCACTCCCAATAACTAATGCTAAGAAATGCTGAAAATCAAAGTAA

AAAATTAAAGCCCATAAGGCCAGAAACTCCTTTTGCTGTCTTTCTC

TAAATATGATTACTTTAAAATAAAAAGTAACAAGGTGTCTTTTCC

ACTCCTATGGAAAAGGGTCTTCTTGGCAGCTTAACATTGACTTCTT

GGTTTGGGGAGAAATAAATTTTGTTTCAGAATTTTGTATATTGTAG

GAATCCTTTGAGAATGTGATTCCTTTTGATGGGGAGAAAGGGCAAA

TTATTTAATATTTTGTATTTTCAACTTTATAAAGATAAAATATCC

TCAGGGGTGGAGAAGTGTCGTTTTCATAACTTGCTGAATTTCAGGC

ATTTTGTTCTACATGAGGACTCATATATTTAAGCCTTTTGTGTAAT

AAGAAAGTATAAAGTCACTTCCAGTGTTGGCTGTGTGACAGAATCT

TGTATTTGGGCCAAGGTGTTTCCATTTCTCAATCAGTGCAGTGATA

CATGTACTCCAGAGGGACAGGGTGGACCCCCTGAGTCAACTGGAGC

AAGAAGGAAGGAGGCAGACTGATGGCGATTCCCTCTCACCCGGGAC

TCTCCCCCTTTCAAGGAAAGTGAACCTTTAAAGTAAAGGCCTCATC

TCCTTTATTGCAGTTCAAATCCTCACCATCCACAGCAAGATGAATT

TTATCAGCCATGTTTGGTTGTAAATGCTCGTGTGATTTCCTACAGA

AATACTGCTCTGAATATTTTGTAATAAAGGTCTTTGCACATGTGAC

-continued
CACATACGTGTTAGGAGGCTGCATGCTCTGGAAGCCTGGACTCTAA

GCTGGAGCTCTTGGAAGAGCTCTTCGGTTTCTGAGCATAATGCTCC

CATCTCCTGATTTCTCTGAACAGAAAACAAAAGAGAGAATGAGGGA

AATTGCTATTTTATTTGTATTCATGAACTTGGCTGTAATCAGTTAT

GCCGTATAGGATGTCAGACAATACCACTGGTTAAAATAAAGCCTAT

TTTTCAAATTTAGTGAGTTTCTCAAGTTTATTATATTTTTCTCTTG

TTTTTATTTAATGCACAATATGGCATTATATCAATATCCTTTAAAC

TGTGACCTGGCATACTTGTCTGACAGATCTTAATACTACTCCTAAC

ATTTAGAAAATGTTGATAAAGCTTCTTAGTTGTACATTTTTTGGTG

AAGAGTATCCAGGTCTTTGCTGTGGATGGGTAAAGCAAAGAGCAAA

TGAACGAAGTATTAAGCATTGGGGCCTGTCTTATCTACACTCGAGT

GTAAGAGTGGCCGAAATGACAGGGCTCAGCAGACTGTGGCCTGAGG

GCCAAATCTGGCCCACCACCTGTTTGGTGTAGCCTGCTAAGAATGG

CTTTTACATTTTTAAATGGTTGGGAAAGAAAAAAAAAGAAGTAGTA

GATTTTGTAGCATGTGATGTAAGTAATGTAAAACTTAAATTCCAGT

ATCCATAAATAAAGTTTTATGAGAACAGA.

In certain embodiment, the targeted p38 protein comprises the amino acid sequence set forth below or disclosed in GenBank accession NP_002742.3 for p38 kinase (mitogen-activated protein kinase 11 isoform 1, Homo sapiens):

(SEQ ID NO: 3)
MSGPRAGFYRQELNKTVWEVPQRLQGLRPVGSGAYGSVCSAYDARL

RQKVAVKKLSRPFQSLIHARRTYRELRLLKHLKHENVIGLLDVFTP

ATSIEDFSEVYLVTTLMGADLNNIVKCQALSDEHVQFLVYQLLRGL

KYIHSAGIIHRDLKPSNVAVNEDCELRILDFGLARQADEEMTGYVA

TRWYRAPEIMLNWMHYNQTVDIWSVGCIMAELLQGKALFPGSDYID

QLKRIMEVVGTPSPEVLAKISSEHARTYIQSLPPMPQKDLSSIFRG

ANPLAIDLLGRMLVLDSDQRVSAAEALAHAYFSQYHDPEDEPEAEP

YDESVEAKERTLEEWKELTYQEVLSFKPPEPPKPPGSLEIEQ.

In certain embodiments, the targeted p38 gene, cDNA, mRNA or coding sequence comprises the p38-β nucleic acid sequence set forth below or disclosed in GenBank accession NM_002751.6, or a complement thereof:

(SEQ ID NO: 4)
CGCCGCCTCCGCCGCCCTCCGCTCCGCTCGGCTCGGGCTCGGCTC

GGGCGCGGGCGCGGGGCGCGGGGCTGGGCCCGGGCGGAGCGGCGG

CTGCTCCGGACATGTCGGGCCCTCGCGCCGGCTTCTACCGGCAGG

AGCTGAACAAGACCGTGTGGGAGGTGCCGCAGCGGCTGCAGGGGC

TGCGCCCGGTGGGCTCCGGCGCCTACGGCTCCGTCTGTTCGGCCT

ACGACGCCCGGCTGCGCCAGAAGGTGGCGGTGAAGAAGCTGTCGC

GCCCCTTCCAGTCGCTGATCCACGCGCGCAGAACGTACCGGGAGC

TGCGGCTGCTCAAGCACCTGAAGCACGAGAACGTCATCGGGCTTC

TGGACGTCTTCACGCCGGCCACGTCCATCGAGGACTTCAGCGAAG

TGTACTTGGTGACCACCCTGATGGGCGCCGACCTGAACAACATCG

TCAAGTGCCAGGCGCTGAGCGACGAGCACGTTCAATTCCTGGTTT

ACCAGCTGCTGCGCGGGCTGAAGTACATCCACTCGGCCGGGATCA

TCCACCGGGACCTGAAGCCCAGCAACGTGGCTGTGAACGAGGACT

GTGAGCTCAGGATCCTGGATTTCGGGCTGGCGCGCCAGGCGGACG

AGGAGATGACCGGCTATGTGGCCACGCGCTGGTACCGGGCACCTG

AGATCATGCTCAACTGGATGCATTACAACCAAACAGTGGATATCT

GGTCCGTGGGCTGCATCATGGCTGAGCTGCTCCAGGGCAAGGCCC

TCTTCCCGGGAAGCGACTACATTGACCAGCTGAAGCGCATCATGG

AAGTGGTGGGCACACCCAGCCCTGAGGTTCTGGCAAAAATCTCCT

CAGAACACGCCCGGACATATATCCAGTCCCTGCCCCCCATGCCCC

AGAAGGACCTGAGCAGCATCTTCCGTGGAGCCAACCCCCTGGCCA

TAGACCTCCTTGGAAGGATGCTGGTGCTGGACAGTGACCAGAGGG

TCAGTGCAGCTGAGGCACTGGCCCACGCCTACTTCAGCCAGTACC

ACGACCCCGAGGATGAGCCAGAGGCCGAGCCATATGATGAGAGCG

TTGAGGCCAAGGAGCGCACGCTGGAGGAGTGGAAGGAGCTCACTT

ACCAGGAAGTCCTCAGCTTCAAGCCCCCAGAGCCACCGAAGCCAC

CTGGCAGCCTGGAGATTGAGCAGTGAGGTGCTGCCCAGCAGCCCC

TGAGAGCCTGTGGAGGGGCTTGGGCCTGCACCCTTCCACAGCTGG

CCTGGTTTCCTCGAGAGGCACCTCCCACACTCCTATGGTCACAGA

CTTCTGGCCTAGGACCCCTCGCCTTCAGGAGAATCTACACGCATG

TATGCATGCACAAACATGTGTGTACATGTGCTTGCCATGTGTAGG

AGTCTGGGCACAAGTGTCCCTGGGCCTACCTTGGTCCTCCTGTCC

TCTTCTGGCTACTGCACTCTCCACTGGGACCTGACTGTGGGGTCC

TAGATGCCAAAGGGGTTCCCCTGCGGAGTTCCCCTGTCTGTCCCA

GGCCGACCCAAGGGAGTGTCAGCCTTGGGCTCTCTTCTGTCCCAG

GGCTTTCTGGAGGACGCGCTGGGGCCGGGACCCCGGGAGACTCAA

AGGGAGAGGTCTCAGTGGTTAGAGCTGCTCAGCCTGGAGGTAGGG

GGCTGTCTTGGTCACTGCTGAGACCCACAGGTCTAAGAGGAGAGG

CAGAGCCAGTGTGCCACCAGGCTGGGCAGGGACAACCACCAGGTG

TCAAATGAGAAAAGCTGCCTGGAGTCTTGTGTTCACCCGTGGGTG

TGTGTGGGCACGTGTGGATGAGCGTGCACTCCCCGTGTTCATATG

TCAGGGCACATGTGATGTGGTGCGTGTGAATCTGTGGGCGCCCAA

GGCCAGCAGCCATATCTGGCAAGAAGCTGGAGCCGGGGTGGGTGT

GCTGTTGCCTTCCCTCTCCTCGGTTCCTGATGCCTTGAGGGGTGT

TTCAGACTGGCGGCTCCAGTGGGCCAAAGGGCAACCACATGAGCA

TGGGCAGGGGCTTTCTCCTTGGATGTGGGACCCACAGCAGCAGGC

TTCCTGAGGCTGGGGGTGGGTGGGTGGGTGGTTTGGCCTTGAGGA

CGCTAGGGCAGCACACCTGGATGTGGACTTGGACTCGGACACTTC

TGCCCTGCACCCTGGCCCGCTCTCTACCTCTGCCCACCGTTGTGG

In certain embodiments, methods disclosed herein comprising contacting a cell, tissue, organ, or subject with a p38 inhibitor, are practiced to inhibit or decrease the expression or activity of DUX4 or one or more DUX4 downstream genes. In certain embodiments, the DUX4 or DUX4 downstream gene is a human gene. For example, the DUX4 double homeobox 4 (Homo sapiens) gene may comprise the nucleotide sequence set forth below or disclosed in GenBank accession NG_034189.2, or a complement thereof:

```
                                          (SEQ ID NO: 5)
ATGGCCCTCCCGACACCCTCGGACAGCACCCTCCCCGCGGAAGC

CCGGGGACGAGGACGGCGACGGAGACTCGTTTGGACCCCGAGCC

AAAGCGAGGCCCTGCGAGCCTGCTTTGAGCGGAACCCGTACCCG

GGCATCGCCACCAGAGAACGGCTGGCCCAGGCCATCGGCATTCC

GGAGCCCAGGGTCCAGATTTGGTTTCAGAATGAGAGGTCACGCC

AGCTGAGGCAGCACCGGCGGGAATCTCGGCCCTGGCCCGGGAGA

CGCGGCCCGCCAGAAGGCCGGCGAAAGCGGACCGCCGTCACCGG

ATCCCAGACCGCCCTGCTCCTCCGAGCCTTTGAGAAGGATCGCT

TTCCAGGCATCGCCGCCCGGGAGGAGCTGGCCAGAGAGACGGGC

CTCCCCGGAGTCCAGGATTCAGATCTGGTTTCAGAATCGAAGGGC

CAGGCACCCGGGACAGGGTGGCAGGGCGCCCGCGCAGGCAGGCG

GCCTGTGCAGCGCGGCCCCCGGCGGGGGTCACCCTGCTCCCTCG

TGGGTCGCCTTCGCCCACACCGGCGCGTGGGGAACGGGGCTTCC

CGCACCCCACGTGCCCTGCGCGCCTGGGGCTCTCCCACAGGGGG

CTTTCGTGAGCCAGGCAGCGAGGGCCGCCCCCGCGCTGCAGCCC

AGCCAGGCCGCGCCGGCAGAGGGGATCTCCCAACCTGCCCCGGC

GCGCGGGGATTTCGCCTACGCCGCCCCGGCTCCTCCGGACGGGG

CGCTCTCCCACCCTCAGGCTCCTCGCTGGCCTCCGCACCCGGGC

AAAAGCCGGGAGGACCGGGACCCGCAGCGCGACGGCCTGCCGGG

CCCCTGCGCGGTGGCACAGCCTGGGCCCGCTCAAGCGGGGCCGC

AGGGCCAAGGGGTGCTTGCGCCACCCACGTCCCAGGGGAGTCCG

TGGTGGGGCTGGGGCCGGGGTCCCCAGGTCGCCGGGGCGGCGTG

GGAACCCCAAGCCGGGGCAGCTCCACCTCCCCAGCCCGCGCCCC

CGGACGCCTCCGCCTCCGCGCGGCAGGGGCAGATGCAAGGCATC

CCGGCGCCCTCCCAGGCGCTCCAGGAGCCGGCGCCCTGGTCTGC

ACTCCCCTGCGGCCTGCTGCTGGATGAGCTCCTGGCGAGCCCGG

AGTTTCTGCAGCAGGCGCAACCTCTCCTAGAAACGGAGGCCCCG

GGGGAGCTGGAGGCCTCGGAAGAGGCCGCCTCGCTGGAAGCACC

CCTCAGCGAGGAAGAATACCGGGCTCTGCTGGAGGAGCTTTAGG

ACGCGGGGTTGGGACGGGGTCGGGTGGTTCGGGGCAGGGCGGTG

GCCTCTCTTTCGCGGGGAACACCTGGCTGGCTACGGAGGGGCGT

GTCTCCGCCCCGCCCCCTCCACCGGGCTGACCGGCCTGGGATTC

CTGCCTTCTAGGTCTAGGCCCGGTGAGAGACTCCACACCGCGGA

GAACTGCCATTCTTTCCTGGGCATCCCGGGGATCCCAGAGCCGG

CCCAGGTACCAGCAGGTGGGCCGCCTACTGCGCACGCGCGGGTT

TGCGGGCAGCCGCCTGGGCTGTGGGAGCAGCCCGGGCAGAGCTC

TCCTGCCTCTCCACCAGCCCACCCCGCCGCCTGACCGCCCCCTC

CCCACCCCCACCCCCACCCCCGGAAAACGCGTCGTCCCCTGGG

CTGGGTGGAGACCCCCGTCCCGCGAAACACCGGGCCCCGCGCAG

CGTCCGGGCCTGACACCGCTCCGGCGGCTCGCCTCCTCTGCGCC

CCCGCGCCACCGTCGCCCGCCCGCCCGGGCCCCTGCAGCCTCCC

AGCTGCCAGCACGGAGCGCCTGGCGGTCAAAAGCATACCTCTGT

CTGTCTTTGCCCGCTTCCTGGCTAGACCTGCGCGCAGTGCGCAC

CCCGGCTGACGTGCAAGGGAGCTCGCTGGCCTCTCTGTGCCCTT

GTTCTTCCGTGAAATTCTGGCTGAATGTCTCCCCCCACCTTCCG

ACGCTGTCTAGGCAAACCTGGATTAGAGTTACATCTCCTGGATG

ATTAGTTCAGAGATATATTAAAATGCCCCCTCCCTGTGGATCCT

ATAG.
```

For example, the DUX4 double homeobox 4 [Homo sapiens] mRNA gene may comprise the nucleotide sequence set forth below or disclosed in GenBank accession NM_001293798.2, or a complement thereof:

```
                                          (SEQ ID NO: 6)
ATGGCCCTCCCGACACCCTCGGACAGCACCCTCCCCGCGGAAGCCCGGG

GACGAGGACGGCGACGGAGACTCGTTTGGACCCCGAGCCAAAGCGAGGC

CCTGCGAGCCTGCTTTGAGCGGAACCCGTACCCGGGCATCGCCACCAGA

GAACGGCTGGCCCAGGCCATCGGCATTCCGGAGCCCAGGGTCCAGATTT

GGTTTCAGAATGAGAGGTCACGCCAGCTGAGGCAGCACCGGCGGGAATC

TCGGCCCTGGCCCGGGAGACGCGGCCCGCCAGAAGGCCGGCGAAAGCGG

ACCGCCGTCACCGGATCCCAGACCGCCCTGCTCCTCCGAGCCTTTGAGA

AGGATCGCTTTCCAGGCATCGCCGCCCGGGAGGAGCTGGCCAGAGAGAC

GGGCCTCCCGGAGTCCAGGATTCAGATCTGGTTTCAGAATCGAAGGGCC

AGGCACCCGGGACAGGGTGGCAGGGCGCCCGCGCAGGCAGGCGGCCTGT

GCAGCGCGGCCCCCGGCGGGGGTCACCCTGCTCCCTCGTGGGTCGCCTT

CGCCCACACCGGCGCGTGGGGAACGGGGCTTCCCGCACCCCACGTGCCC

TGCGCGCCTGGGGCTCTCCCACAGGGGGCTTTCGTGAGCCAGGCAGCGA

GGGCCGCCCCCGCGCTGCAGCCCAGCCAGGCCGCGCCGGCAGAGGGGAT

CTCCCAACCTGCCCCGGCGCGCGGGGATTTCGCCTACGCCGCCCCGGCT

CCTCCGGACGGGGCGCTCTCCCACCCTCAGGCTCCTCGCTGGCCTCCGC
```

-continued

```
ACCCGGGCAAAAGCCGGGAGGACCGGGACCCGCAGCGCGACGGCCTGCC

GGGCCCCTGCGCGGTGGCACAGCCTGGGCCCGCTCAAGCGGGGCCGCAG

GGCCAAGGGGTGCTTGCGCCACCCACGTCCCAGGGGAGTCCGTGGTGGG

GCTGGGGCCGGGGTCCCCAGGTCGCCGGGGCGGCGTGGGAACCCCAAGC

CGGGGCAGCTCCACCTCCCCAGCCCGCGCCCCCGGACGCCTCCGCCTCC

GCGCGGCAGGGGCAGATGCAAGGCATCCCGGCGCCCTCCCAGGCGCTCC

AGGAGCCGGCGCCCTGGTCTGCACTCCCCTGCGGCCTGCTGCTGGATGA

GCTCCTGGCGAGCCCGGAGTTTCTGCAGCAGGCGCAACCTCTCCTAGAA

ACGGAGGCCCCGGGGGAGCTGGAGGCCTCGGAAGAGGCCGCCTCGCTGG

AAGCACCCCTCAGCGAGGAAGAATACCGGGCTCTGCTGGAGGAGCTTTA

GGACGCGGGGTCTAGGCCCGGTGAGAGACTCCACACCGCGGAGAACTGC

CATTCTTTCCTGGGCATCCCGGGGATCCCAGAGCCGGCCCAGGTACCAG

CAGACCTGCGCGCAGTGCGCACCCCGGCTGACGTGCAAGGGAGCTCGCT

GGCCTCTCTGTGCCCTTGTTCTTCCGTGAAATTCTGGCTGAATGTCTCC

CCCCACCTTCCGACGCTGTCTAGGCAAACCTGGATTAGAGTTACATCTC

CTGGATGATTAGTTCAGAGATATATTAAAATGCCCCCTCCCTGTGGATC

CTATAG.
```

In particular embodiment, the DUX4 polypeptide sequence is as set forth below or disclosed in GenBank accession NP_001280727.1:

(SEQ ID NO: 7)
```
MALPTPSDSTLPAEARGRGRRRRLVWTPSQSEALRACFERNPYPGI

ATRERLAQAIGIPEPRVQIWFQNERSRQLRQHRRESRPWPGRRGPP

EGRRKRTAVTGSQTALLLRAFEKDRFPGIAAREELARETGLPESRI

QIWFQNRRARHPGQGGRAPAQAGGLCSAAPGGGHPAPSWVAFAHTG

AWGTGLPAPHVPCAPGALPQGAFVSQAARAAPALQPSQAAPAEGIS

QPAPARGDFAYAAPAPPDGALSHPQAPRWPPHPGKSREDRDPQRDG

LPGPCAVAQPGPAQAGPQGQGVLAPPTSQGSPWWGWGRGPQVAGAA

WEPQAGAAPPPQPAPPDASASARQGQMQGIPAPSQALQEPAPWSAL

PCGLLLDELLASPEFLQQAQPLLETEAPGELEASEEAASLEAPLSE

EEYRALLEEL.
```

Sequences of DUX4 downstream genes or targets are known in the art and illustrative DUX4 downstream genes are provided by the accession numbers shown below:

MBD3L2:
    Genomic nucleotide accession NC_000019.10 (7049340 . . . 7051735)
    mRNA nucleotide accession NM_144614.3
    protein polypeptide accession NP_653215.2

ZSCAN4:
    NC_000019.10 (57651497 . . . 57679152)
    NM_152677.2
    NP_689890.1

LEUTX:
    NC_000019.10 (39776594 . . . 39786135)
    NM_001143832.1
    NP_001137304.1

PRAMEF2:
    NC_000001.11 (12857086 . . . 12861909)
    NM_023014.1
    NP_075390.1

TRIM43:
    NC_000002.12 (95592018 . . . 95599723)
    NM_138800.2
    NP_620155.1

KHDC1L:
    NC_000006.12 (73223544 . . . 73225452, complement)
    NM_001126063.2
    NP_001119535.1

Methods of determining the expression level of p38, DUX4, or a DUX4 downstream gene or polypeptide in a biological sample, e.g., tissue, are known in the art and include, e.g., RT-PCR and FACS.

In one embodiment, a method of reducing the expression of a DUX4 mRNA (e.g., DUX4-fl), a DUX4 polypeptide, or a polypeptide encoded by a downstream target gene of DUX4, in a cell, tissue, organ, or subject, comprises contacting the cell, tissue, organ, or subject with an agent that results in a reduced amount of active p38 protein (also referred to herein as a p38 inhibitor), e.g., an inhibitor of p38-α and/or p38-β. In certain embodiments, the agent inhibits the expression or activity of a p38 protein. In certain embodiments, the agent causes increased degradation of a p38 protein, e.g., p38-α and/or p38-β. In particular embodiments, the cell or tissue is contacted with an amount of the agent effective to reduce the expression or activity of a DUX4 polypeptide, or a polypeptide encoded by a downstream target gene of DUX4, in the cell or tissue. In certain embodiments, the cell or tissue is contacted with an amount of the agent effective to reduce the amount of active p38 protein in the cell or tissue. In particular embodiments, the cells are muscle cells. In certain embodiments, the cells are terminally differentiated, e.g., terminally differentiated muscle cells. In some embodiments, the cells have an increased expression level of the DUX4 polypeptide, or the polypeptide encoded by the downstream target gene, as compared to the expression level in a control cell. In certain embodiments, the cells are associated with facioscapulohumeral muscular dystrophy (FSHD), e.g., FSHD1 or FSHD2. For example, the cells may be derived from or obtained from cells or tissue from a subject diagnosed with FSHD. Methods disclosed herein may be practiced in vitro or in vivo.

In an embodiment, the disclosure provides a method of reducing apoptosis of a cell or tissue, comprising contacting the cell or tissue with an agent that inhibits the expression or activity of a p38 protein (also referred to herein as a p38 inhibitor), e.g., an inhibitor of p38-α and/or p38-β. In particular embodiments, the cell or tissue is contacted with an amount of the agent effective to reduce the expression or activity of a DUX4 polypeptide, or a polypeptide encoded by a downstream target gene of DUX4, in the cell or tissue. In certain embodiments, the cell or tissue is contacted with an amount of the agent effective to reduce the amount of active p38 protein in the cell or tissue. In particular embodiments, the cells are muscle cells. In certain embodiments, the cells are terminally differentiated, e.g., terminally differentiated muscle cells. In some embodiments, the cells have an increased expression level of the DUX4 polypeptide, or the polypeptide encoded by the downstream target gene, as compared to the expression level in a control cell (i.e., before treatment). In certain embodiments, the cells are associated with facioscapulohumeral muscular dystrophy (FSHD), e.g., FSHD1 or FSHD2. For example, the cells may be derived from or obtained from cells or tissue from a subject diagnosed with FSHD. Methods disclosed herein may be practiced in vitro or in vivo.

In a related aspect, the disclosure includes a method of treating or preventing a disease or disorder associated with increased activity or expression of a DUX4 protein or a downstream target gene of DUX4 in a subject in need thereof, comprising providing to a subject a pharmaceutical composition comprising an effective amount of an agent that reduces the amount of active p38 protein (e.g., p38-α and/or p38-β) in the subject, or in certain cells or tissue of the subject. In some embodiments, the agent inhibits the expression or activity of a p38 protein, e.g., p38-α and/or p38-β. In certain embodiments, the agent induces degradation of the p38 protein. In certain embodiments, the agent inhibits activity of a p38 protein, e.g., inhibits kinase activity of the p38 protein. In particular embodiments of any of the methods, the p38 inhibitor reduces expression of DUX4 and/or one or more DUX4 downstream genes in cells or tissue of the subject.

In particular embodiments of methods of treatment disclosed herein, the disease or disorder is selected from FSHD 1, FSHD2, Immunodeficiency, Centromere instability and Facial anomalies syndrome (ICF), amyotrophic lateral sclerosis (ALS), inclusion body myositis (IBM), Ewing's Sarcoma, soft tissue sarcoma, rhabdomyosarcoma, and adult and pediatric B-cell acute lymphoblastic leukemia.

In particular embodiments of any of the methods disclosed herein, the subject is diagnosed with FSHD1 or FSHD2, and in certain embodiments, the subject comprises one or more genetic mutation associated with FSHD1 and/or FSHD2. In certain embodiments, the subject comprises reduced repression at a D4Z4 locus.

In certain embodiments of any of the methods disclosed herein, the subject is identified as having FSHD based upon the presence of a transcriptionally active DUX4. In another embodiment, the subject is identified as having FSHD based upon the presence of increased expression levels of one or more downstream genes, e.g., ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, or ZNF280A relative to a healthy control. In another embodiment, the subject is identified as having FSHD based upon the presence of a transcriptionally active DUX4 and increased expression levels of one or more DUX4 downstream genes, e.g., ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, or ZNF280A.

In another embodiment, the method may include measuring the expression level of one or more of DUX4 and DUX4 downstream genes, e.g., DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, or ZNF280A, in the subject prior to the administration of the p38 kinase inhibitor. The method may further include determining that the subject is in need of treatment if the expression level of one or more of DUX4 and DUX4 downstream genes, e.g., DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A KHDC1L is/are elevated relative to a healthy control.

In another embodiment, the method may include measuring the expression level of one or more of DUX 4 and DUX4 downstream genes, e.g., DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, or ZNF280A, in the cells of the subject before and after the administration of the p38 kinase inhibitor. The method may include comparing the expression level of one or more of DUX4 and DUX4 downstream genes, e.g., DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, or ZNF280A in the subject before and after the administration of the p38 kinase inhibitor. The method may include determining the effectiveness of treatment by the comparing of the expression level of one or more of DUX4 and DUX4 downstream genes, e.g., DUX4, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A before and after the administration of the p38 kinase inhibitor, wherein a decrease in the expression level(s) is indicative of effective treatment.

In some embodiments, the p38 kinase inhibitor reduces one or more downstream genes selected from ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A.

In one embodiment, a transcriptional modulator of DUX4 and downstream genes ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, PRAMEF15, and ZNF280A are inhibited by p38 kinase.

In particular embodiments, the subject comprises contraction of 4q35A D4Z4 array, such that the subject comprises ≤10 or ≤7 repeats (FSHD1). In certain embodiments, the subject, or one or more cells or tissues of the subject, comprises a deletion of one or more macrosatellite D4Z4 repeats in the subtelomeric region of chromosome 4q35, optionally wherein the cell comprises ≤7 macrosatellite D4Z4 repeats in the subtelomeric region of chromosome 4q35. In certain embodiments, the subject comprises one or more mutations in a Structural Maintenance Of Chromosomes Flexible Hinge Domain Containing 1 (SMCHD1) gene. In certain embodiments, the subject comprises at least one non-deleted 4qA allele. In certain embodiments, the subject comprises at least one non-deleted 4qA allele and an SMCHD1 mutation (FSHD2). In some embodiments, the subject is wheelchair bound (e.g., CSS 4.5 and 5). In certain embodiments, during or following treatment, the subject displays a reduced or decreased amount or rate of muscle degeneration e.g., a subject diagnosed with FSHD1 or FSHD2. In certain embodiments, during or following treatment, the subject displays a reduction of skeletal muscle replacement by fat, e.g., as determined via quantitative MRI, e.g., a reduction of at least 5%, at least 10%, at least 20%, at least 30%, at least 50%, or at least 70%. In certain embodiments, during or following treatment, the subject displays evidence of benefit on one or more of the following Clinical Outcome Assessments:

Shoulder/arm function as measured by Reachable Work Space (RWS) w/wo weights;

Mobility as measured by Time Up and Go (TUG) or a similar assay;

Patient reports of Activities of Daily Life (ADLs) and Quality of Life (QOL); and Quantitative skeletal muscle strength as measured by dynamometry.

In some embodiments, the subject displays any of these improvements for at least some time, e.g., for at least one week, one month, two months, six months, or one year following either commencement or cessation of treatment.

In another aspect, the disclosure provides the disclosed methods of using p38 inhibitors, e.g., an inhibitor of p38-α or p38-β, for treatment for FSHD1, FSHD2, ICF, and diseases where similar pathological changes are found, such ALS and IBM (Tawil et al., 2014).

In particular embodiments of any of the methods described herein, the pharmaceutical composition is provided to the subject parenterally.

In particular embodiments of any of the methods described herein, the pharmaceutical composition is provided to a muscle tissue of the subject.

In some certain embodiments, any of the methods described herein that comprise providing to the subject a p38 inhibitor may further comprise providing to the subject an additional therapy.

In particular embodiments, the additional therapy comprises clinical management. In one embodiment, the present invention provides a method for treating or preventing of FSHD 1, FSHD2, ICF, ALS, IBM, Ewing's Sarcoma, soft tissue sarcoma, rhabdomyosarcoma, and adult and pediatric B-cell acute lymphoblastic leukemia, where p38 inhibitors are used to decrease DUX4 and/or downstream gene and/or protein expression and/or activity and may be combined with clinical management involving physical therapy, aerobic exercise, respiratory function therapy, and/or orthopedic interventions.

In particular embodiments, the additional therapy comprises providing to the subject one or more myostatin inhibitors, anti-inflammatory agents, or gene therapy vectors, e.g., to reduce pathogenic DUX4 protein production in FSHD by controlling D4Z4 methylation, suppressing DUX4 mRNA, and/or inhibiting DUX4 signaling pathways. In one embodiment, the present disclosure provides a method of treatment of FSHD 1, FSHD2, ICF, ALS or IBM, in a subject in need thereof, where p38 inhibitors, e.g., inhibitors of p38-α or p38-β, are used to reduce DUX4 and downstream gene and/or protein expression and may be combined with myostatin inhibitors, anti-inflammatory agents, and/or gene therapy, e.g., to reduce pathogenic DUX4 protein production in FSHD by controlling D4Z4 methylation, suppressing DUX4 mRNA, and inhibiting DUX4 pathways. In certain embodiments, the methods are practiced using an inhibitor of p38 and a myostatin inhibitor. Particular myostatin pathway inhibitors that act extracellularly by either binding myostatin directly (Fstl3, Follistatin, myostatin antibody, GASP1, myostatin propeptide, decorin peptides, ActRIIB-Fc) or by binding its receptor complex (ActRIIB antibody) in order to block myostatin engaging its receptor complex and activating downstream signaling may be used in certain embodiments. Some of the myostatin inhibitors are naturally occurring (myostatin propeptide, Gasp1, follistatin, Fstl3) whereas others are engineered (myostatin antibody, ActRIIB antibody, ActRIIB-Fc).

In particular embodiments, the additional therapy comprises providing to the subject an inhibitor of DUX4 or a DUX4 downstream target or gene, e.g., an inhibitor that inhibits expression of DUX-4fl mRNA and/or DUX4 protein (or expression of mRNA or protein of a DUX4 downstream target) or an inhibitor that inhibits DUX4 activity, e.g., its activity as a transcriptional activator, or activity of a DUX4 downstream target. In particular embodiments, the inhibitor induces degradation of DUX4 polypeptide or DUX4 downstream target polypeptide. In particular embodiments, the inhibitor is an siRNA, miRNA, gRNA, shRNA, or antisense oligonucleotide that specifically binds a nucleic acid sequence or antisense thereof of a DUX4 or a DUX4 downstream target gene. In one embodiment, the present invention provides a method of treatment of FSHD 1, FSHD2, ICF, ALS or IBM, where p38 inhibitors are used to reduce DUX4 and downstream gene and protein expression and may be combined with an inhibitor of DUX4 or a DUX4 downstream target, e.g., small interfering RNA (siRNA), small hairpin RNA (shRNA), guide RNA (gRNA), microRNA (miRNA) and antisense oligonucleotides directed at DUX4 and/or one or more DUX4 downstream target transcripts (e.g., DNA or mRNA).

In certain embodiments, the present invention provides a method to use small molecule inhibitors of p38 kinase, e.g., an inhibitor of p38-α or p38-β, to reduce DUX4 and downstream gene expression in FSHD skeletal muscle myotubes to treat FSHD or any other disease or disorder disclosed herein and/or related to aberrant DUX4 expression or activity.

In some embodiments, p38, e.g., p38-α and/or p38-β, is inhibited by any of the small molecules or other agents disclosed herein.

p38 inhibitors and/or other agents and compositions (e.g., inhibitors) described herein can be formulated in any manner suitable for a desired administration route (e.g., parenteral or oral administration). In some embodiments, contacting an agent or composition with a cell and/or tissue is a result of administration of or providing an agent or composition to a subject. In some embodiments, an agent or composition (e.g., a p38 inhibitor) is administered at least 1, 2, 3, 4, 5, 10, 15, 20, or more times. In some embodiments of combination therapies, administration of a first agent or composition is followed by or occurs overlapping with or concurrently with the administration of a second agent or composition. The first and second agent or composition may be the same or they may be different. In some embodiments, the first and second agents or compositions are administered by the same actor and/or in the same geographic location. In some embodiments, the first and second agents or compositions are administered by different actors and/or in different geographical locations. In some embodiments, multiple agents described herein are administered as a single composition.

A wide variety of administration methods may be used in conjunction with the p38 inhibitors according to the methods disclosed herein. For example, p38 inhibitors may be administered or coadministered topically, orally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, intrathecally, transmucosally, pulmonary, or parenterally, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

"Subjects" includes animals (e.g., mammals, swine, fish, birds, insects etc.). In some embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals such as dogs and cats. In some embodiments (e.g., particularly in research contexts) subjects are rodents (e.g., mice, rats, hamsters), rabbits, primates, or swine such as inbred pigs and the like. The terms "subject" and "patient" are used interchangeably herein.

"Tissue" is an ensemble of similar cells from the same origin that together carry out a specific function. In certain embodiments, tissue is muscle tissue.

Methods disclosed herein may be practiced with any agent capable of inhibiting expression or activity of a p38 gene or protein, e.g., an inhibitor of a p38-α or p38-β gene or protein, including but not limited to any of those disclosed herein.

In particular embodiments, methods disclosed herein result in a decrease in an expression level or activity of DUX4 and/or one or more DUX4 downstream genes in cells or tissues (e.g., within a subject), e.g., as compared to the expression level or activity in control cells or tissue not contacted with a p38 inhibitor, or a reference level. "Decrease" refers to a decrease of at least 5%, for example, at least 5, 6, 7, 8, 9, 10, 15, 20, 25, 30, 35, 40, 45, 50, 55, 60, 65, 70, 75, 80, 85, 90, 95, 99 or 100%, for example, as compared to the reference level. Decrease also means decreases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of a reference or control cells or tissue.

Methods described herein may be practiced using any type of inhibitor that results in a reduced amount or level of an active p38 protein, e.g., in a cell or tissue, e.g., a cell or tissue in a subject. In particular embodiments, the p38 inhibitor causes a reduction in active p38 protein (e.g., active p38-α and/or p38-β), a reduction in total p38 protein (e.g., total p38-α and/or p38-β protein), a reduction in p38 mRNA (e.g., p38-α and/or p38-β mRNA), and/or a reduction in p38 protein activity (e.g., p38-α and/or p38-β kinase activity) in a cell or tissue contacted with the p38 inhibitor. In particular embodiments, the p38 inhibitor causes a reduction in p38-α and/or p38-β signaling pathway activity or expression. In certain embodiments, the reduction is at least 5%, at least 10%, at least 20%, at least 30%, at least 40%, at least 50%, at least 60%, at least 70%, at least 80%, or at least 90%, as compared to the level in the same type of cell or tissue not contacted with the p38 inhibitor. Methods of measuring total p38 protein or mRNA levels, or p38 kinase activity, in a cell are known in the art. In certain embodiments, the inhibitor inhibits or reduces p38 activity or expression, e.g., mRNA and/or protein expression. In certain embodiments, the inhibitor causes increased degradation of the p38 protein, resulting in lower amounts of p38 protein in a cell or tissue. Particular methods may also employ any type of inhibitor of expression or activity of DUX4 or a DUX4 downstream gene. In certain instances, the inhibitor inhibits both p38-α and p38-β proteins, while in other instances, the inhibitor selectively or preferentially inhibits either p38-α or p38-β. In certain embodiments, the inhibitor does not inhibit p38-γ.

Inhibitors that may be used to practice the disclosed methods include but are not limited to agents that inhibit or reduce or decrease the expression or activity of a biomolecule, (e.g., a protein or nucleic acid), such as but not limited to a p38-α or p38-β gene, mRNA or protein. In certain embodiments, an inhibitor can cause increased degradation of the biomolecule. In particular embodiments, an inhibitor can inhibit a biomolecule by competitive, uncompetitive, or non-competitive means. Exemplary inhibitors include, but are not limited to, nucleic acids, DNA, RNA, gRNA, shRNA, siRNA, modified mRNA (mRNA), microRNA (miRNA), proteins, protein mimetics, peptides, peptidomimetics, antibodies, small molecules, small organic molecules, inorganic molecules, chemicals, analogs that mimic the binding site of an enzyme, receptor, or other protein, e.g., that is involved in signal transduction, therapeutic agents, pharmaceutical compositions, drugs, and combinations of these. In some embodiments, the inhibitor can be a nucleic acid molecule including, but not limited to, siRNA that reduce the amount of functional protein in a cell. Accordingly, compounds or agents said to be "capable of inhibiting" a particular protein, e.g., p38, comprise any type of inhibitor. In certain embodiments, a p38 inhibitor or an inhibitor of DUX4 or a DUX4 downstream target gene is any of the different classes of inhibitors disclosed herein or any other.

In particular embodiments, a p38 inhibitor (or other inhibitor) comprises a nucleic acid that binds to a p38 gene (e.g., MAPK14 or MAPK11 gene) or mRNA (or other target gene or mRNA). Accordingly, a nucleic acid inhibitor may comprise a sequence complementary to a target polynucleotide sequence, e.g., the p38-α sequence disclosed herein, or a region thereof, or an antisense thereof. In particular embodiments, a nucleic acid inhibitor comprises at least 8, at least 10, at least 12, at least 14, at least 16, at least 20, at least 24, or at least 30 nucleotide sequence corresponding to or complementary to a target polynucleotide sequence or antisense thereof.

In certain embodiments, a nucleic acid inhibitor is an RNA interference or anti-sense RNA agent or a portion or mimetic thereof, or a morpholino, that decreases the expression of a target gene when administered to a cell. Typically, a nucleic acid inhibitor comprises at least a portion of a target nucleic acid molecule, or an ortholog thereof, or comprises at least a portion of the complementary strand of a target nucleic acid molecule. In some embodiments, expression of a target gene is reduced by 10%, 25%, 50%, 75%, or even 90-100%.

A "complementary" nucleic acid sequence is a nucleic acid sequence capable of hybridizing with another nucleic acid sequence comprised of complementary nucleotide base pairs. By "hybridize" is meant pair to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152:507).

"Antisense" refers to a nucleic acid sequence, regardless of length, that is complementary to a nucleic acid sequence. In certain embodiments, antisense RNA refers to single stranded RNA molecules that can be introduced to an individual cell, tissue, or subject and results in decreased expression of a target gene through mechanisms that do not rely on endogenous gene silencing pathways. An antisense nucleic acid can contain a modified backbone, for example, phosphorothioate, phosphorodithioate, or others known in the art, or may contain non-natural internucleoside linkages. Antisense nucleic acid can comprise, e.g., locked nucleic acids (LNA).

"RNA interference" as used herein refers to the use of agents that decrease the expression of a target gene by degradation of a target mRNA through endogenous gene silencing pathways (e.g., Dicer and RNA-induced silencing complex (RISC)). RNA interference may be accomplished using various agents, including shRNA and siRNA. "Short hair-pin RNA" or "shRNA" refers to a double stranded, artificial RNA molecule with a hairpin turn that can be used to silence target gene expression via RNA interference (RNAi). Expression of shRNA in cells is typically accomplished by delivery of plasmids or through viral or bacterial vectors. shRNA is an advantageous mediator of RNAi in that it has a relatively low rate of degradation and turnover. Small interfering RNA (siRNA) is a class of double-stranded RNA molecules, usually 20-25 base pairs in length, similar to miRNA, and operating within the RNA interference (RNAi) pathway. It interferes with the expression of specific genes with complementary nucleotide sequences by degrading mRNA after transcription, preventing translation. In certain embodiments, an siRNA is 18, 19, 20, 21, 22, 23 or 24 nucleotides in length and has a 2 base overhang at its 3' end. siRNAs can be introduced to an individual cell and/or culture system and result in the degradation of target mRNA sequences. "Morpholino" as used herein refers to a modified nucleic acid oligomer wherein standard nucleic acid bases are bound to morpholine rings and are linked through phosphorodiamidate linkages. Similar to siRNA and shRNA, morpholinos bind to complementary mRNA sequences. However, morpholinos function through steric-inhibition of mRNA translation and alteration of mRNA splicing rather than targeting complementary mRNA sequences for degradation.

In certain embodiments, a nucleic acid inhibitor is a messenger RNA that may be introduced into a cell, wherein it encodes a polypeptide inhibitor of p38 or other target disclosed herein. In particular embodiments, the mRNA is modified, e.g., to increase its stability or reduce its immunogenicity, e.g., by the incorporation of one or more modified nucleosides. Suitable modifications are known in the art.

In certain embodiments, an inhibitor comprises an expression cassette that encodes a polynucleotide or polypeptide inhibitor of p38 or other target disclosed herein. In particular embodiments, the expression cassette is present in a gene therapy vector, for example a viral gene therapy vector. A variety of gene therapy vectors, including viral gene therapy vectors are known in the art, including, for example, AAV-based gene therapy vectors.

In some embodiments, an inhibitor is a polypeptide inhibitor. In particular embodiments, a polypeptide inhibitor binds to a target polypeptide such as p38, thus inhibiting its activity, e.g., kinase activity. Examples of polypeptide inhibitors include any types of polypeptides (e.g., peptides and proteins), such as antibodies and fragments thereof.

An "antibody" is an immunoglobulin (Ig) molecule capable of specific binding to a target, such as a carbohydrate, polynucleotide, lipid, or polypeptide, through at least one epitope recognition site, located in the variable region of the Ig molecule. As used herein, the term encompasses not only intact polyclonal or monoclonal antibodies, but also fragments thereof, such as dAb, Fab, Fab', F(ab')$_2$, Fv, single chain (scFv), synthetic variants thereof, naturally occurring variants, fusion proteins comprising an antibody portion with an antigen-binding fragment of the required specificity, chimeric antibodies, nanobodies, and any other modified configuration of the immunoglobulin molecule that comprises an antigen-binding site or fragment of the required specificity.

"Fragment" refers to a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids. A "functional fragment" of an antibody is a fragment that maintains one or more activities of the antibody, e.g., it binds the same epitope and or possesses a biological activity of the antibody. In particular embodiments, a functional fragment comprises the six CDRs present in the antibody.

In certain embodiments, the inhibitor induces degradation of a target polypeptide, e.g., p38 protein. For example, inhibitors include proteolysis targeting chimeras (PROTAC), which induce selective intracellular proteolysis of target proteins. PROTACs include functional domains, which may be covalently linked protein-binding molecules: one is capable of engaging an E3 ubiquitin ligase, and the other binds to the target protein meant for degradation. Recruitment of the E3 ligase to the target protein results in ubiquitination and subsequent degradation of the target protein by the proteasome. In particular embodiments, an inhibitor is a PROTAC that targets a p38 protein (e.g., p38-α and/or p38-β).

In certain embodiments, an inhibitor is a small molecule inhibitor, or a stereoisomer, enantiomer, diastereomer, isotopically-enriched, pro-drug, or pharmaceutically acceptable salt thereof. In particular embodiments, the p38 inhibitor inhibits p38-α and/or p38-β. In particular embodiments, it does not significantly inhibit p38-γ. In particular embodiments, a small molecule inhibitor of p38 includes but is not limited to any of the small molecule compounds disclosed herein, including but not limited to those shown in FIG. 12B. A variety of p38 inhibitors are known and available, and some are in clinical development. Any of these may be used. These include, but are not limited to, ARRY-797, VX-745, VX-702, RO-4402257, SCIO-469, BIRB-796, SD-0006, PH-797804, AMG-548, LY2228820, SB-681323 and GW-856553. Illustrative inhibitor compounds also include, but are not limited to:

N-(4-(2-ethyl-4-(m-tolyl)thiazol-5-yl)pyridin-2-yl)benzamide;
2-(2,4-difluorophenyl)-6-(1-(2,6-difluorophenyl)ureido)nicotinamide;
6-(2,4-difluorophenoxy)-8-methyl-2-((tetrahydro-2H-pyran-4-yl)amino)pyrido[2,3-d]pyrimidin-7(8H)-one;
6-(2,4-difluorophenoxy)-2-((1,5-dihydroxypentan-3-yl)amino)-8-methylpyrido[2,3-d]pyrimidin-7(8H)-one;
(R)-6-(2-(4-fluorophenyl)-6-(hydroxymethyl)-4,5,6,7-tetrahydropyrazolo[1,5-a]pyrimidin-3-yl)-2-(o-tolyl)pyridazin-3(2H)-one;
6-(5-(cyclopropylcarbamoyl)-3-fluoro-2-methylphenyl)-N-neopentylnicotinamide;
5-(2-(tert-butyl)-4-(4-fluorophenyl)-1H-imidazol-5-yl)-3-neopentyl-3H-imidazo[4,5-b]pyridin-2-amine;
2-(6-chloro-5-((2R,5S)-4-(4-fluorobenzyl)-2,5-dimethylpiperazine-1-carbonyl)-1-methyl-1H-indol-3-yl)-N,N-dimethyl-2-oxoacetamide;
1-(3-(tert-butyl)-1-(p-tolyl)-1H-pyrazol-5-yl)-3-(4-(2-morpholinoethoxy)naphthalen-1-yl)urea;
4-((5-(cyclopropylcarbamoyl)-2-methylphenyl)amino)-5-methyl-N-propylpyrrolo[2,1-f][1,2,4]triazine-6-carboxamide;
3-(3-bromo-4-((2,4-difluorobenzyl)oxy)-6-methyl-2-oxopyridin-1(2H)-yl)-N,4-dimethylbenzamide;
1-(3-(tert-butyl)-1-(p-tolyl)-1H-pyrazol-5-yl)-3-(5-fluoro-2-((1-(2-hydroxyethyl)-1H-indazol-5-yl)oxy)benzyl)urea;
8-(2,6-difluorophenyl)-2-((1,3-dihydroxypropan-2-yl)amino)-4-(4-fluoro-2-methylphenyl)pyrido[2,3-d]pyrimidin-7(8H)-one;
5-(2,6-dichlorophenyl)-2-((2,4-difluorophenyl)thio)-6H-pyrimido[1,6-b]pyridazin-6-one;

(5-(2,4-difluorophenoxy)-1-isobutyl-1H-indazol-6-yl)((2-(dimethylamino)ethyl)-12-azaneyl)methanone; and
(R)-2-((2,4-difluorophenyl)amino)-7-(2,3-dihydroxypropoxy)-10,11-dihydro-5H-dibenzo[a,d][7]annulen-5-one.

Certain inhibitor compounds of the present invention may exist in stereoisomeric forms (e.g., they may contain one or more asymmetric carbon atoms or may exhibit cis-trans isomerism). Some compounds may include more than one asymmetric carbon atoms. "Stereoisomer" refers to a compound that differ in orientation (R/S) about one or more asymmetric carbon atom(s), or differs in orientation (cis: trans) about a double bond. The term stereoisomer may also encompass atropisomers, which arise from hindered rotation about a single bond, e.g., in compounds having a substituted biphenyl moiety. An "enantiomer" is a compound that is a mirror image of another compound, i.e., all asymmetric carbon atoms of an enantiomer exist in opposite orientation (R/S) with respect to the other compound. A "diastereomer" is a compound that is not a mirror image of another compound, but includes one or more asymmetric carbon atoms existing in opposite orientation (R/S) with respect to the other compound. The embodiments of the present invention may include mixtures of stereoisomers, or may include a single stereoisomer. Single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques. "Isotopically-enriched" refers to a compound wherein one or more atoms is enriched with an isotope beyond its natural abundance. For example, the natural abundance of deuterium is 0.015%. One of ordinary skill in the art recognizes that in all chemical compounds with a H atom, the H atom actually represents a mixture of H and D, with about 0.015% being D. An isotopically-enriched compound may have one or more specific chemical sites wherein the H/D ratio is greater than 0.015%. An isotopically-enriched compound may be referred to as isotopically-labeled.

In certain embodiments, the inhibitor comprises one or more components of a gene editing system. As used herein, the term "gene editing system" refers to a protein, nucleic acid, or combination thereof that is capable of modifying a target locus of an endogenous DNA sequence when introduced into a cell. Numerous gene editing systems suitable for use in the methods of the present invention are known in the art including, but not limited to, zinc-finger nuclease systems, TALEN systems, and CRISPR/Cas systems.

In some embodiments, the gene editing system used in the methods described herein is a CRISPR (Clustered Regularly Interspaced Short Palindromic Repeats)/Cas (CRISPR Associated) nuclease system, which is an engineered nuclease system based on a bacterial system that can be used for mammalian genome engineering. Generally, the system comprises a CRISPR-associated endonuclease (for example, a Cas endonuclease) and a guide RNA (gRNA). The gRNA is comprised of two parts; a crispr-RNA (crRNA) that is specific for a target genomic DNA sequence, and a transactivating RNA (tracrRNA) that facilitates endonuclease binding to the DNA at the targeted insertion site. In some embodiments, the crRNA and tracrRNA may be present in the same RNA oligonucleotide, referred to as a single guide-RNA (sgRNA). In some embodiments, the crRNA and tracrRNA may be present as separate RNA oligonucleotides. In such embodiments, the gRNA is comprised of a crRNA oligonucleotide and a tracrRNA oligonucleotide that associate to form a crRNA:tracrRNA duplex. As used herein, the term "guide RNA" or "gRNA" refers to the combination of a tracrRNA and a crRNA, present as either an sgRNA or a crRNA:tracrRNA duplex.

In some embodiments, the CRISPR/Cas systems comprise a Cas protein, a crRNA, and a tracrRNA. In some embodiments, the crRNA and tracrRNA are combined as a duplex RNA molecule to form a gRNA. In some embodiments, the crRNA:tracrRNA duplex is formed in vitro prior to introduction to a cell. In some embodiments, the crRNA and tracrRNA are introduced into a cell as separate RNA molecules and crRNA:tracrRNA duplex is then formed intracellularly. In some embodiments, polynucleotides encoding the crRNA and tracrRNA are provided. In such embodiments, the polynucleotides encoding the crRNA and tracrRNA are introduced into a cell and the crRNA and tracrRNA molecules are then transcribed intracellularly. In some embodiments, the crRNA and tracrRNA are encoded by a single polynucleotides. In some embodiments, the crRNA and tracrRNA are encoded by separate polynucleotides.

In some embodiments, a Cas endonuclease is directed to the target insertion site by the sequence specificity of the crRNA portion of the gRNA, which may include a protospacer motif (PAM) sequence near the target insertion site. A variety of PAM sequences suitable for use with a particular endonuclease (e.g., a Cas9 endonuclease) are known in the art (See e.g., Nat Methods. 2013 November; 10(11): 1116-1121 and Sci Rep. 2014; 4: 5405).

The specificity of a gRNA for a target locus is mediated by the crRNA sequence, which comprises a sequence of about 20 nucleotides that are complementary to the DNA sequence at a target locus, e.g., complementary to a p38-α or p-38-β DNA sequence. In some embodiments, the crRNA sequences used in the methods of the present invention are at least 90% complementary to a DNA sequence of a target locus. In some embodiments, the crRNA sequences used in the methods of the present invention are at least 95%, 96%, 97%, 98%, or 99% complementary to a DNA sequence of a target locus. In some embodiments, the crRNA sequences used in the methods of the present invention are 100% complementary to a DNA sequence of a target locus, e.g., a MAPK14 or MAPK11 gene. In some embodiments, the crRNA sequences described herein are designed to minimize off-target binding using algorithms known in the art (e.g., Cas-OFF finder) to identify target sequences that are unique to a particular target locus or target gene.

In some embodiments, the endonuclease is a Cas protein or ortholog. In some embodiments, the endonuclease is a Cas9 protein. In some embodiments, the Cas9 protein is derived from *Streptococcus pyogenes* (e.g., SpCas9), *Staphylococcus aureus* (e.g., SaCas9), or *Neisseria meningitides* (NmeCas9). In some embodiments, the Cas endonuclease is a Cas9 protein or a Cas9 ortholog and is selected from the group consisting of SpCas9, SpCas9-HF1, SpCas9-HF2, SpCas9-HF3, SpCas9-HF4, SaCas9, FnCpf, FnCas9, eSpCas9, and NmeCas9. In some embodiments, the endonuclease is selected from the group consisting of C2C1, C2C3, Cpf1 (also referred to as Cas12a), Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. In some embodiments, the Cas9 is a Cas9 nickase mutant. Cas9 nickase mutants comprise only one catalytically active domain (either the HNH domain or the RuvC domain).

In particular aspects, the disclosure includes compositions, e.g., pharmaceutical compositions comprising an inhibitor of p38, including any of the various classes of inhibitors described herein. The invention encompasses pharmaceutical compositions comprising a p38 inhibitor and a pharmaceutically acceptable carrier, diluent or excipient. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the p38 inhibitor against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of a p38 inhibitor. For example, the p38 inhibitor can be in a crystalline form, in amorphous form, and have any particle size. The particles may be micronized, or may be agglomerated, particulate granules, powders, oils, oily suspensions or any other form of solid or liquid physical form.

When p38 inhibitors exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-a-tocopheryl PEG 1000 succinate (20-50%), using complexation such as HP β-CD and SBE β-CD (10-40%), and using advanced approaches such as micelles, addition of a polymer, nanoparticle suspensions, and liposome formation.

p38 inhibitors may also be administered or coadministered in slow release dosage forms. p38 inhibitors may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, syrups, emulsions, oils and the like. For parenteral administration, reconstitution of a lyophilized powder is typically used.

Suitable doses of the p38 inhibitors for use in treating the diseases or disorders described herein can be determined by those skilled in the relevant art. Therapeutic doses are generally identified through a dose ranging study in humans based on preliminary evidence derived from the animal studies. Doses should be sufficient to result in a desired therapeutic benefit without causing unwanted side effects. Mode of administration, dosage forms and suitable pharmaceutical excipients can also be well used and adjusted by those skilled in the art. All changes and modifications are envisioned within the scope of the present patent application.

In certain embodiments, the disclosure includes unit dosage forms of a pharmaceutical composition comprising an agent that inhibits expression or activity of a p38 polypeptide (or results in reduced levels of an active p38 protein) and a pharmaceutically acceptable carrier, diluent or excipient, wherein the unit dosage form is effective to reduce expression of a DUX4 polypeptide, or a polypeptide encoded by a downstream target gene of DUX4, in one or more tissue in a subject to whom the unit dosage form is administered. In certain embodiments, the downstream target gene is MBD3L2, ZSCAN4, LEUTX, PRAMEF2, TRIM43, or KHDC1L. In certain embodiments, the downstream target gene is RFPL2, CCNA1, SLC34A2, TPRX1, KHDC1L, ZSCAN4, PRAMEF20, TRIM49, PRAMEF4, PRAME6, PRAMEF15 or ZNF280A. In certain embodiments, the tissue is muscle tissue. In certain embodiments, the tissue is terminally differentiated, e.g., terminally differentiated muscle tissue. In certain embodiments, the tissue comprises cells comprising a mutation associated with facioscapulohumeral muscular dystrophy (FSHD). In particular embodiments, the agent binds a p38 polypeptide (e.g., p38-α or p38-β) or binds a polynucleotide encoding the p38 polypeptide. In certain embodiments, the agent comprises or consists of: a nucleic acid, optionally a DNA, RNA, modified mRNA (mmRNA), shRNA, siRNA, guide RNA (gRNA), microRNA (miRNA) or antisense oligonucleotide. In other embodiments, the agent comprises or consists of: a polypeptide, optionally a protein, a peptide, a protein mimetic, a peptidomimetic, or an antibody or functional fragment thereof. In other embodiments, the agent comprises: a small molecule, optionally an organic molecule or an inorganic molecule. In other embodiments, the agent comprises a gene expression cassette, optionally a gene therapy vector, that expression a polynucleotide or polypeptide agent that inhibits expression or activity of a p38 polypeptide.

In particular embodiments, the unit dosage forms comprise an effective amount, an effective concentration, and/or an inhibitory concentration, of a p38 inhibitor to treat a disease or disorder associated with increased activity or expression of DUX4 and/or a downstream DUX4 target gene, including any of the disease or disorders disclosed herein, e.g., FSHD.

"Pharmaceutical compositions" include compositions of one or more agents capable of is capable of being administered or delivered to a subject and/or cell for the prevention and/or treatment of a particular disease or disorder.

"Pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, and/or emulsifier which has been approved by the United States Food and Drug Administration as being acceptable for use in humans and/or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations. Except insofar as any conventional media and/or agent is incompatible with the agents of the present disclosure, its use in therapeutic compositions is contemplated. Supplementary active ingredients also can be incorporated into the compositions.

"Effective amount" as used herein refers to an amount of an agent effective in achieving a particular effect, e.g., reducing DUX4-fl mRNA or DUX4 protein, or mRNA or protein of one or more DUX4 downstream targets in a cell, tissue, organ or subject. In the context of therapeutic treatment of a subject, an effective amount may be, e.g., an amount effective or sufficient to reduce one or more disease symptoms in the subject, e.g., a subject with FSHD. In certain embodiments, the reduction is at least 10%, at least 20%, at least 30%, at least 40%, at least 50%, at least 60%, or at least 70%, as compared to the amount prior to or without treatment.

"Effective Concentration" as used herein refers to the minimum concentration (mass/volume) of an agent and/or composition required to result in a particular physiological effect. As used herein, effective concentration typically refers to the concentration of an agent required to increase, activate, and/or enhance a particular physiological effect.

"Inhibitory Concentration" "Inhibitory Concentration" is the minimum concentration (mass/volume) of an agent required to inhibit a particular physiological effect. As used herein, inhibitory concentration typically refers to the concentration of an agent required to decrease, inhibit, and/or repress a particular physiological effect.

In some embodiments, an agent or compound described herein may be administered at a dosage from about 1 mg/kg to about 300 mg/kg. In another embodiment, an agent or compound described herein may be administered at a dosage from about 1 mg/kg to about 20 mg/kg. For example, the agent or compound may be administered to a subject at a dosage of 1, 2, 3, 4, 5, 6, 7, 8, 9, 10, 11, 12, 13, 14, 15, 16, 17, 18, 19 or 20 mg/kg, or within a range between any of the proceeding values, for example, between about 10 mg/kg and about 15 mg/kg, between about 6 mg/kg and about 12 mg/kg, and the like. In another embodiment, an agent or compound described herein is administered at a dosage of ≤15 mg/kg. For example, an agent or compound may be administered at 15 mg/kg per day for 7 days for a total of 105 mg/kg per week. For example, a compound may be administered at 10 mg/kg twice per day for 7 days for a total of 140 mg/kg per week.

In many embodiments, the dosages described herein may refer to a single dosage, a daily dosage, or a weekly dosage. In one embodiment, an agent or compound may be administered once per day. In another embodiment, a compound may be administered twice per day. In some embodiments, an agent or compound may be administered three times per day. In some embodiments, a compound may be four times per day. In some embodiments, an agent or compound described herein may be administered 1, 2, 3, 4, 5, 6, 7, 8, 9, 10, 11, 12, 13, 14, 15, 16, 17, 18, 19, 20, 21, 22, 23, or 24 times per week. In other embodiments, the compound is administered once biweekly.

In some embodiments, an agent or compound described herein may be administered orally. In some embodiments, an agent or compound described herein may be administered orally at a dosage of ≤15 mg/kg once per day.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

The amount and frequency of administration of the compounds of the invention and/or the pharmaceutically acceptable salts thereof will be regulated according to the judgment of the attending clinician considering such factors as age, condition and size of the patient as well as severity of the symptoms being treated.

In some aspects, the present invention relates to methods used for screening to identify drug targets using small molecules and/or genomic tools (e.g., small interfering RNA (siRNA), small hairpin RNA (shRNA), microRNA (miRNA), antisense oligonucleotides and gene therapeutic viruses) that reduce the expression and/or activity of DUX4 and downstream transcripts, MBD3L2, in FSHD myotubes. In particular embodiments, the methods comprise contacting a myotube comprising FSHD cells, for example, cells comprising an FSHD1 and/or an FSHD2 defect (e.g., mutation) with one or more candidate agent, and then determining whether myotubes contacted with the candidate agent have reduced DUX4 activity, reduced levels of DUX4 mRNA or protein, reduced activity of one or more downstream genes regulated by DUX4; or reduced levels of one or more downstream genes regulated by DUX4, as compared to the levels in myotubes contacted with a negative control, e.g., vehicle only. Candidate agents associated with reduced activity or expression levels of DUX4 and/or a DUX4 downstream gene are then identified, and the targets that they modulate may be identified. For example, in the case of siRNA, the gene target of the siRNA associated with reduced expression of DUX4 and/or a DUX4 downstream target gene is identified as a drug target for treating diseases or disorders associated with aberrant expression of DUX4 and/or a downstream DUX4 target gene, including any of those described herein, e.g., FSHD. Similarly, in the case of small molecules, the drug target of the small molecule associated with reduced activity or expression of DUX4 and/or a DUX4 downstream target gene is identified as a drug target for treating diseases or disorders associated with aberrant expression of DUX4 and/or a downstream DUX4 target gene, including any of those described herein, e.g., FSHD. In certain embodiments, the methods may be practiced by assessing a physical or qualitative property of the myotubes, in order to identify a candidate agent and its target, which may be used to improve the physical or qualitative property of the myotubes, thus identifying the target as a therapeutic target for treating diseases or disorders associated with aberrant expression of DUX4 and/or a downstream DUX4 target gene, including any of those described herein, e.g., FSHD.

In certain embodiments, the disclosure includes a method of identifying an agent that inhibits expression of a DUX4 protein, or inhibits expression of a protein encoded by a downstream gene target of DUX4, the method comprising: contacting a myotube prepared from cells associated with facioscapulohumeral muscular dystrophy (FSHD) with a candidate agent; and determining an expression level of the DUX4 protein, a polynucleotide encoding the DUX4 protein, the downstream gene target of DUX4, or a polynucleotide encoding the downstream gene target of DUX4 in the myotube, wherein the candidate agent is identified as an agent that inhibits expression of the DUX4 protein, or the protein encoded by the downstream gene target, if the expression level determined after the contacting is reduced as compared to the expression level of the DUX4 protein or the protein encoded by the downstream gene target in a myotube prepared from cells associated with FSHD not contacted with the candidate agent or contacted with a negative control agent.

In certain embodiments of any of the methods described herein, the candidate agent may be any of the classes of inhibitors disclosed herein, including small molecules, polypeptides, and nucleic acids, such as, e.g., wherein the candidate agent comprises or consists of: a nucleic acid, optionally a DNA, RNA, gRNA, shRNA, miRNA, siRNA, or antisense oligonucleotide; a polypeptide, optionally a protein, a peptide, a protein mimetic, a peptidomimetic, gene therapy vector, or an antibody or functional fragment thereof; or a small molecule, optionally an organic molecule or an inorganic molecule.

In certain embodiments of any of the methods, the downstream target gene is, for example, MBD3L2, ZSCAN4, LEUTX, PRAMEF2, TRIM43, or KHDC1L. In certain embodiments, the downstream target gene is, for example, ZSCAN4, LEUTX, PRAMEF2, TRIM43, MBD3L2, KHDC1L, RFPL2, CCNA1, SLC34A2, TPRX1, PRAMEF20, TRIM49, PRAMEF4, PRAME6, or PRAMEF15.

In certain embodiments, any of the methods described herein are performed by screening a library of potential candidate agents. In certain embodiments, the methods are performed using high throughput assays.

In certain embodiments, the methods are performed using mature patient derived FSHD myotubes.

In one embodiment, a library of small molecules are used to screen for target modifiers of DUX4 or downstream target genes expression or activity in FSHD myotubes. Three days prior to treatment, cells are plated at 15,000 cells per well in a gelatinized 96 well plate with skeletal muscle growth medium (PromoCell, C-23060) with 20% FBS and Pen/Strep (Gibco, 15140148). On the day of treatment, the media is changed to Skeletal Muscle Cell Differentiation Medium (PromoCell, C-23061) supplemented with 20% KnockOut Serum replacement (Gibco, 10828010) or NbActiv4 medium (BrainBits Nb4-500) and Pen/Strep. p38 modulating agents are added at desired concentration into the culture media containing differentiated FSHD myotubes and cultured for 3-4 days in incubator. Myotubes are removed from incubator and RNA is extracted using RNeasy Micro Plus Kit (Qiagen Cat No./ID:74034). cDNA is prepared from the extracted RNA for Taqman Gene Expression assay to measure DUX4 or downstream target genes expression. POL2RA transcript is used as endogenous control.

EXAMPLES

The studies described in the following Examples were performed using the Materials and Methods described below.

Abbreviations
 ASO antisense oligonucleotides
 DAPI 4',6-diamidino-2-phenylindole (dihydrochloride)
 DMSO dimethyl sulfoxide
 DUX4 double homeobox 4
 DUX4-fl double homeobox 4 full length
 FSHD facioscapulohumeral muscular dystrophy
 gRNA guide RNA
 MBD3L2 methyl CpG binding domain protein 3 like 2
 MHC myosin heavy chain
 MPAK14 mitogen-activated protein kinase 14
 mRNA messenger RNA
 MYOG myogenin (myogenic factor 4)
 p HSP27 phosphorylated heat shock protein 27
 PCR polymerase chain reaction
 pLAM polyadenylation signal sequence
 POLR2A RNA Polymerase II Subunit A qPCR quantitative polymerase chain reaction
RNA ribonucleic acid
sgRNA single guide RNA
siRNA small interfering RNA General Materials and Methods Human Skeletal Muscle Myoblasts:

FTCE-00016-01 (immortalized FSDH myoblast line, 6.3 repeats) and isogenic lines, A4 control healthy normal, and C12 FSHD myoblasts were used for all studies (as described in Mamchaoui et al., 2011; Thorley et al., 2016). Four distinct primary patient myoblast lines, FTCE-016, -020, -197, -196 were provided by R. Tawil. The FSHD myoblasts were shown to express aberrant DUX4 via demethylation of the D4Z4 on chromosome 4q35. Media components and tissue culture materials included:

Skeletal Muscle Growth Medium (PromoCell, C-23160) supplemented with 15% FBS (Hyclone, SH30071) and Pen/Strep (Gibco, 15140148). NbActiv4 (BrainBits Nb4-500) and Pen/Strep (Differentiation media). EmbryoMax 0.1% Gelatin Solution (EMDmillipore ES-006-B). PBS (Gibco, 10010023), Tissue culture treated 96-well microplate (Corning, CLS3595),TC-Treated Multiwell Cell Culture Plat (Falcon, 353046). Real Time PCR reagents and kits:

Lysis buffer-Roche Realtime Ready lysis buffer 19.5 µL. (for 20 µL) (Roche, 07248431001), DNAse I (Ambion, AM2222) 0.25 µL, Protector RNase Inhibitor (Roche, 3335402001) 0.25 µL, RNeasy Micro Kit (Qiagen, 74004), Taqman Preamp Master Mix (ThermoFisher Scientific, 4391128), Taqman Multiplex Master Mix (ThermoFisher Scientific, 4484262), ZSCAN4 Taqman Assay (ThermoFisher Scientific, Hs00537549_m1, FAM-MGB), MYOG Taqman Assay (ThermoFisher Scientific, Hs01072232_m1, JUN-QSY), RPLPO Taqman Assay (ThermoFisher Scientific, Hs99999902_m1), and LEUTX Taqman Assay (ThermoFisher Scientific, Hs00418470_m1).

Antisense Oligonucleotides (ASOs):

ASOs were purchased from Exiqon: FTSE-000001 (DUX4 ASO from Exiqon, CAGCGTCGGAAGGTGG (SEQ ID NO:18), 300610)), and non-targeting ASO (Exiqon, AACACGTCTATACGC (SEQ ID NO:19, 300610).

Gelatin Coating of Tissue Culture Dishes:

Performed three days prior to treatment, 0.1% gelatin solution was made by combining 1 g gelatin (e.g. Sigma G9391) and 1 L tissue culture grade water; autoclaved for 30 minutes to dissolve, and sterilized. Sufficient 0.1% gelatin to coat dish was applied using a sterile pipette, then the solution was aspirated, and the dishes were air-dried and stored at room temperature.

Cell Plating:

Performed three days prior to treatment, 10,000 cells were plated per well on gelatinized 96-well plates, or 100,000 cells on gelatinized 6-well plates.

Antisense Oligonucleotide and Compound Treatment:

For ASO or compound treatments, cells were plated into 100 µL of Promocell growth medium containing ASO or compounds at the described concentrations.

Skeletal Muscle Myotube Differentiation:

On day 0, the media was changed to differentiation media. Plates were removed from the incubator and the growth medium was aspirated, plates were washed once with PBS, 100 µL, for 96-wells and 1 mL for a 6-well plate, 100 µL, or 2 mL of differentiation medium was added per well, 96- or 6-well respectively. Antisense oligonucleotides or drug were added at the desired concentration, and the plates were put back in the incubator and incubated for 3-4 days.

RNA Preparation:

Cells were removed from the incubator and media aspirated. Cells were quickly lysed following one of the following protocols: for lysis in 96-well plates, direct lysis and one-step RT-Preamp qPCR was performed according to the protocol described below. For each 96-well, a mix containing: 19.5 µL Roche Realtime Ready lysis buffer, 0.25 µL RNAse inhibitor, 0.25 µL DNAseI (from Thermo not the included one in the kit) was prepared. 20 µL of the mix was added to each well, mixed 5 times, and incubated 5 minutes at RT or alternatively shaken vigorously for 15 minutes. Lysis was observed under the microscope. Samples were frozen −80° C. at least for 15 minutes.

qPCR One Step:

For qPCR, cell lysate was diluted 1:10, and 2 µL was used for a 10 µL 1-step RT-qPCR reaction for detection of GAPDH, RPLPO, TBP, MYOG, FRG1, MYH3, ACTN2, etc. Per 10 µL reaction, the reaction mix included: 2 µL of RNA (1:10 dilution lysate), 5 µL of Fast Advanced Taqman Master Mix (2×), 0.25 µL of RT enzyme mix (40×), 0.5 µL of Taqman probe set (20×), and 2.25 µL of $H_2O$. The following reaction protocol was run on the QuantStudio 7: 48° C. for 15 min, 50° C. for 2 min, 95° C. for 30 sec, 40×, 95° C. for 5 sec, 60° C. for 30 sec, after which the plates were read as specified by the manufacturer (Thermo).

1-step RT-Preamplification was used for detection of DUX4 downstream genes, i.e., MBD3L2, ZSCAN4, LEUTX, TRIM43, KHDC1L, and POL2RA-VIC was used as endogenous control. Per 10 µL reaction, the reaction mix included: 2.25 µL of RNA (1:10 dilution lysate), 5 µL of Taqman Pre-Amp Master Mix (2×), 0.25 µL of RT enzyme mix (40×), 2.5 µL of Taqman probe set (0.2×)*. * For pooling the TaqMan Assays, equal volumes of each 20× TaqMan® Gene Expression Assay were used, and up to 100 assays were combined. For example, to pool 50 TaqMan assays, 10 µL of each assay were combined in a microcentrifuge tube. The pooled TaqMan assays were diluted using 1× TE buffer so that each assay was at a final concentration of 0.2×. For the above example, 500 µL of 1× TE buffer was added to the pooled TaqMan assays for a total final volume of 1 mL. The QuantStudio7 protocol was used at 48° C. 15 min, 95° C. 10 min, 10 cycles: 95° C. 15 sec, 60° C. 4 min, and 4° C. infinite Samples were then diluted to 50 µL and continued with the qPCR step. Per 10 µL reaction, the reaction mix included: 2 µL of Preamp dilution, 5 µL of Fast Advanced Taqman Master Mix (2×), 0.5 µL of Taqman probe set (20×), and 2.5 µL of $H_2O$. When multiplexing, the volume was adjusted to 10 µL total. The following program was run on the QuantStudio7: 50° C. for 2 min, 95° C. for 30 sec, 40×, 95° C. for 5 sec, 60° C. for 30 sec, and plates were read as per the manufacturers specifications (Thermo).

Methods for Total RNA Extraction from Myotubes Using RNeasy Micro Plus Kit:

In a 6 well plate, 450 µL Buffer RLT Plus was added. Lysate was homogenized by transfer of the lysate to a gDNA Eliminator spin column placed in a 2 mL collection tube (supplied), the column was centrifuged for 30 s at ≥8000×g (≥10,000 rpm), and then the column was discarded while saving the flow-through. 250 µL of ethanol (35% final) was added to the flow-through, and mixed well by pipetting (not centrifuged). The samples were then transferred, including any precipitate that may have formed, to an RNeasy MinElute spin column placed in a 2 mL collection tube (supplied). The columns were centrifuged for 15 s at ≥8000×g. Flow-through was discarded or collected for protein precipitation. 700 µL of Buffer RW1 was added to the RNeasy MinElute spin column, which was then centrifuged for 15 s at ≥8000×g, after which the flow-through was discarded.

DNAse treatment was performed by gently mixing 10 μL DNAseI with 70 μL of Buffer RDD, and the resulting solution was added directly to the column, which was incubated at room temperature for 20 min. Then, 700 μL of Buffer RW1 (per manufactures specification) was added to the RNeasy MinElute spin column, the column was centrifuged for 15 s at ≥8000×g. and the flow-through discarded. 500 μL Buffer RPE was added to the RNeasy MinElute spin column, which was then centrifuged for 15 s at ≥8000×g, after which the flow-through was discarded. 500 μL of 80% ethanol was added to the RNeasy MinElute spin column, the column was centrifuged for 2 min at ≥8000×g to wash the spin column membrane, and the collection tube was discarded with the flow-through. The RNeasy MinElute spin column was placed in a new 2 mL collection tube (supplied), centrifuged at full speed for 5 min to dry the membrane, and the collection tube was discarded with the flow through. The RNeasy MinElute spin column was placed in a new 1.5 mL collection tube (supplied). 14 μL of RNase-free water was added directly to the center of the spin column membrane, which was then centrifuged for 1 min at full speed to elute the RNA. Approximately 12 μL of RNA was eluted.

Detection of DUX4-fl Using Method Described by Himeda et al. 2015:

cDNA preparation. 10 μL reactions included 1 μL of RNA (1 μg), 0.5 μL of Oligo dT, 0.5 μL of 10 mM dNTPs, and 4.5 μL of $H_2O$. Reaction samples were incubated at 65° C. for 2 min and quickly moved to ice and held at least 1 min before adding the enzyme mix, which included 2 μL of 5× First strand Buffer, 0.5 μL of 0.1M DTT, 0.5 μL of RNAse inhibitor, 0.5 μL of SSIV RT. The samples were incubated at 55° C. for 20 min and 80° C. for 10 min, followed by cool down to 4° C. DUX4 pre-amplification was performed in a 10 μL reaction mixture containing 1 μL of RT reaction, 2 μL of 5× GC buffer, 0.8 μL of DMSO, 0.2 μL of 10 mM dNTPs, 0.2 μL of 10 μM TJ38F, 0.2 μL of 10 μM TJ40R, 0.1 μL of Phusion II DNA pol, and 5.5 μL of $H_2O$. The following protocol was run on the QuantStudio 7: 98° C. 2 min, 10 cycles of 98° C. 15 seconds, 64° C. 20 seconds, 72° C. 15 seconds, and 4° C. infinite.

DUX4 qPCR with nested primers was performed in a 10 μL reaction containing 1 μL of DUX4 pre amplification DNA, 5 μL of 2× IQ SYBR Mix, 0.4 μL of 10 μM TJ38F, 0.4 μL of 10 μM TJ41R, and 3.2 μL $H_2O$. The following protocol was run on the QuantStudio7: 95° C. 3 min, 40 cycles of 95° C. 10 seconds, 64° C. 15 seconds, 72° C. 20 seconds, 86° C. 10 seconds, then the plates were read on QuantStudio7 as per manufactures instruction (Thermo). Ct values were extracted from the QuantStudio Realtime PCR software, and Genedata was used to calculate relative levels of expression using POLR2A as a housekeeping gene.

RNAseq Methods:

The 40 bp single-end reads from Illumina had good quality by checking with FastQC (http://www.bioinformatics.babraham.ac.uk/projects/fastqc/). Reads were mapped to hg19 using TopHat v2.1.1 (Kim et al., 2013) with options as "solexa1.3-quals" mode and "no-novel-juncs." The gene model for TopHat was created by merging known gene in gtf format with kgXref table. Both known gene and kgXref were downloaded from UCSC table browser in hg19 assembly. The read counts were obtained using featureCounts function from Subread package with strandness option as –r 2. Reads were normalized with DESeq2 (Love et al., 2014).

FSHD Myotube Immunocytochemistry:

Briefly, cells were fixed in 4% paraformaldehyde and permeabilized in 4% paraformaldehyde (PFA) for 10 min at room temperature. Cells were permeabilized with PBST (1× PBS solution with 0.1% Triton X-100) before blocking with 10% Normal Donkey Serum or 3% BSA (NDS) in PBST. Cells were then incubated with appropriately diluted primary antibodies in PBST with 5% NDS for 1 hours at room temperature or 12 hours at 4° C., washed with PBST for 3 times at room temperature, and then incubated with desired secondary antibodies in TBST with 5% NDS and DAPI to counterstain the nuclei. DUX4 was detected by immunocytochemistry using the E5-5 antibody in differentiated FSHD myotubes. Activated Caspase-3 was detected using a commercially available antibody (https://www.cellsignal.com/products/primary-antibodies/cleaved-caspase-3-asp175-antibody/9661).

RNAseq Methods:

The 40 bp single-end reads from Illumina had good quality by checking with FastQC (http://www.bioinformatics.babraham.ac.uk/projects/fastqc/). Reads were mapped to hg19 using TopHat v2.1.1. The gene model for TopHat was created by merging knownGene in gtf format with kgXref table. Both known gene and kgXref were downloaded from UCSC table browser in hg19 assembly. The read counts were obtained using feature Counts function from Subread package with strandness option as -r 2. Reads were normalized with DESeq2. The biological replicates in the neuron samples, processed at different time periods, had batch effect as suggested by principle component analysis. Consequently, Combat was used for reducing this batch effect. Calculated standard RPKM expression values. Total gene signature was very small and defined at standard statistical cutoffs: 86/19,799 mRNA genes. DUX4-regulated gene signature was a majority of total signature: 77/86 mRNA genes=90%. Non-DUX4 regulated genes was a minority of total signature with moderate fold changes: 9/86 mRNA genes=10%; 2–2.7×log FC.

Methods for siRNA and Cas9/sgRNA RNP Transduction of FSHD Myotubes:

Synthetic crRNAs were purchased from Thermo Fisher Scientific and annealing to tracrRNAs was performed according to specifications. In short, crRNAs and tracrRNA were resuspended in TE buffer at 100 μM, mixed, and diluted 5-fold in annealing buffer. Annealing was performed in a ProFlex PCR system following manufacturer's recommendation. 100 ng of assembled crRNA:tracrRNA were incubated with 500 ng of TrueCut Cas9 (ThermoFisher, #A36497) in the resuspension buffer provided with the Neon transfection system kit (ThermoFisher, #MPK10096). After 15 minute incubation, the reaction was used to transfect 50,000 myoblasts according to the methods described. Sequences used for the targeting of MAPK14 (3 sgRNAs) and pLAM region (polyadenylation sequence of DUX4, 4 gRNAs) were: NT-CTRL, GTATTACTGATATTGGTGGG (SEQ ID NO:8); MAPK14, GCTGAACAAGACAATCTGGG (SEQ ID NO:9), CTGCTTTTGACACAAAAACG (SEQ ID NO:10), CTTATCTACCAAATTCTCCG (SEQ ID NO:11); pLAM, AGAATTTCACGGAAGAACAA (SEQ ID NO:12), CAGGTTTGCCTAGACAGCGT (SEQ ID NO:13), ATTAAAATGCCCCCTCCCTG (SEQ ID NO:14), AATCTTCTATAGGATCCACA (SEQ ID NO:15), and siRNA MAPK14, Antisense: UAGAUUACUAGGUUUUAGGTC (SEQ ID NO:16), Sense: CCUAAAACCUAGUAAUCUAUU (SEQ ID NO:17).

In Vivo Materials and Methods

Rats for PK/PD Studies:

Male Sprague Dawley rats (6-8 weeks of age) were supplied by Hilltop Lab Animals, Inc. (USA). Following arrival at Wuxi AppTec, animals were assessed for their general health by a member of veterinary staff or other designated personnel. Animals were acclimated for at least 2 days (upon arrival at WuXi AppTec) before commencement of the study. Animals were individually housed during acclimation and throughout the study. The animal room environment was controlled according to facility operation (target conditions: temperature 20 to 26° C., relative humidity 30 to 70%, 12-hour cycle of lights on and off). Lights, temperature and relative humidity are constantly monitored by AmegaView Environmental Monitoring System. The diet (Certified Rodent Diet #5002, PMI Feeds, Inc., Brentwood, Mo.) was irradiated pellets with double package; diet lot number and specifications will be recorded in study notebook and archived at WuXi AppTec. Water (reverse osmosis) was provided to the animals ad libitum. Periodic analyses of water quality were performed, and the results were archived at WuXi AppTec. There are no known contaminants in the diet or water that, at the levels of detection, is expected to interfere with the outcome of the study. In study #FULTH-20171120 rats were fasted overnight prior to drug administration: rats were allowed free access to water at all times and were fed 4 hours post dosing. For study #FULTH-20171228 rats were allowed ad-libitum access to food and water throughout the study.

Mice for Xenograft Studies:

Male NOD.Cg-Rag1tm1Mom Il2rgtm1Wj1/SzJ (Nod-Rag) mice (6-8 weeks of age) were supplied by the University of Maryland VR breeding colony (USA). Animals were housed in the UMB central animal facility at Howard Hall at the University of Maryland. Animals were group housed (4/cage) during acclimation (4-5 days), throughout the engraftment procedure and throughout the drug treatment study. The animal room environment was controlled according to facility operation (target conditions: temperature 20 to 26° C., relative humidity 30 to 70%, 12-hour cycle of lights on and off). Lights, temperature and relative humidity are constantly monitored by AmegaView Environmental Monitoring System. The diet (LabDiets 5P76 22.5% protein rodent chow) was provided ad libitum during the study. Sterilized water was provided ad libitum. There are no known contaminants in the diet or water that were expected to interfere with the outcome of the study.

Creation of FSHD and Control Xenograft Mice:

FSHD and control mice were generated by xenografting C6 and A4 IPSC-derived human immortalized isogeneic myoblast cell lines into the bilateral tibialis anterior (TA) muscles of approximately 8-week old male Nod-Rag mice. To create the human muscle xenografts, a niche to seed the A4 or C6 cells within the TA of the mouse hindlimb was created by X-irradiating the hindlimbs of the 8-week-old immunodeficient NRG mice, to prevent mouse muscle regeneration. One day later, 50 ul of a 2% BaCl2 solution was injected along the length of each TA to eliminate the mouse muscle tissue. Following mouse tissue ablation, $2 \times 10^6$ C6 cells were injected into each, bilateral, TA region and allowed to develop for four weeks. Following engraftment of the A4 or C6 cells, the animals were exposed to 4 weeks of intermittent neuromuscular electrical stimulation (iNMES) in order to improve the engraftment of the human cells as described by Sakellariou et al., 2016.

Test Article Formulation and Preparation

Appropriate amount of FTX-1821 were accurately weighed and mixed with appropriate volume of excipients (0.5% (1% DMSO:99% methyl cellulose) in water to get a uniform suspension with a final concentration of 0.03 mg/mL. Formulation was prepared on the day of the study and was dosed within 1 hour of preparation. Dose volume given to animals was 10 mL/kg. Two 20-50 µL aliquots of dose solution were taken from each formulation and set aside for the determination of dose accuracy by LC-MS/MS.

Appropriate amount of FTX-2865 were accurately weighed and mixed with appropriate volume of sterile 0.9% saline for injection to achieve a clear solution with a final concentration 1 mg/mL. Formulation was prepared on the day of the study and was given to animals using a dose volume of 10 mL/kg.

FTX-1821 Test Article Administration and PK/PD Study Design

The dosing solution of FTX-1821 (0.03 mg/mL) was administered via oral gavage at a dose volume of 10 mL/kg in order to yield a final dose of 0.3 mg/kg. following Wuxi facility SOPs. Dose volume was determined by measured body weight prior to dosing. The dosing solution concentrations (mg/ML), dose volumes (mL/kg) and final dose (mg/kg) for the respective treatment groups were recorded in the included excel study sheet. Feeding condition: overnight fast, food return 4 hours after dosing.

FTX-2865 Test Article Administration and Xenograft Study Design

The dosing solution of FTX-2865 (1 mg/mL) was administered via IP injection at a dose volume of 10 mL/kg in order to yield a final dose of 10 mg/kg (for each dose). 0.9% sterile saline was administered via IP injection at a dose volume of 10 mL/kg as a vehicle control (for each dose). Dose volume was determined by measured body weight prior to the morning dosing. The dosing solution concentrations (mg/ML), dose volumes (mL/kg) and final dose (mg/kg) for the respective treatment groups were recorded in the included excel study sheet. BID injections were spaced approximately 12-hours apart to maximize target coverage. Study animals received a total of 14 injections of vehicle or FTX-2865 over 8 days and were sacrificed approximately 1-hour after the final morning injection on day 8.

Sample Collection:

Blood samples for PK: Approximately 100 µl of blood sample was obtained via jugular vein or tail vein at each pre-defined time point. Blood samples were placed in pre-chilled collecting tubes treated with EDTA-K2 as anti-coagulant and placed on ice until centrifugation.

Plasma collection for PK assessment: PK blood samples were centrifuged at 4° C., 3000 g for 15 min within half an hour for plasma collection. Plasma samples were stored in polypropylene tubes or 96-well plates, quickly frozen on dry ice and stored at −70° C. until LC/MS/MS analysis.

Muscle collection for PK and PD assessment: Bilateral tibialis anterior and trapezius muscles were collected following blood collection by cardiac puncture. Each muscle from left and right sides was quickly weighed separately and placed in separate tubes, then snap frozen on dry ice. Muscles from one side were used for the measurement of compound concentration, those from the other side were sent to the sponsor for PD analysis. Dosing was staggered so that sample collection was carried out at approximately the same time at the end of the day.

Sample Processing for PK Analysis:

Plasma Sample Preparation for LC/MS Analysis: An aliquot of 10 µL plasma sample was protein precipitated with 150 µL IS solution (100 ng/mL Labetalol & 100 ng/mL Tolbutamide & 100 ng/mL Diclofenac in ACN), the mixture was vortex-mixed well and centrifuged at 4000 rpm for 15 min, 4° C. An aliquot of 80 µL supernatant was transferred to sample plate and mixed with 80 µL water, then the plate was shaken at 800 rpm for 10 min. 1 µL supernatant was then injected for LC-MS/MS analysis. Muscle sample preparation for LC/MS Analysis: The muscle samples were homogenized in water in a 1:4 ratio (w/v) using Omni bead ruptor. The homogenates were then used for the measurement of drug concentration. An aliquot of 20 μL muscle tissue homogenate was protein precipitated with 200 μL IS solution (100 ng/mL Labetalol & 100 ng/mL Tolbutamide & 100 ng/mL Diclofenac in ACN), the mixture was vortex-mixed well and centrifuged at 4000 rpm for 15 min, 4° C. An aliquot of 80 μL supernatant was transferred to sample plate and mixed with 80 μL water, then the plate was shaken at 800 rpm for 10 min. 0.3 μL supernatant was then injected for LC-MS/MS analysis.

Analytical Method (LC/MS, Non-GLP):

Technical details used to execute analytical methods include: Instrument: LCMS Triple Quad QTRAP 6500+ (SCIEX, MA, USA), Matrix:Male SD rat plasma (EDTA-K2), Internal standard(s):100 ng/mL Labetalol & 100 ng/mL Tolbutamide & 100 ng/mL and Diclofenac in CAN, MS conditions ESI: positive, SRM detection of FTX-1821: [Mouse+Human]+m/z 383.838>299.231; Labetalol (IS): [M+H]+m/z 329.2/162.1;Tolbutamide (IS): [M+H]+m/z 271.1/155; Calibration curve: 1.00-3000 ng/mL for FTX001821-02 in male SD rat plasma (EDTA-K2) and muscle homogenate Quantitation method: The peak area of the test article in samples and in the standard solution sample was determined by LC/UV or LC-MS/MS method. Method acceptance criteria: Linearity: ≥75% STDs was back calculated to within ±20% of their nominal values (±25% for LLOQ) in biofluid and within 25% of their nominal values (30% for LLOQ) in tissue homogenate and feces sample. QC: ≥67% all QCs was back calculated to within ±20% of their nominal values for biofluid and within 25% of their nominal values for tissue and feces samples. Specificity: The mean calculated concentration of analyte in the single blank matrix was less than 0.5 times of the LLOQ. Sensitivity: The LLOQ in biofluid and tissue homogenate was 1-3 ng/mL. Carryover: The mean calculated carryover concentration in the single blank matrix immediately after the highest standard injection was less than LLOQ.

Protocol for Cryofracture, Lysis and Preparation of Muscle Tissue for Immunoassay Assessment of Target Engagement:

Approximately 50 mg of muscle tissue was placed on dry ice. Muscle samples were cut, as needed to obtain the 50 mg weight using a clean razor blade per specimen. 50 mg of muscle tissue was placed into a pre-labeled TT1 Covaris bag (Covaris, MA, USA) and kept on dry ice. The TT1 Covaris bag was submerged in liquid nitrogen and the sample was cryofractured in the Covaris cryoPREP (Covaris, MA, USA) on setting "5". The TT1 bag was rotated 180° and steps 2-a were repeated. The sample was transferred into a pre-weighed/labeled tube and maintained on dry ice until all samples were prepared. Sample weights were recorded. RIPA lysis buffer was prepared (R0278-500ML, Sigma, MO, USA). For 10 ml, two Roche PhosSTOP phosphatase inhibitor tablets and one Roche EDTA-free protease inhibitor tablet were added. To the cryofractured material, 8 μl per mg of RIPA buffer were added to each tube and each tube was vortexed until the lysate was homogeneous. Lysates were maintained on ice until all samples were processed. The lysate was cleared by centrifugation at 13,000 g for 5 minutes at 4° C. The supernatant was transferred to a new tube and snap frozen in liquid nitrogen (setting aside 100 for protein assay). To measure the protein content of each sample, a Bradford DC protein assay (5000112, Bio-Rad, CA, USA) was conducted. Samples were diluted 1:20 in PBS for protein assessment.

Phospho MK2 and Total MK2 Immunoassay:

The homogenized trapezius muscle lysate was assessed using an internally developed Meso Scale Discovery (MSD) multiplexed phospho MK2/total MK2 immunoassay (Meso Scale Diagnostics, MD, USA). For each sample, 50 μL of muscle lysate, equal to 50 μg of protein, was loaded onto the MSD assay. Protein concentrations in muscle lysates were determined by a Bradford DC protein assay as described above. Samples were assessed in duplicate. Muscle samples were incubated on a pre-coated MSD plate overnight at 4° C. while on an orbital shaker (300 rpm) and assessed the following morning.

Protocol for Cryofracture, RNA Extraction and RNA Purification of Muscle Tissue and Quantitative PCR Assay Assessment of MBD3L2 and CDKN1B:

Approximately 3-5 mg of TA muscle tissue was placed on dry ice. Muscle tissue was placed into a pre-labeled TT1 Covaris bag (Covaris, MA, USA) and kept on dry ice. The TT1 Covaris bag was submerged in liquid nitrogen and the sample was cryofractured in the Covaris cryoPREP (Covaris, MA, USA) on setting "5". The TT1 bag was rotated 180° and steps 2-a were repeated. The sample was transferred into a pre-weighed/labeled tube and maintained on dry ice until all samples were prepared. RNA was purification using Zymo Direct-zol microprep RNA kit (CA, USA) from 3-5 mg of cryofractured muscle tissue. cDNA was synthesized from the RNA template via reverse transcription. The targeted transcripts were then pre-amplified in a 14-cycle PCR assay using diluted, human-specific TaqMan probes. Gene expression was analyzed in a qPCR assay using the human specific TaqMan probes. The relative expression level was normalized to CDKN1B expression using $2^{\Delta Ct}$ method.

Data Analysis:

Plasma and muscle concentration versus time were analyzed by non-compartmental approaches using the Phoenix WinNonlin 6.3 software (Cetera, NJ, USA). C0, CLp, Vdss, Cmax, Tmax, T½, AUC(0-t), AUC(0-inf), MRT(0-t), MRT (0-inf), % F and graphs of plasma and muscle concentration versus time profile and PD endpoints are reported using GraphPad Prizm software version 7 (CA, USA). Muscle PD was assessed via one-way ANOVA using GraphPad Prizm software version 7 (CA, USA). The effect of C6 vs. A4 cell engraftment on MBD3L2 mRNA in xenografted muscles was assessed via two-tailed T-test using GraphPad Prizm software version 7 (CA, USA). The effect of FTX-2865 vs. vehicle treatment on MBD3L2 mRNA in FSHD xenografted muscles was assessed via two-tailed T-test using GraphPad Prizm software version 7 (CA, USA).

Example 1

Repression of DUX4 Using Sequence Directed Antisense Oligonucleotide Reduces Downstream Target Genes Wild type myotubes were treated with DMSO control vehicle, and mature patient-derived FSHD myotubes that express DUX4 protein were treated with DMSO vehicle control or 1 μM of a DUX4 sequence-directed antisense oligonucleotide (ASO; FTX-2) purchased from Exiqon. After treatment, the myotubes were lysed in 19.5 μL of Roche Real Time Ready Lysis Buffer, 0.25 μL of DNAse1 (Ambion, AM2222), 0.25 μL of Protector RNase Inhibitor (Roche, 3335402001), and the RNA was collected in an RNeasy Micro Kit Master Mix. Expression levels of DUX4-regulated downstream genes (ZSCAN4, TRIM43, MBD3L2, LEUTX, and KHDC1L) was determined by real time PCR (ThermoFisher Scientific, 4484262), ZSCAN4

Taqman Assay (ThermoFisher Scientific, Hs00537549_m1, FAM-MGB), MYOG Taqman Assay (ThermoFisher Scientific, Hs01072232_m1, JUN-QSY), RPLPO Taqman Assay (ThermoFisher Scientific, Hs99999902_m1), and/or LEUTX Taqman Assay (ThermoFisher Scientific, Hs00418470_m1). Ct values were extracted from QuantStudio Realtime PCR software, and Genedata was used to calculate relative levels of expression using POLR2A as a housekeeping gene.

Figure 2:
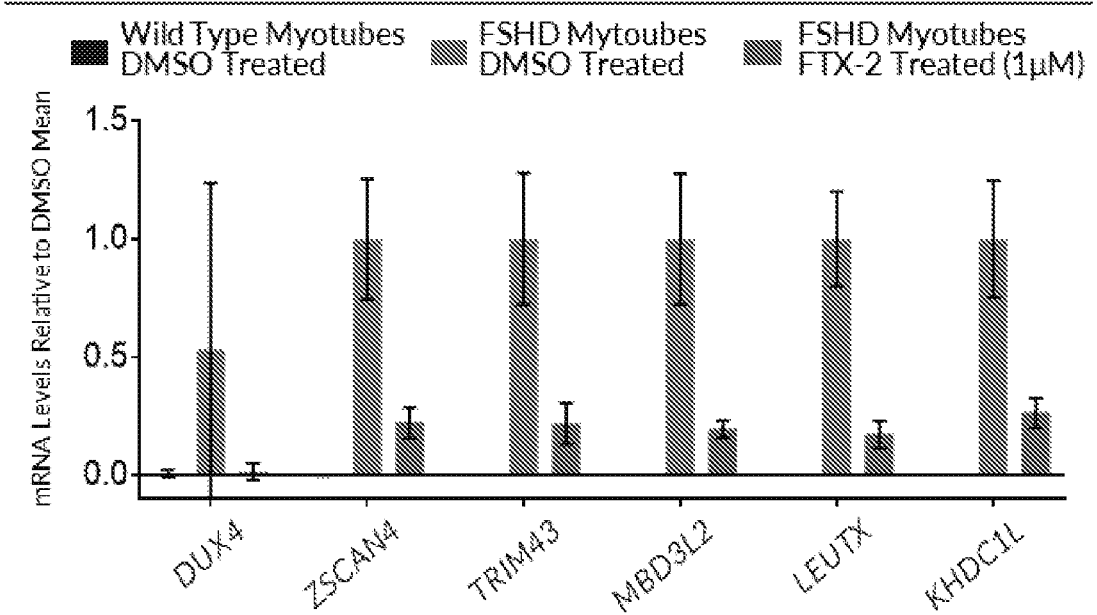
FIG. 2 is a graph showing mRNA expression of the indicated DUX4 regulated genes in wild type myotubes treated with DMSO, or FSHD myotubes treated with FTX-2 or DMSO. For each indicated gene, the bars from left to right correlate to wild type myotubes treated with DMSO, FSHD myotubes treated with DMSO, and FSHD myotubes treated with FTX-2 (DUX4-targeted ASO).

The results showed that FSHD myotubes treated with DUX4 sequence directed ASO express reduced amounts of DUX4 and the DUX4 downstream transcription factor target genes, ZSCAN4, TRIM43, MBD3L2, LEUTX, and KHDC1L, as compared to FSHD myotubes treated with DMSO vehicle control (FIG. 2).

Figure 3A:
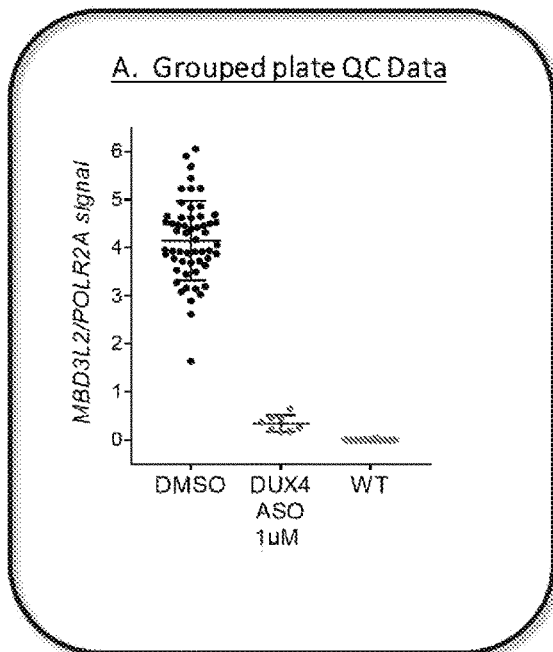
FIGS. 3A-3C show reduction of MBD3L2 mRNA in FSHD myotubes treated with DUX4-targeted ASOs. MBD3L2 was normalized to POLR2A mRNA as measured by qPCR.
Figure 3B:
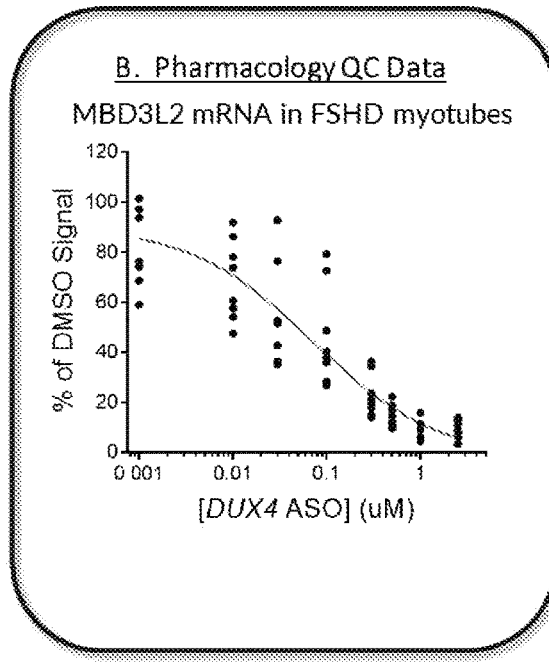
Figure 3C:
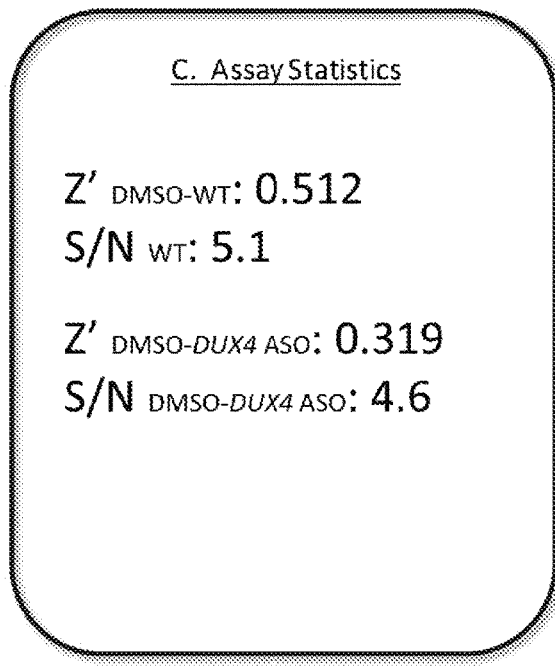

The data in FIG. 3A are grouped plate quality control data comparing expression of MBD3L2 mRNA in FSHD myotubes treated with DMSO control or 1 μM DUX4 ASO, and healthy normal isogenic control myotubes. FIG. 3B shows pharmacologic quality control data and dose dependent reduction of DUX4 and the downstream gene, MBD3L2, using different dilutions of the DUX4 ASO. FIG. 3C shows plate-based assay statistics comparing FSHD myotubes treated with DMSO to WT: Z' is 0.512 and Signal to Noise (S/N) is 5.1, and FSHD myotubes treated with DMSO or DUX4 ASO: Z' is 0.319 and Signal to Noise (S/N) is 4.6.

Example 2

P38 Small Molecule Inhibitors Reduce MBD3L2 mRNA Expression

Figure 4A:
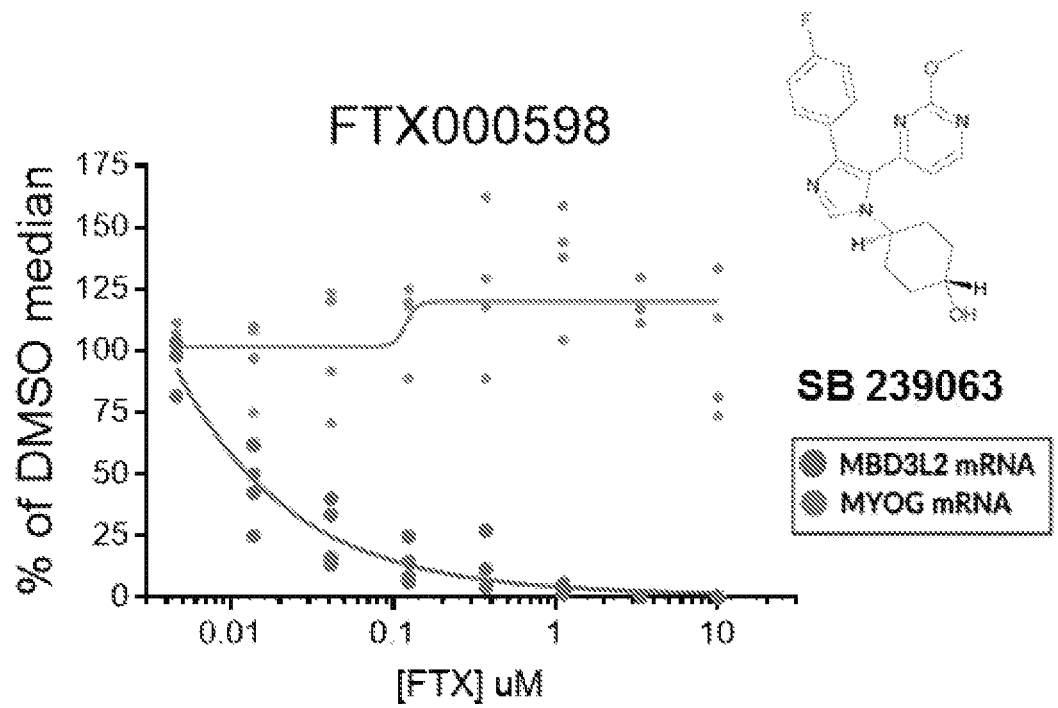
FIGS. 4A-4D are graphs showing expression levels of MBD3L2 mRNA and MYOG mRNA in FSHD myotubes treated with the indicated p38α/β inhibitors relative to treatment with DMSO control. The p38α/β inhibitors included SB 239063 (FIG. 4A), VX-702 (FIG. 4B), Pamapimod (FIG. 4C), and TAK-715 (FIG. 4D). The structures of the inhibitors are also provided.
Figure 4B:
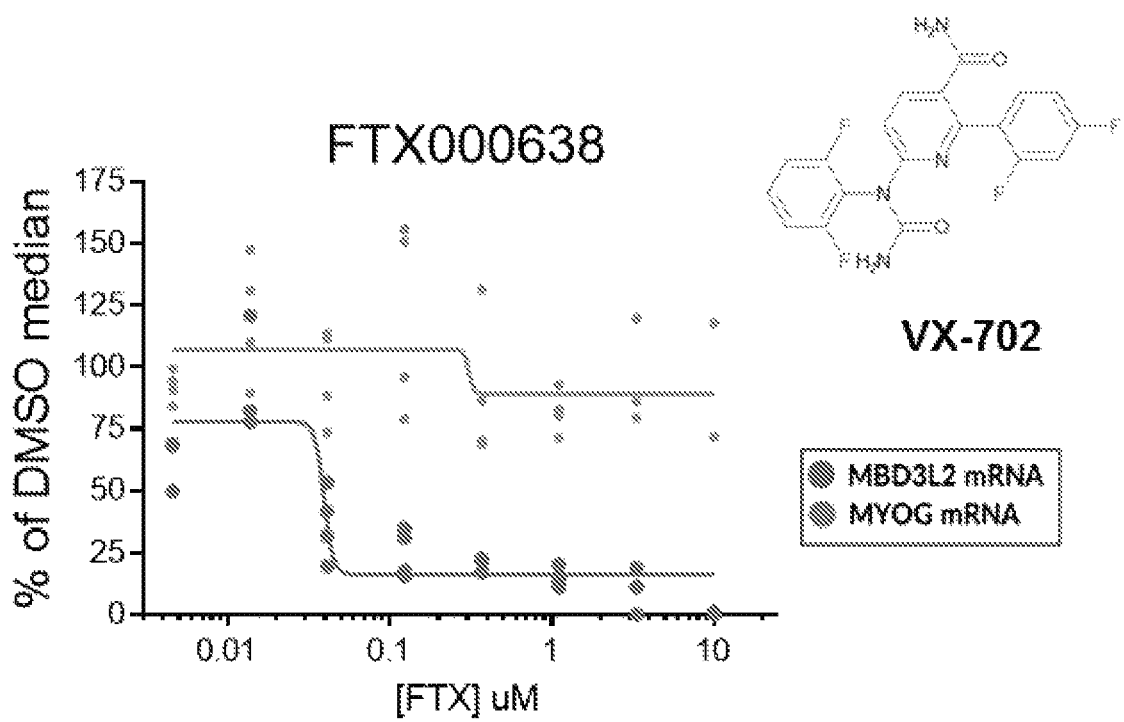
Figure 4C:
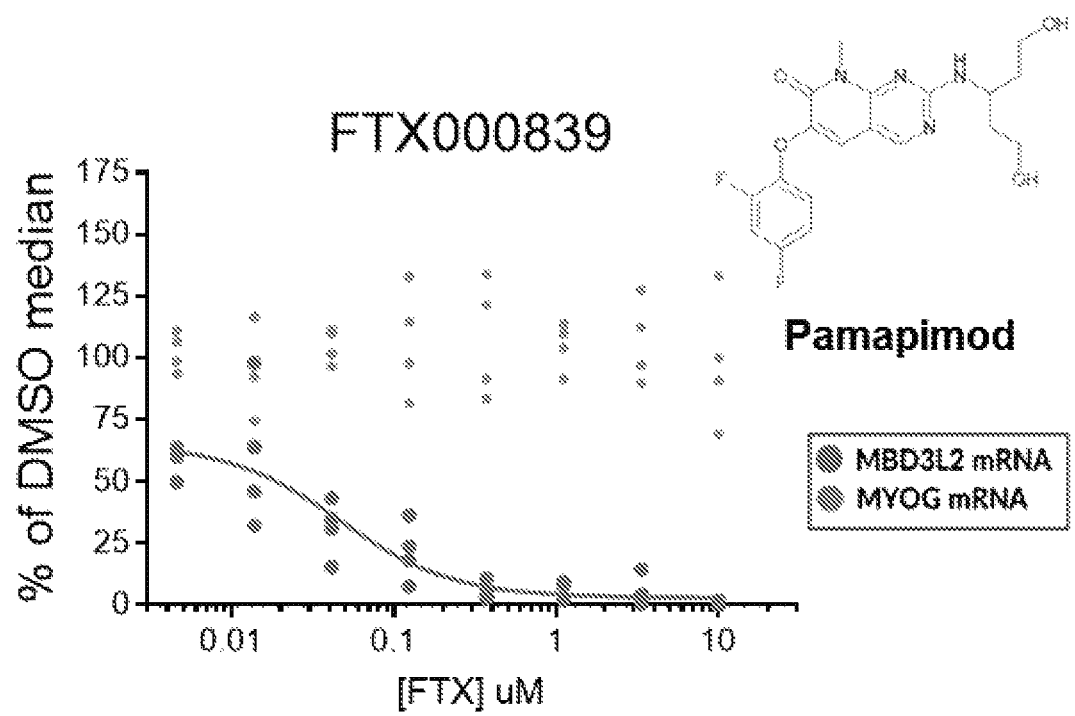
Figure 4D:
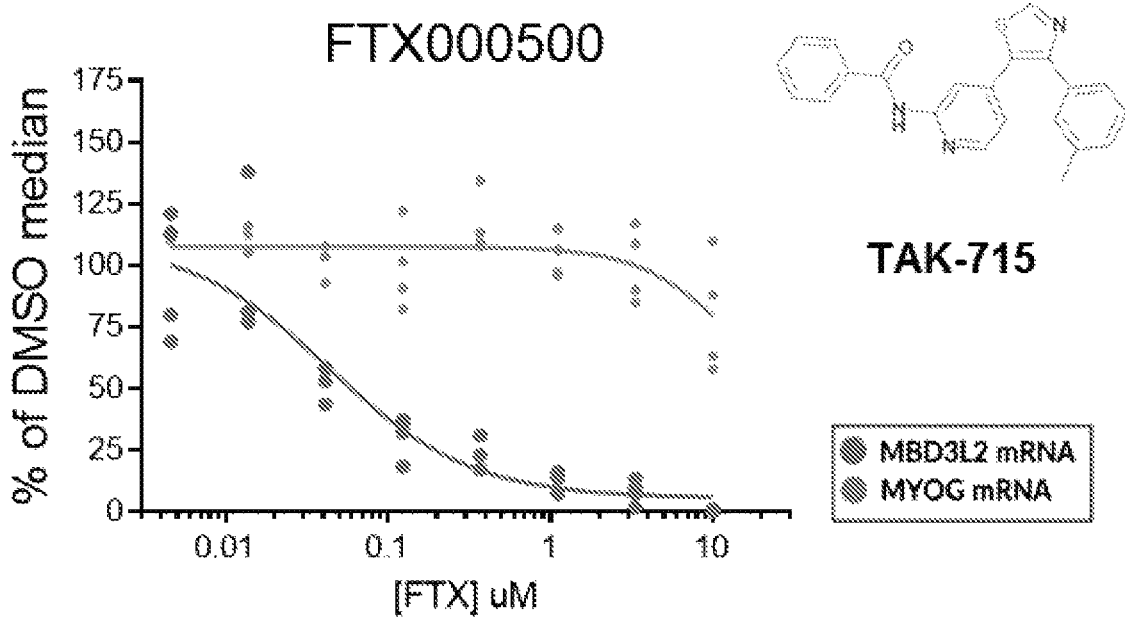

Wild type myotubes and mature patient-derived FSHD myotubes that express DUX4 protein were treated with DMSO vehicle control or multiple concentrations of various p38α/β inhibitors with different ranges of isoform and kinome selectivity, including SB239063 (FIG. 4A), VX-702 (FIG. 4B), Pamapimod (FIG. 4C), and TAK-715 (FIG. 4D). After treatment, the control and treated cells were processed for realtime PCR quantification of MBD3L2 mRNA (DUX4 downstream gene) and myogenin (MYOG) mRNA (control) expression. These p38α/β inhibitors showed potent ($IC_{50}$ approximately <10 nM, FIGS. 4A-D) reduction of MBD3L2 mRNA expression with no impact to MYOG mRNA expression in FSHD myotubes.

Figure 5A:
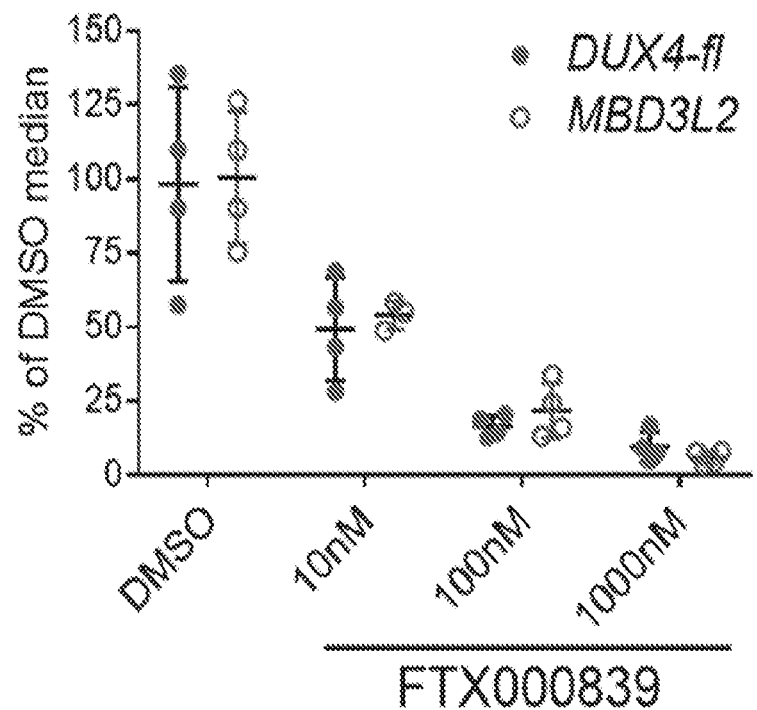
FIGS. 5A and 5B show data from FSHD myotubes treated with Pamapimod.
Figure 5B:
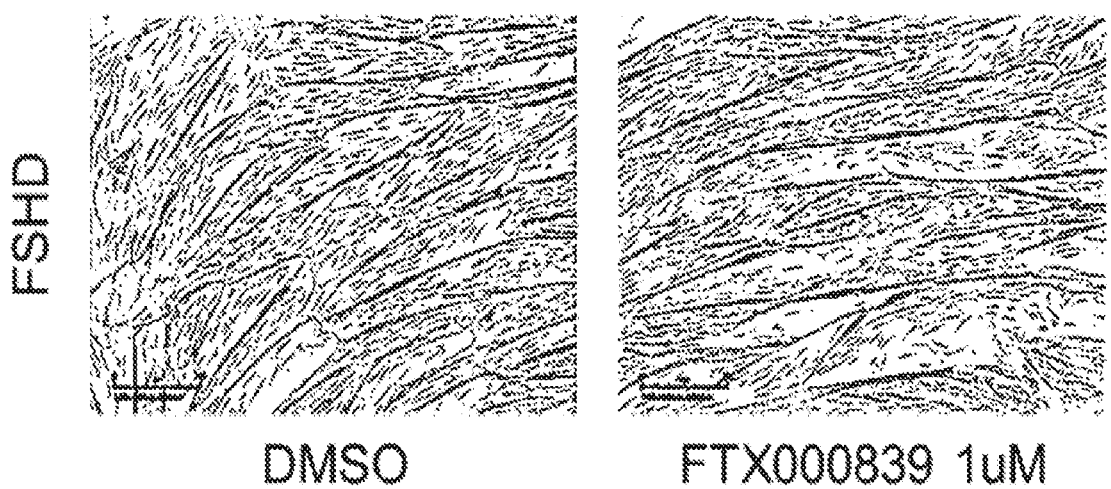

In FSHD myotubes, p38 inhibitors (e.g., Pamapimod) dose-dependently reduced DUX4 mRNA and DUX4 downstream gene MBD3L2 mRNA expression without impacting myotube formation. When compared to DMSO treatment, 10, 100, and 1000 nM FTX000839 (Pamapimod) dose-dependently reduced both DUX4-fl and MBD3L2 downstream gene mRNA levels normalized to POLR2A mRNA, as measured by qPCR and Taqman in FSHD myotubes (FIG. 5A) without impacting differentiation into myotubes (FIG. 5B). The data show that p38 inhibitors dose-dependently reduce MBD3L2 mRNA expression without impacting myogenin mRNA expression.

Example 3

Figure 6A:
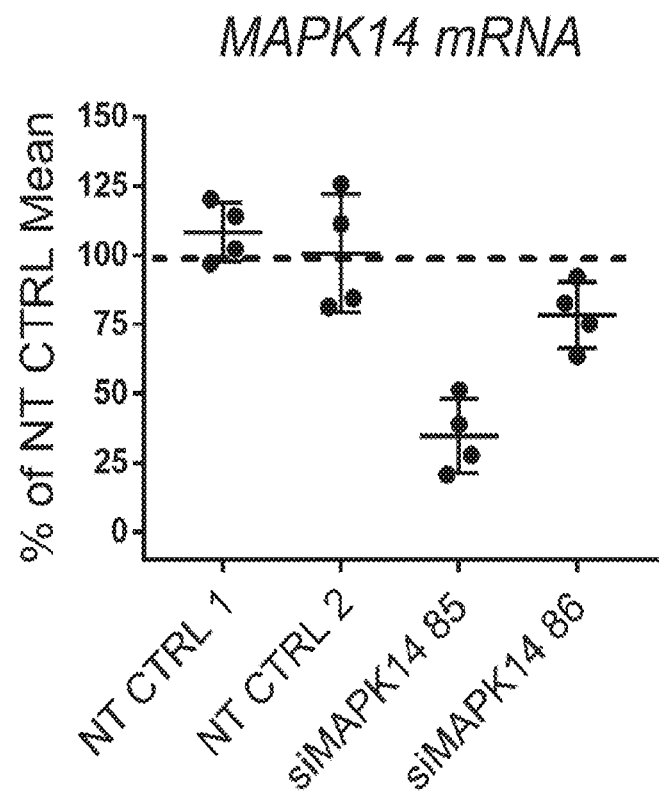
Figure 6B:
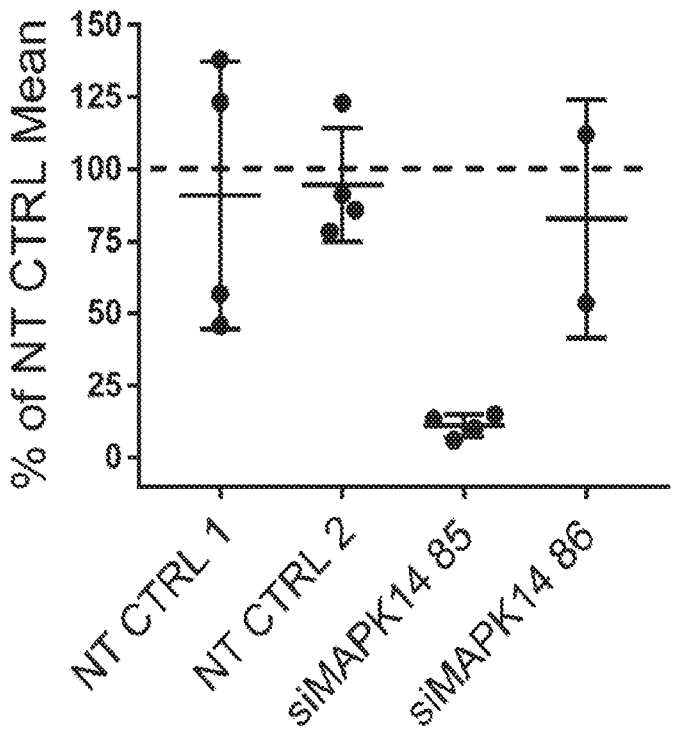

P38 MAPK14 mRNA and MBD3L2 mRNA Reduction Via siRNA Knockdown p38α MAPK14 85 and p38α MAPK14 86 siRNAs were transfected into patient FSHD myotubes as described in Materials and Methods. Each of p38α MAPK14 85 siRNA and p38α MAPK14 86 siRNA (to a lesser extent) reduced p38 MAPK14 expression, as shown in FIG. 6A, and MBD3L2 mRNA (DUX4 target gene) expression, as shown in FIG. 6B, as compared to non-target control siRNAs (NT CTRL 1 and NT CTRL 2). The data shows that genomic reduction of p38α MAPK14 >50% specifically reduced DUX4 and downstream target genes, as exemplified by MBD3L2.

Example 4

MBD3L2 mRNA Reduction Via P38a Kinase Cas9/sgRNA RNPs

CRISPR gRNA targeting of MAPK14 or pLAM (polyadenylation signal sequence for DUX4) was conducted as described in Materials and Methods. CRISPR gRNA targeted to MAPK14 or pLAM (polyadenylation signal sequence for DUX4) resulted in a reduction in expression of MBD3L2 but no MYOG. The data indicates that genomic reduction of p38α MAPK14 specifically reduced DUX4 and downstream target genes, as exemplified by MBD3L2.

Example 5

FTX-1821 Downregulates DUX4 Protein and MBD3L2 mRNA

Patient-derived FSHD myotubes (with 6 repeats of D4Z4 arrays) were treated with DMSO vehicle control and different FTX-1821 concentrations, and DUX4 protein and MBD3L2 mRNA levels were determined as described in Methods and Materials. For DUX4 and MBD3L2, four biological replicates were analyzed. In addition, pHSP27 levels were determined. For pHSP27 quantification, three replicates were obtained in two independent experiments.

Treatment of the FSHD patient derived myotubes with FTX 1821 resulted in a concentration-dependent reduction of DUX4 protein ($IC_{50}$=25 nM) and MBD3L2 mRNA ($IC_{50}$=25 nM) that correlated with the changes observed in phospho HSP27 levels ($IC_{50}$=10 nM) as evidence of target engagement (FIG. 7). The results were indicative of a concentration-dependent reduction of DUX4 protein ($IC_{50}$=25 nM) and MBD3L2 mRNA ($IC_{50}$=10 nM). The reductions in DUX4 protein and MBD3L2 mRNA correlated with the observed changes in p-HSP27 levels ($IC_{50}$=10 nM) as evidence of target engagement. These results indicate that p38α pathway inhibition by FTX-1821 results in potent DUX4 protein and MBD3L2 mRNA downregulation.

Example 6

FTX-1821 Does Not Affect Myotube Formation

Figure 8A:
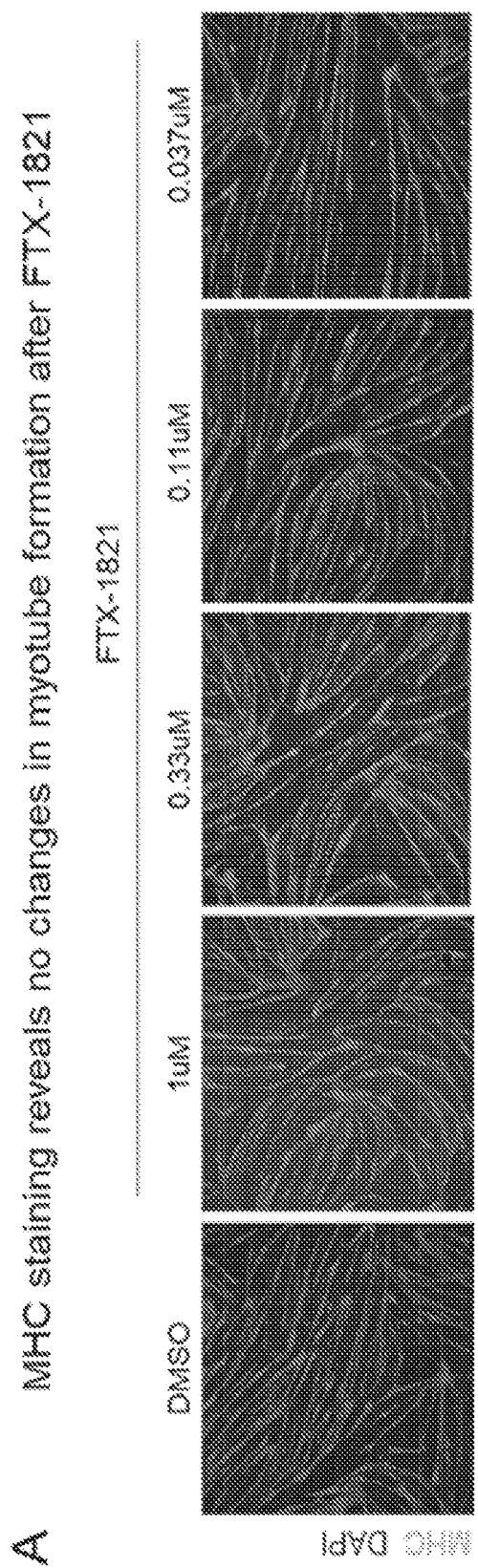

Immortalized FHSD myotubes were differentiated and treated with DMSO vehicle control or FTX-1821 at concentrations of 1 μM, 0.33 μM, 0.11 μM, or 0.037 μM. After 4 days, the cells were fixed and stained with antibodies directed against MHC or DAPI. See FIG. 8A. The nuclei in myotubes were quantified according to MHC staining (FIG. 8B).

The results showed no changes in myotube formation or fusion after treatment with FTX-1821 at concentrations tested.

Example 7

FTX-1821 Reduces Apoptosis in FSHD Myotubes

Figure 9A:
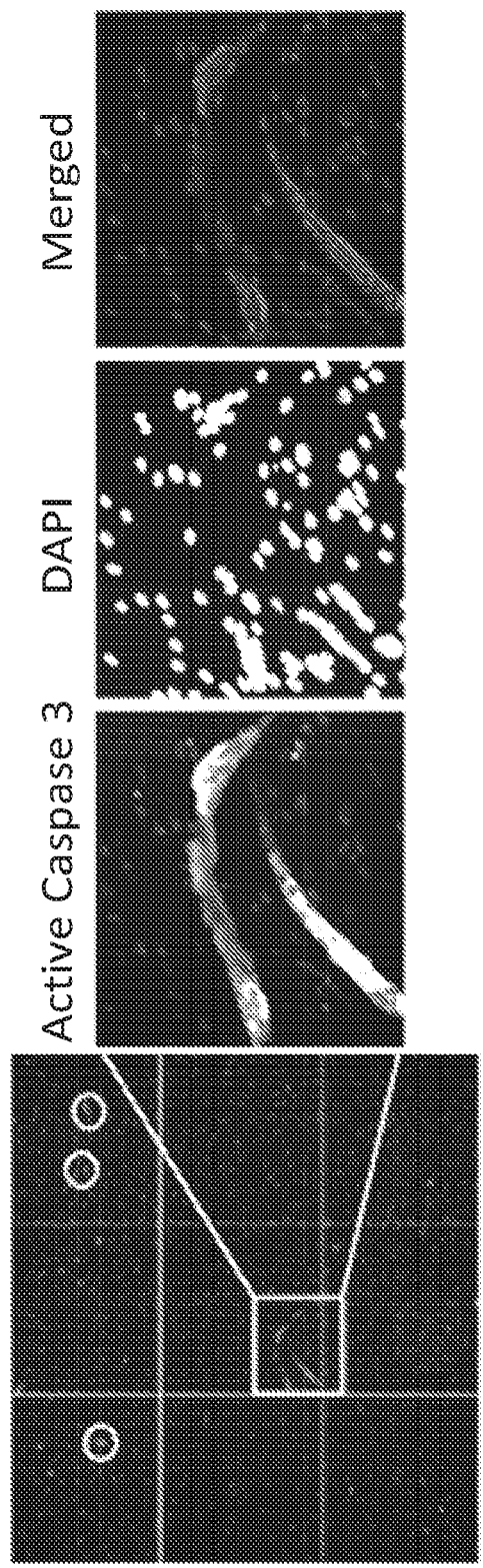
FIGS. 9A and 9B show the results of apoptosis assays in FSHD myotubes in vitro.
Figure 9B:
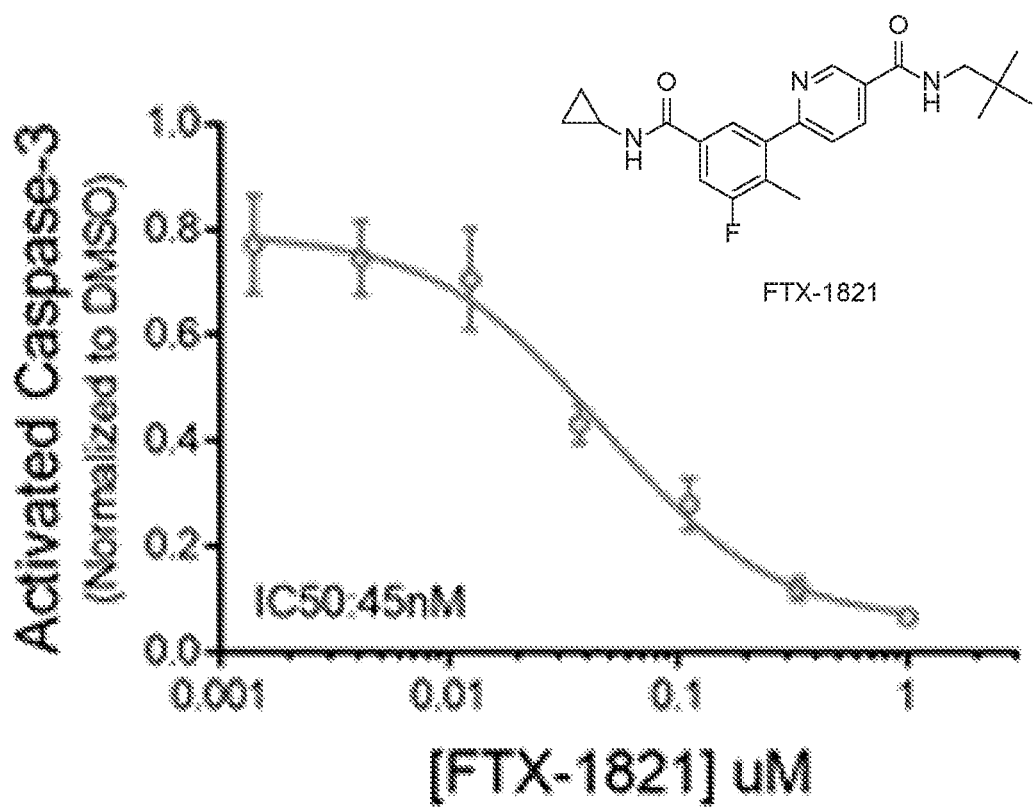

Apoptosis was measured by active Caspase-3 levels in FSHD myotubes in vitro as described in Materials and Methods. Apoptosis was detected in a sporadic manner in a subset of myotubes in culture as shown by the white circles and magnified region in FIG. 9A. Active Caspase-3 signal was quantified in FSHD myotubes that had been treated with FTX-1821 at different concentrations (FIG. 9B). The results showed a dose-dependent reduction of apoptotic signal, as indicated by the reduction in detection of active Caspase 3 ($IC_{50}$=45 nM), and this effect was specific to FSHD myotubes compared to control myotubes. No change in active Caspase-3 signal was observed following DMSO treatment.

Example 8

FTX-1821 Reduces Pathologic DUX4 Transcriptional Program Expression

Studies were conducted as described in Methods and Materials to identify genes in the DUX4 pathway whose expression in down-regulated in FSHD myotubes treated with FTX-1821 as compared to FSHD myotubes treated with DMSO vehicle control. In addition, gene expression was also determined in wild type myotubes treated with DMSO. Three replicates for each condition were analyzed by RNA-seq and genes were clustered by the direction and intensity of change.

Figure 10B:
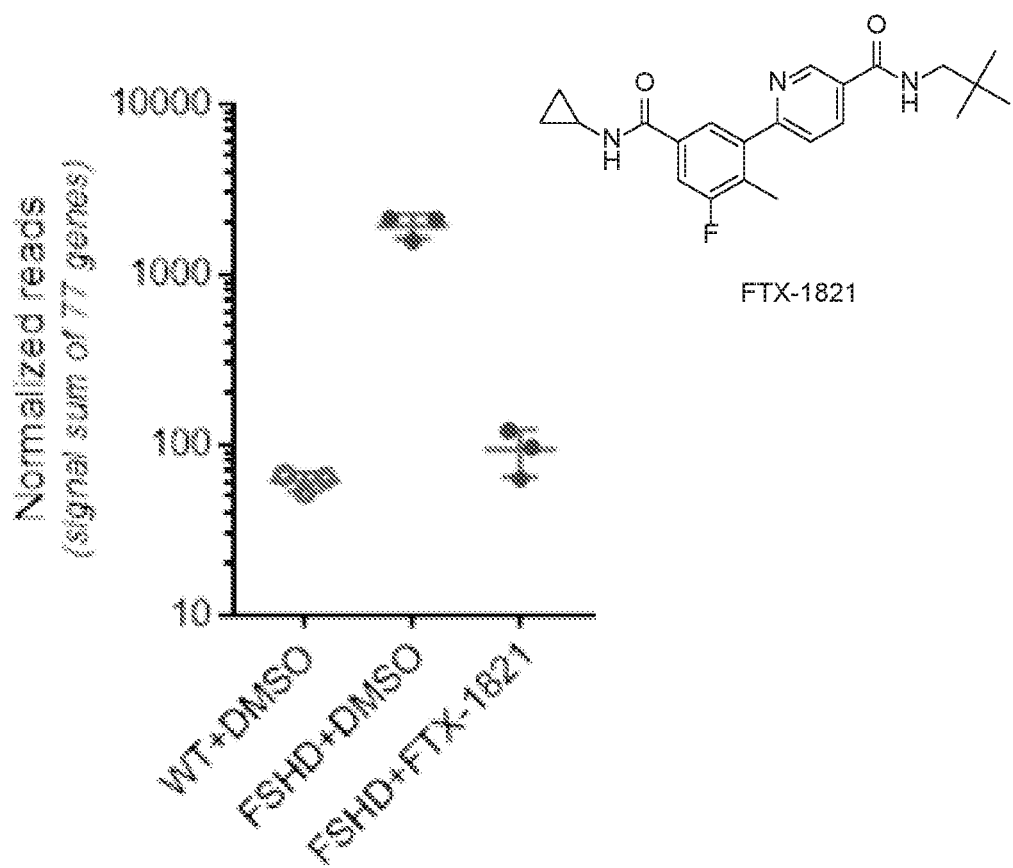

As shown in the heatmap of FIG. 10A, a number of differentially expressed genes were identified by RNA-seq profiling. The bar indicates the normalized changes observed, e.g., genes that were downregulated by FTX-1821 are enriched in samples treated with only DMSO. The expression of these genes was normalized upon treatment with FTX-1821 (1 µM) and closer resembled the observations in wild type cells. Calculated using standard RPKM expression values, the total gene signature was very small and defined at standard statistical cutoffs: 86/19,799 mRNA genes. DUX4-regulated gene signature was a majority of the total signature, and these genes are listed in FIG. 10A. Non-DUX4-regulated genes were minority of the total signature with moderate fold changes: 9/86 mRNA genes=10%; 2-2.7×log FC. FIG. 10B shows the normalized reads, as described in Materials and Methods, of the DUX4 target genes that were downregulated upon treatment with FTX-1821. Three independent replicates per group were analyzed.

Example 9

Reduction of MBD3L2 mRNA in Various FSHD1 Genotypes and Phenotypes

The ability of p38 inhibitors to reduce expression of DUX4 target genes in cells obtained from patients having various different FSHD 1 genotypes was conducted as described in Methods and Materials. Four distinct FSHD patient myoblast lines, i.e., FTCE-016, -020, -197, and -196 (kindly provided Rabi Tawil) were treated with FTX-1821 (1 µM) or FTX-839 (1 µM), and mRNA levels of the DUX4 target gene, MBD3L2, were determined following treatment.

MBD3L2 expression levels were reduced in all of the FSHD lines, resulting in levels similar to those measured in healthy controls, FTCE-396 and FTCE-014 (FIG. 11). This is evidence of DUX4 target gene reduction by p38 inhibitors across myotubes derived from diverse FSHD1 genotypes and phenotypes (similar results were observed for FSHD2, data not shown).

Example 10

Reduction of MBD3L2 mRNA from FSHD 1 and FSHD2 Genotypes and Phenotypes

To assess the treatment effect of p38 selective inhibition using FTX-1821 in FSHD1 and FSHD2 cells, primary myoblast lines were kindly provided by Rabi Tawil at the University of Rochester. FIG. 13 summarizes the genotypes and phenotypes of 13 FSHD1 and 3 FSHD2 patient myoblasts used in the study. The various FSHD1 and FSHD2 myoblasts were treated with DMSO, FTX-1821 or FTX-839 (1 µM), and following treatment, mRNA expression levels of the DUX4 target gene, MBD3L2, were determined. In addition, apoptosis was determined by measuring active caspase-3 in the FSHD1 and FSHD2 lines.

Figure 14A:
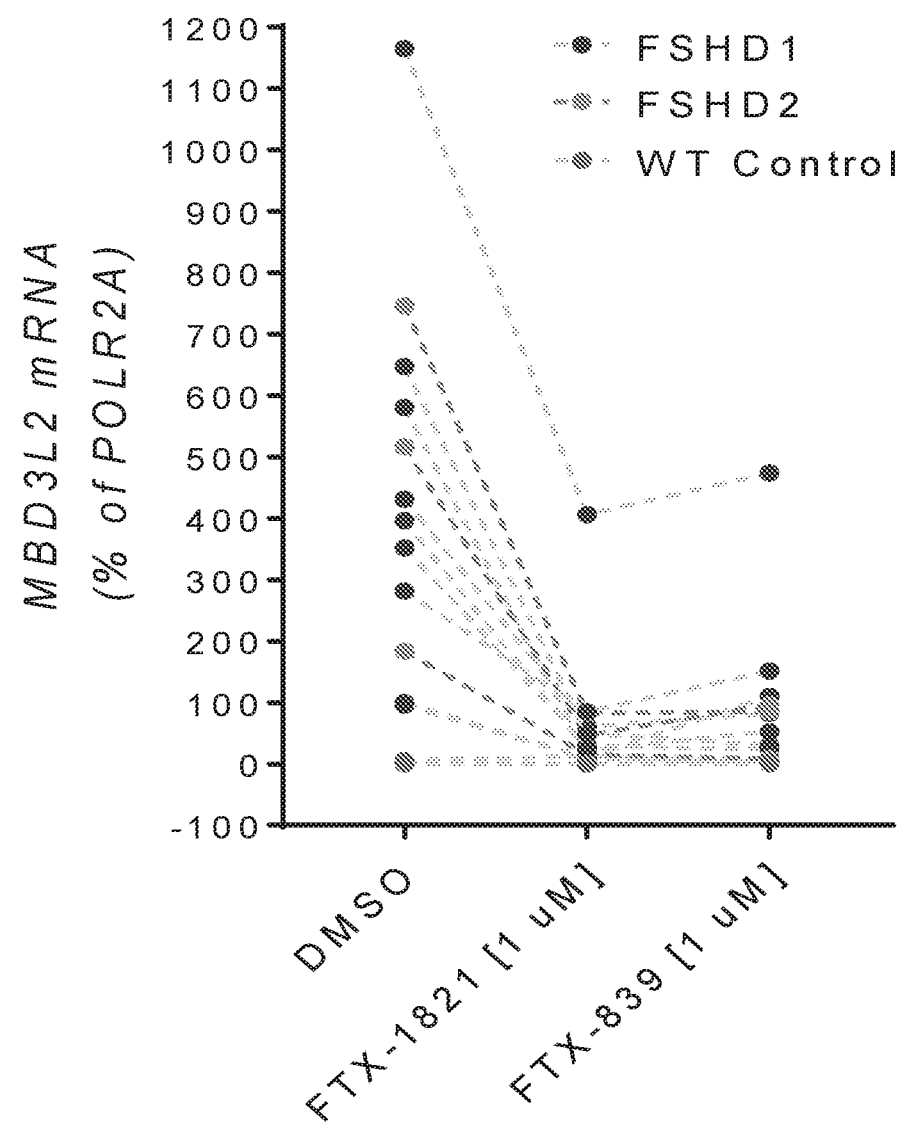
FIGS. 14A and 14B are graphs showing MBD3L2 mRNA expression normalized to POLR2A (by qRT-PCR) (FIG. 14A) and apoptosis as measured by cleaved caspase-3 (FIG. 14B) determined in nine FSHD1 and three FSHD2 patient myotubes (listed in Table 2, FIG. 14B contains only two FSHD2 cell lines) following treatment with FTX-1821, FTX-839, or DMSO vehicle control.
Figure 14B:
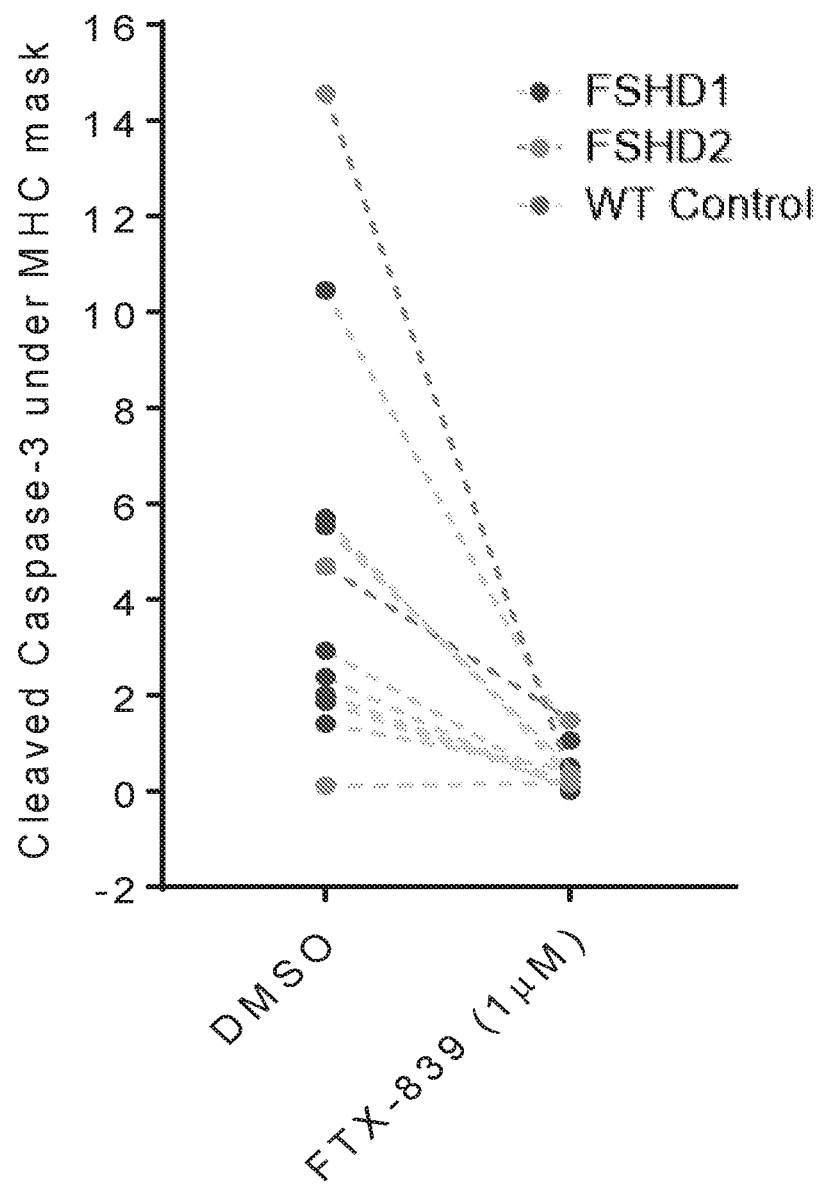

Each of the various FSHD1 and FSHD2 myoblasts showed a reduction of MBD3L2 (FIG. 14A, top 11 lines). The reduction resulted in expression levels similar to those in healthy control lines (CTRL-FTCE-014) (FIG. 14A, bottom 2 lines). In addition, treatment with FTX-839 showed a reduction in apoptosis across both FSHD1 and FSHD2 lines, to a level that was similar to the amount determined in a healthy control line (CTRL-FTCE-014) (FIG. 14B). These results indicate that clinical FSHD biopsy myoblasts, when differentiated into myotubes, show a reduction in both pathologic DUX4 downstream gene expression and resulting cell death across both FSHD1 and FSHD2 genotypes and phenotypes.

Example 11

Target Engagement in Muscle of Wild Type Rats Following Treatment with a Potent and Selective P38 Inhibitor The pharmacokinetic properties of FTX-1821 were studied in an animal model. FTX-1821 was orally dosed to fasted or unfasted male Sprague-Dawley rats (N=6 animals per time point and treatment group), and phospho p38α:total p38α levels were determined. Pharmacodynamic analysis of p38 system target engagement in muscle tissue was performed by measuring the change in phospho MAP kinase-activated protein kinase 2 (MK2) to total MK2 ratio before and after drug treatment. All methods used are described in the Materials and Methods section.

FTX-1821 exhibited plasma pharmacokinetic properties similar to those described previously (Aston et al., 2009; data not shown). These studies additionally demonstrated rapid distribution of FTX-1821 to multiple muscles and plasma. Muscle to plasma exposure ratios were equal to or greater than 1 in the rat when clinically relevant plasma exposures were achieved.

Figure 15:
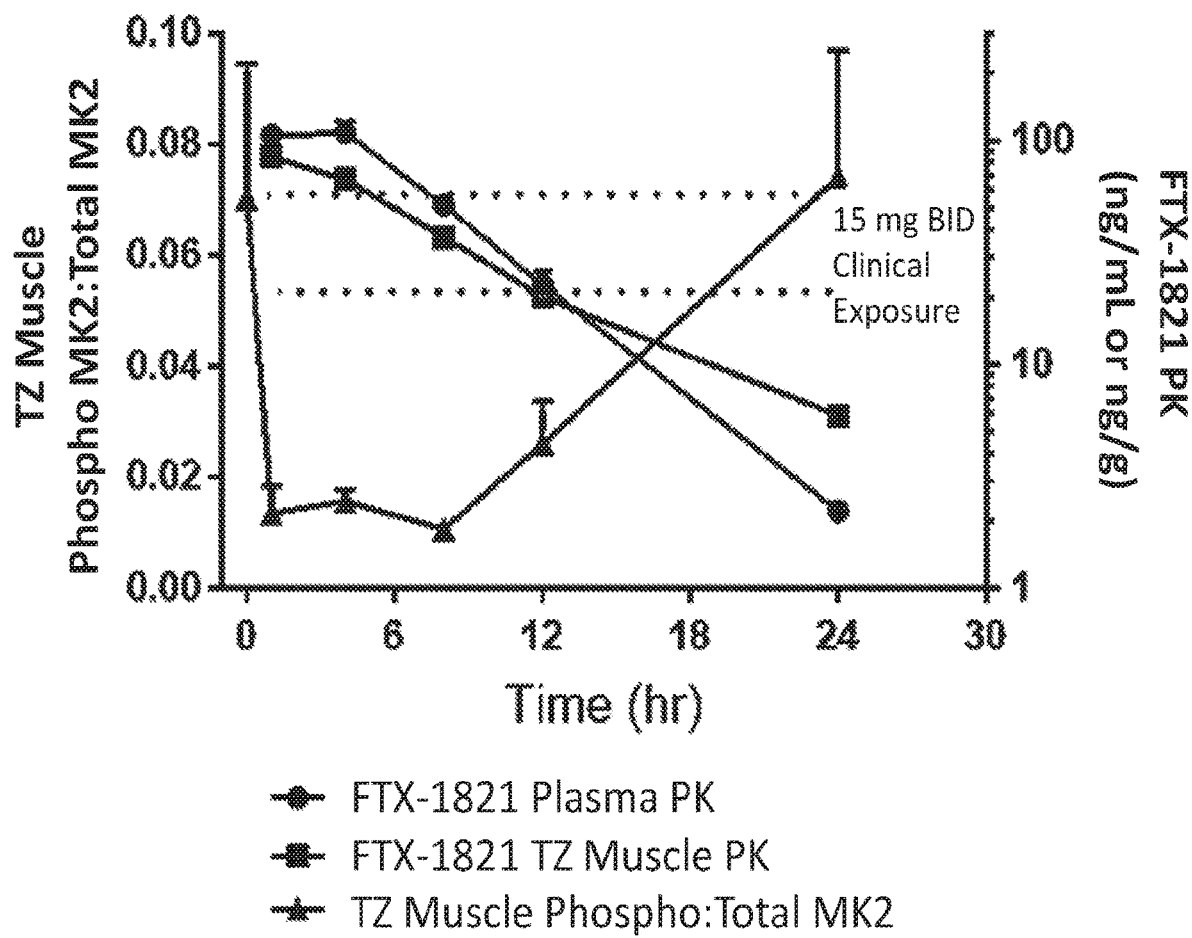
FIG. 15 is a graph showing the time course of plasma exposure, trapezius muscle exposure and p38 target engagement (Phosphorylated p38α:Total p38α Ratio) in the rat following oral administration of 0.3 mg/kg FTX-1821.

Pharmacodynamic analysis demonstrated that a single, oral dose of FTX-1821 (0.3 mg/kg) resulted in clinically relevant plasma concentrations (Barbour et al., 2012) and significantly decreased the phospho MK2 to total MK2 ratio in rat trapezius muscle within 1-hour of drug treatment (FIG. 15). P38 system target engagement persisted for at least 12 hours following the single dose of FTX-1821 (FIG. 15). P38 system target engagement in trapezius muscle was maximal when plasma and muscle concentrations of FTX-1821 were greater than 20 ng.mL or ng.g and declined at timepoints when exposures decreased. The muscle concentrations of FTX-1821 achieved in the rat study are predicted to result in >70% reduction at Cmax in DUX4 dependent target genes in FSHD patient muscle biopsies based upon in vitro data in FSHD myotubes (above).

This pharmacokinetic and pharmacodynamic analysis indicated that maximal inhibition of the p38 system in muscle was achieved when plasma FTX-1821 concentrations were greater than 20 ng/mL and that significant p38 pathway inhibition would be expected in human muscle, with clinical doses of 7.5 or 15 mg BID (Barbour et al., 2012).

Example 12

Inhibition of the DUX4 Genomic Program in FSHD Xenografted Mice Following Treatment with a Potent and Selective P38 Inhibitor FSHD and control muscle xenograft mice were generated by xenografting C6 (FSHD) and A4 (control) IPSC-derived human immortalized isogeneic myoblast cell lines into the bilateral tibialis anterior (TA) muscles of approximately 8-week old male Nod-Rag mice as described by Sakellariou et al., 2016. Following the 4-week long engraftment and INMES procedure, the FSHD xenografted animals were treated with BID injections of either vehicle or FTX-2865 (10 mg/kg) for 8 days (a total of 14 injections) and were sacrificed at approximately the time of maximal plasma concentrations (Tmax) 1-hour after the final morning injection on Day 8. At sacrifice, plasma, trapezius muscle and bilateral tibialis anterior muscles were collected and flash frozen for analysis of pharmacokinetic endpoints, target engagement and DUX4 dependent mRNAs. MBD3L2 was assessed by qPCR using a human specific probe and was normalized to the housekeeping gene CDKN1B. pMK2 and MK2 protein concentrations were assessed by a quantitative MSD assay.

Figure 16:
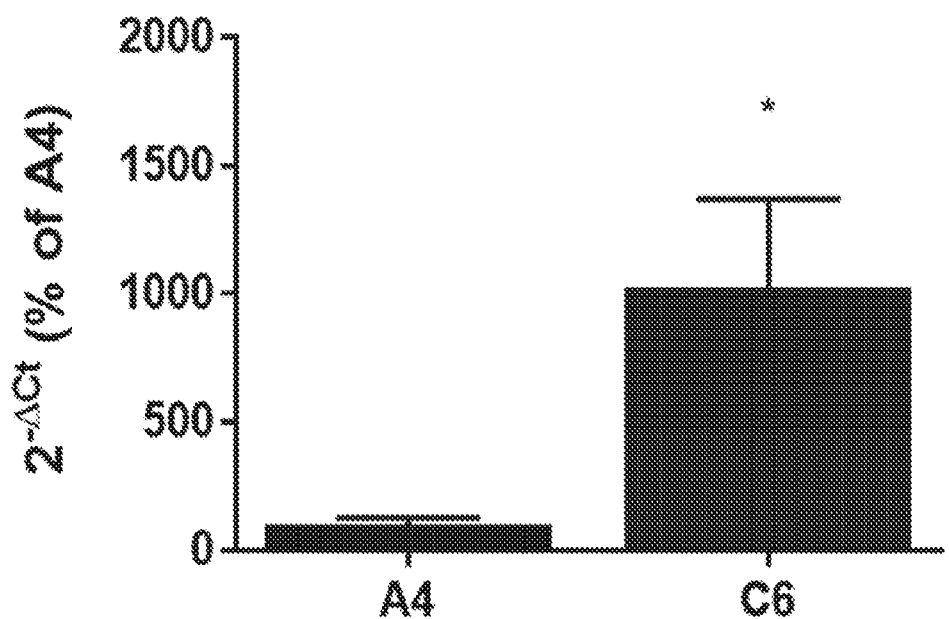
FIG. 16 is a graph showing MBD3L2 mRNA levels in A4 and C6 xenografted TA muscles.

Analysis of TA tissue by qPCR from animals engrafted for 4-6 weeks with A4 or C6 myoblast tissues demonstrated a significant (p<0.05) and >10-fold increase in MBD3L2 and other Dux4 dependent genes (not shown) in the FSHD (C6) vs. control (A4) xenografted TA muscles (FIG. 16). N=8 TA samples per group.

Figure 17:
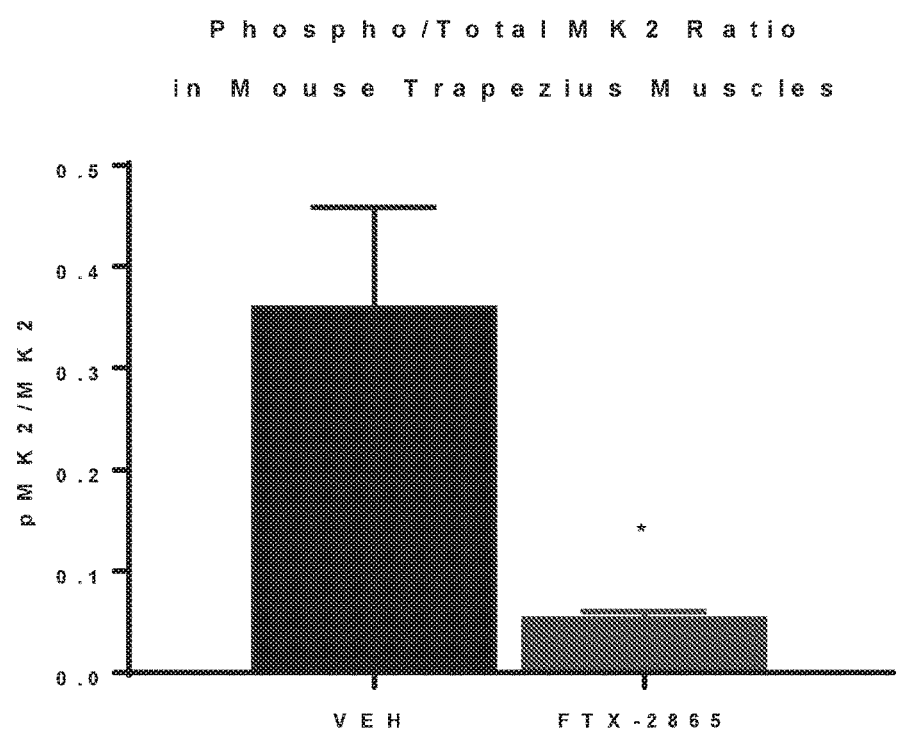
FIG. 17 is a graph showing phosphor/total MC2 ratio in mouse trapezius muscles following treatment with vehicle control or p38 inhibitor, FTX-2865.
Figure 18:
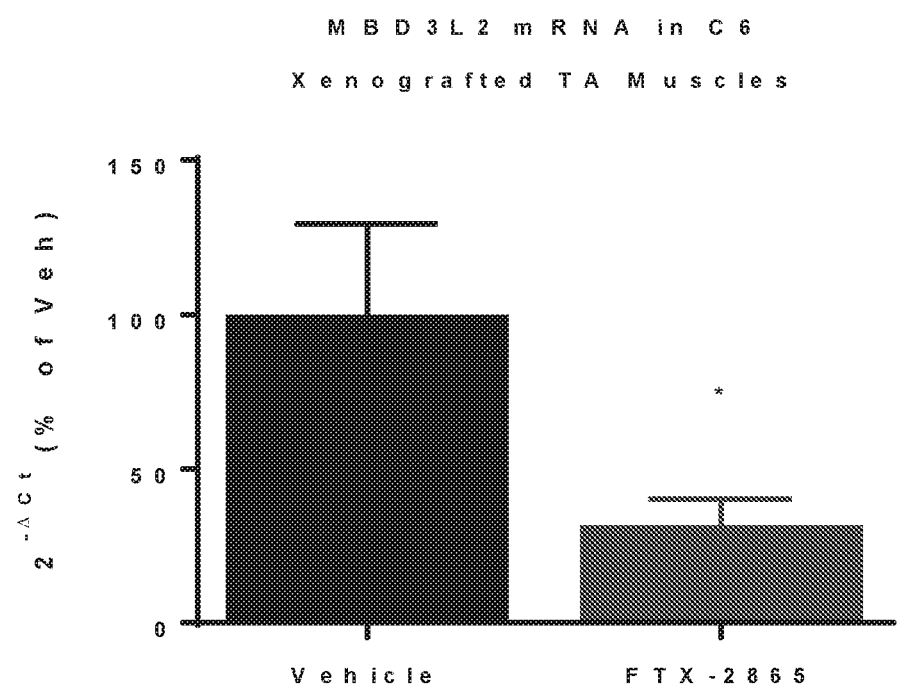
FIG. 18 is a graph showing MBD3L2 mRNA levels in C6 xenografted TA muscles following treatment with vehicle control or p38 inhibitor, FTX-2865.

Treatment of FSHD xenografted animals with the potent and selective p38 inhibitor, FTX-2865, produced p38 system target engagement, as measured by a change in phospho MAP kinase-activated protein kinase 2 (MK2) to total MK2 ratio of >50% in the TA and trapezius muscles of wild-type mice following repeated BID administration of a 10 mg/kg dose given via intraperitoneal (IP) injection (data not shown). FTX-2865 treatment significantly (p<0.05) decreased the ratio of phospho to total MK2 in mouse trapezius muscle, indicating significant p38 system engagement, and also indicating sufficient drug concentrations in the skeletal muscles of the animals to inhibit the p38 system by >80% (FIG. 17; N=8 trapezius samples per group). In addition, FTX-2865 treatment significantly (p<0.05) decreased the expression of MBD3L2 in the FSHD xenografted TA muscles compared to vehicle treated animals, indicating suppression of the pathologic DUX4 gene program by p38 inhibition (FIG. 18; N=5-7 TA samples per group).

REFERENCES

Tawil R., van der Maarel S. M. and Tapscott S. J. Facioscapulohumeral dystrophy: the path to consensus on pathophysiology. Skeletal Muscle 2014, 4:12.

van der Maarel S. M., Frants R. R., Padberg G. W. Facioscapulohumeral muscular dystrophy. Biochimica et Biophysica Acta 2007, 1772:186-194.

Ehrlich M. and Lacey M. Deciphering transcription dysregulation in FSH muscular Dystrophy. J Hum Genet. 2012, 57(8): 477-484.

Cuenda A. and Rousseau, S. 2007. BBA-Mol Cell Res. Review: p38 MAP-Kinases pathway regulation, function and role in human diseases. Vol. 1773: 8, p. 1358-1375.

Himeda C. L., Jones T. I., and Jones P. L. Facioscapulohumeral Muscular Dystrophy As a Model for Epigenetic Regulation and Disease. Antioxid Redox Signal. 2015, 22(16): 1463-1482.

Yao Z., Snider L., Balog J., Lemmers R. J. L. F., Van Der Maarel S. M., Tawil R., and Tapscott S. J. DUX4-induced gene expression is the major molecular signature in FSHD skeletal muscle. Human Molecular Genetics. 2014, 23:20 5342-5352.

Rickard A. M., Petek L. M. and Miller D. G. Endogenous DUX4 expression in FSHD myotubes is sufficient to cause cell death and disrupts RNA splicing and cell migration pathways. Human Molecular Genetics, 2015, 24:20 5901-5914.

Geng L. N., Yao Z., Snider L., Fong A. P., Cech J. N., Young J. M., van der Maarel S. M., Ruzzo W. L., Gentleman R. C., Tawil R., Tapscott S. J. DUX4 activates germline genes, retroelements and immunemediators: Implications for facioscapulohumeral dystrophy. Dev Cell. 2012, 22(1): 38-51.

Wallace L. M., Garwick S. E., Mei W., Belayew A., Coppee F., Ladner K. J., Guttridge D., Yang J., and Harper S. Q. DUX4, a Candidate Gene for Facioscapulohumeral Muscular Dystrophy, Causes p53-Dependent Myopathy In Vivo. Ann Neurol. 2011, 69(3): 540-552.

Homma S., Beermann M.-L., Boyce F. M., and Miller J. B. Expression of FSHD-related DUX4-FL alters proteostasis and induces TDP-43 aggregation. Ann Clin Transl Neurol. 2015, 2(2): 151-166.

Shadle S. C., Zhong J. W., Campbell A. E., Conerly M. L., Jagannathan S., Wong C.-J., Morello T. D., van der Maarel S. M., Tapscott S. J. DUX4-induced dsRNA and MYC mRNA stabilization activate apoptotic pathways in human cell models of facioscapulohumeral dystrophy. PLOS Genetics. 2017, https://doi.org/10.1371/journal.pgen.1006658

Dandapat A., Hartweck L. M., Bosnakovski D., and Kyba M. Expression of the Human FSHD-Linked DUX4 Gene Induces Neurogenesis During Differentiation of Murine Embryonic Stem Cells. Stem Cells Dev. 2013, 22:(17) 2440-2448.

Bosnakovski D., Choi S. H., Strasser J. M., Toso E. A., Walters M. A. and Kyba M. High-throughput screening identifies inhibitors of DUX4-induced myoblast toxicity. Skeletal Muscle. 2014, 4:4.

Mamchaoui K, Trollet C, Bigot A, Negroni E, Chaouch S, Wolff A, et al. Immortalized pathological human myoblasts: towards a universal tool for the study of neuromuscular disorders. Skeletal Muscle 2011, 1:34.

Thorley M, Duguez S, Mazza E M, Valsoni S, Bigot A, Mamchaoui K, Harmon B, Voit T, Mouly V, Duddy W. Skeletal muscle characteristics are preserved in hTERT/cdk4 human myogenic cell lines. Skeletal Muscle 2016, 6:43.

Isin Dalkilic and Louis M Kunkel. Current Opinion in Genetics & Development 2003, 13:231-238.

Zarubin, T. and Han J. Activation and signaling of the p38 MAP kinase pathway. Cell Research. 2005; 15, 11-18.

Aouadi M., Binetruy, B., Caron, L., Le Marchand-Brustel, Y. 2006. Biochimie. Role of MAPKs in development and differentiation: lessons from knockout mice. Biochimie. 2006; 88:9: 1091-1098.

Keren, A., Tamir, Y., Bengal, E. The p38 MAPK signaling pathway: A major regulator of skeletal muscle development. Molecular and Cellular Endocrinology. 2006. Volume 252, Issues 1-2, Pages 224-230.

Kyriakis J M, Avruch J: Mammalian mitogen-activated protein kinase signal transduction pathways activated by stress and inflammation. Physiol Rev 2001, 81:807-869.

Himeda, C L, Debarnot, C, Homma S., Beermann M., Miller J B., Jones P L., Jones T I. Myogenic Enhancers Regulate Expression of the Facioscapulohumeral Muscular Dystrophy-Associated DUX4 Gene. MCB 2014 vol. 34 no. 11 1942-1955.

Dandapat A., Hartweck L. M., Bosnakovski D., and Kyba M. Expression of the Human FSHD-Linked DUX4 Gene Induces Neurogenesis During Differentiation of Murine Embryonic Stem Cells. Stem Cells Dev. 2013, 22:(17) 2440-2448.

Bosnakovski D., Choi S. H., Strasser J. M., Toso E. A., Walters M. A. and Kyba M. High-throughput screening identifies inhibitors of DUX4-induced myoblast toxicity. Skeletal Muscle. 2014, 4:4.

Mamchaoui K, Trollet C, Bigot A, Negroni E, Chaouch S, Wolff A, et al. Immortalized pathological human myoblasts: towards a universal tool for the study of neuromuscular disorders. Skeletal Muscle 2011; 1:34.

Thorley M, Duguez S, Mazza E M, Valsoni S, Bigot A, Mamchaoui K, Harmon B, Voit T, Mouly V, Duddy W. Skeletal muscle characteristics are preserved in hTERT/cdk4 human myogenic cell lines. Skelet Muscle 2016; 6:43.

Zarubin, T. and Han J. Activation and signaling of the p38 MAP kinase pathway. Cell Research. 2005; 15, 11-18.

Aouadi M., Binetruy, B., Caron, L., Le Marchand-Brustel, Y. 2006. Biochimie. Role of MAPKs in development and differentiation: lessons from knockout mice. Biochimie. 2006; 88:9: 1091-1098.

Keren, A., Tamir, Y., Bengal, E. The p38 MAPK signaling pathway: A major regulator of skeletal muscle development. Molecular and Cellular Endocrinology. 2006. Volume 252, Issues 1-2, Pages 224-230.

Kyriakis J M, Avruch J: Mammalian mitogen-activated protein kinase signal transduction pathways activated by stress and inflammation. Physiol Rev 2001, 81:807-869.

Himeda, C L, Debarnot, C, Homma S., Beermann M., Miller J B., Jones P L., Jones T I. Myogenic Enhancers Regulate Expression of the Facioscapulohumeral Muscular Dystrophy-Associated DUX4 Gene. MCB 2014 vol. 34 no. 11 1942-1955.

Wissing, E R, Boyer, J G., Kwong, J Q, Sargent, M A, Karch, J, McNally, E M, Otsu, K, Molkentin J D. p38α MAPK underlies muscular dystrophy and myofiber death through a Bax-dependent mechanism. Hum Mol Genet. 2014 Oct. 15; 23(20): 5452-5463.

Perdiguero, E, Ruiz-Bonilla, V, Gresh, G, Hui, L, Ballestar, E, Sousa-Victor, P, Baeza-Raja, B, Bosch-Comas, A, Esteller, M, Caelles, C, Serrano, A L, Wagner, E F, Muñoz-Cánoves, P. Genetic analysis of p38 MAP kinases in myogenesis: fundamental role of p38α in abrogating myoblast proliferation. EMBO J. 2007 Mar. 7; 26(5): 1245-1256.

Aston, Nicola M.; Bamborough, Paul; Buckton, Jacqueline B.; Edwards, Christopher D.; Holmes, Duncan S.; Jones, Katherine L. et al. (2009): p38alpha mitogen-activated protein kinase inhibitors. Optimization of a series of biphenylamides to give a molecule suitable for clinical progression. In J Med. Chem. 52 (20), pp. 6257-6269.

Barbour, April M.; Sarov-Blat, Lea; Cai, Gengqian; Fossler, Michael J.; Sprecher, Dennis L.; Graggaber, Johann et al. (2013): Safety, tolerability, pharmacokinetics and pharmacodynamics of losmapimod following a single intravenous or oral dose in healthy volunteers. In Br. J Clin Pharmacol. 76 (1), pp. 99-106.

Boudou, T., Legant, W. R., Mu, A., Borochin, M. A., Thavandiran, N., Radisic, M., Chen, C. S. (2012). A Microfabricated Platform to Measure and Manipulate the Mechanics of Engineered Cardiac Microtissues. *Tissue Engineering. Part A,* 18(9-10), 910-919.

Sakellariou, P., O'Neil, A., Mueller, A. L., Stadler, G., Wright, W. E., Roche, J. A., Bloch, R. J. (2016). Neuromuscular electrical stimulation promotes development in mice of mature human muscle from immortalized human myoblasts. Skeletal Muscle 6:4, 1-14.

All publications and patent applications described herein are hereby incorporated by reference in their entireties.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A method of reducing the expression of a DUX4-fl mRNA, a DUX4 polypeptide, or a polypeptide encoded by a downstream target gene of DUX4, in a cell, comprising contacting the cell with an agent that results in a reduction of active p38 protein in the cell, thereby reducing expression of the DUX4 polypeptide or the polypeptide encoded by the downstream target gene of DUX4;
wherein the cell has an increased expression level of the DUX4-fl mRNA, the DUX4 polypeptide, or the polypeptide encoded by the downstream target gene, as compared to the expression level of the DUX4-fl mRNA, the DUX4 polypeptide, or the polypeptide encoded by the downstream target gene, in a control cell obtained from a healthy subject.

2. The method of claim 1, wherein the agent inhibits the expression or activity, or reduces the amount, of the p38 protein, wherein the activity is optionally kinase activity.

3. The method of claim 1, wherein the cell:
(a) has an increased expression level of the DUX4-fl mRNA, the DUX4 polypeptide, or the polypeptide encoded by the downstream target gene, as compared to the expression level of the DUX4-fl mRNA, the DUX4 polypeptide, or the polypeptide encoded by the downstream target gene, in a control cell obtained from a healthy subject;
wherein the increased expression level of the DUX4-fl mRNA, the DUX4 polypeptide, or the polypeptide encoded by the downstream target gene, is due to reduced repression at a D4Z4 locus in the cell;
(b) is associated with facioscapulohumeral muscular dystrophy (FSHD); optionally wherein the cell comprises a deletion of one or more macrosatellite D4Z4 repeats in the subtelomeric region of chromosome 4q35, optionally wherein the cell comprises ≤7 macrosatellite D4Z4 repeats in the subtelomeric region of chromosome 4q35; or
(c) comprises one or more mutations in a Structural Maintenance Of Chromosomes Flexible Hinge Domain Containing 1 (SMCHDJ) gene; optionally wherein the cell comprises at least one non-deleted 4qA allele.

4. The method of claim 1, wherein the expression or the activity of the p38 protein is reduced by at least 10%, at least 20%, at least 30%, at least 40%, at least 50%, at least 60%, at least 70%, at least 80%, at least 90%, at least 95%, at least 98%, at least 99%, or 100%.

5. The method of claim 1, wherein the agent:
(a) inhibits the expression of the p38 protein; optionally wherein the agent binds a polynucleotide encoding the p38 protein, or an antisense polynucleotide thereof; or
(b) comprises or consists of a nucleic acid selected from the group consisting of a DNA, RNA, gRNA, shRNA, siRNA, and an antisense oligonucleotide.

6. The method of claim 1, wherein the agent inhibits the activity of the p38 protein; optionally wherein the agent binds the p38 protein.

7. The method of claim 1, wherein the agent:
(a) comprises or consists of a polypeptide selected from the group consisting of a protein, a peptide, a protein mimetic, a peptidomimetic, and an antibody or functional fragment thereof; or
(b) comprises a small molecule selected from a small organic molecule and a small inorganic molecule.

8. The method of claim 1, wherein the downstream target gene is RFPL2, CCNA1, SLC34A2, TPRX1, KHDC1L, ZSCAN4, PRAMEF20, TRIM49, PRAMEF4, PRAME6, PRAMEF15 or ZNF280A.

\* \* \* \* \*

SEQUENCE LISTING

```
<160> NUMBER OF SEQ ID NOS: 19

<210> SEQ ID NO 1
<211> LENGTH: 360
<212> TYPE: PRT
<213> ORGANISM: Homo sapiens

<400> SEQUENCE: 1

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45
```

```
Arg Val Ala Val Lys Lys Leu Ser Arg Pro Phe Gln Ser Ile Ile His
 50                  55                  60
Ala Lys Arg Thr Tyr Arg Glu Leu Arg Leu Leu Lys His Met Lys His
 65                  70                  75                  80
Glu Asn Val Ile Gly Leu Leu Asp Val Phe Thr Pro Ala Arg Ser Leu
                 85                  90                  95
Glu Glu Phe Asn Asp Val Tyr Leu Val Thr His Leu Met Gly Ala Asp
             100                 105                 110
Leu Asn Asn Ile Val Lys Cys Gln Lys Leu Thr Asp Asp His Val Gln
         115                 120                 125
Phe Leu Ile Tyr Gln Ile Leu Arg Gly Leu Lys Tyr Ile His Ser Ala
130                 135                 140
Asp Ile Ile His Arg Asp Leu Lys Pro Ser Asn Leu Ala Val Asn Glu
145                 150                 155                 160
Asp Cys Glu Leu Lys Ile Leu Asp Phe Gly Leu Ala Arg His Thr Asp
                165                 170                 175
Asp Glu Met Thr Gly Tyr Val Ala Thr Arg Trp Tyr Arg Ala Pro Glu
            180                 185                 190
Ile Met Leu Asn Trp Met His Tyr Asn Gln Thr Val Asp Ile Trp Ser
        195                 200                 205
Val Gly Cys Ile Met Ala Glu Leu Leu Thr Gly Arg Thr Leu Phe Pro
210                 215                 220
Gly Thr Asp His Ile Asp Gln Leu Lys Leu Ile Leu Arg Leu Val Gly
225                 230                 235                 240
Thr Pro Gly Ala Glu Leu Leu Lys Lys Ile Ser Ser Glu Ser Ala Arg
                245                 250                 255
Asn Tyr Ile Gln Ser Leu Thr Gln Met Pro Lys Met Asn Phe Ala Asn
            260                 265                 270
Val Phe Ile Gly Ala Asn Pro Leu Ala Val Asp Leu Leu Glu Lys Met
        275                 280                 285
Leu Val Leu Asp Ser Asp Lys Arg Ile Thr Ala Ala Gln Ala Leu Ala
290                 295                 300
His Ala Tyr Phe Ala Gln Tyr His Asp Pro Asp Asp Glu Pro Val Ala
305                 310                 315                 320
Asp Pro Tyr Asp Gln Ser Phe Glu Ser Arg Asp Leu Leu Ile Asp Glu
                325                 330                 335
Trp Lys Ser Leu Thr Tyr Asp Glu Val Ile Ser Phe Val Pro Pro Pro
            340                 345                 350
Leu Asp Gln Glu Glu Met Glu Ser
        355                 360

<210> SEQ ID NO 2
<211> LENGTH: 4353
<212> TYPE: DNA
<213> ORGANISM: Homo sapiens

<400> SEQUENCE: 2
ttctctcacg aagccccgcc cgcggagagg ttccatattg ggtaaaatct cggctctcgg      60
agagtcccgg gagctgttct cgcgagagta ctgcgggagg ctcccgtttg ctggctcttg     120
gaaccgcgac cactggagcc ttagcgggcg cagcagctgg aacgggagta ctgcgacgca     180
gcccggagtc ggccttgtag gggcgaaggt gcagggagat cgcggcgggc gcagtcttga     240
gcgccggagc gcgtccctgc ccttagcggg gcttgcccca gtcgcagggg cacatccagc     300
cgctgcggct gacagcagcc gcgcgcgcgg gagtctgcgg ggtcgcggca gccgcacctg     360
```

```
cgcgggcgac cagcgcaagg tccccgcccg gctgggcggg cagcaagggc cggggagagg    420
gtgcgggtgc aggcggggc cccacagggc caccttcttg cccggcggct gccgctggaa     480
aatgtctcag gagaggccca cgttctaccg gcaggagctg aacaagacaa tctgggaggt    540
gcccgagcgt taccagaacc tgtctccagt gggctctggc gccatggct ctgtgtgtgc     600 tgcttttgac acaaaaacgg ggttacgtgt ggcagtgaag aagctctcca gaccatttca    660
gtccatcatt catgcgaaaa gaacctacag agaactgcgg ttacttaaac atatgaaaca    720
tgaaaatgtg attggtctgt tggacgtttt tacacctgca aggtctctgg aggaattcaa    780
tgatgtgtat ctggtgaccc atctcatggg ggcagatctg aacaacattg tgaaatgtca    840
gaagcttaca gatgaccatg ttcagttcct tatctaccaa attctccgag gtctaaagta    900
tatacattca gctgacataa ttcacaggga cctaaaacct agtaatctag ctgtgaatga    960
agactgtgag ctgaagattc tggattttgg actggctcgg cacacagatg atgaaatgac   1020
aggctacgtg gccactaggt ggtacagggc tcctgagatc atgctgaact ggatgcatta   1080
caaccagaca gttgatattt ggtcagtggg atgcataatg gccgagctgt tgactggaag   1140
aacattgttt cctggtacag accatattaa ccagcttcag cagattatgc gtctgacagg   1200
aacacccccc gcttatctca ttaacaggat gccaagccat gaggcaagaa actatattca   1260
gtctttgact cagatgccga agatgaactt tgcgaatgta tttattggtg ccaatcccct   1320
ggctgtcgac ttgctggaga gatgcttgt attggactca gataagagaa ttacagcggc    1380
ccaagccctt gcacatgcct actttgctca gtaccacgat cctgatgatg aaccagtggc   1440
cgatccttat gatcagtcct ttgaaagcag ggacctcctt atagatgagt ggaaaagcct   1500
gacctatgat gaagtcatca gctttgtgcc accacccctt gaccaagaag agatggagtc   1560
ctgagcacct ggtttctgtt ctgttgatcc cacttcactg tgagggaag gcctttttcac   1620 gggaactctc caaatattat tcaagtgcct cttgttgcag agatttcctc catggtggaa   1680 ggggggtgtgc gtgcgtgtgc gtgcgtgtta gtgtgtgtgc atgtgtgtgt ctgtctttgt   1740
gggagggtaa gacaatatga acaaactatg atcacagtga ctttacagga ggttgtggat   1800
gctccagggc agcctccacc ttgctcttct ttctgagagt tggctcaggc agacaagagc   1860
tgctgtcctt ttaggaatat gttcaatgca aagtaaaaaa atatgaattg tccccaatcc   1920
cggtcatgct tttgccactt tggcttctcc tgtgaccca ccttgacggt ggggcgtaga    1980
cttgacaaca tcccacagtg gcacggagag aaggcccata ccttctggtt gcttcagacc   2040
tgacaccgtc cctcagtgat acgtacagcc aaaaaggacc aactggcttc tgtgcactag   2100
cctgtgatta acttgcttag tatggttctc agatcttgac agtatatttg aaactgtaaa   2160
tatgtttgtg ccttaaaagg agagaagaaa gtgtagatag ttaaaagact gcagctgctg   2220
aagttctgag ccgggcaagt cgagagggct gttggacagc tgcttgtggg cccggagtaa   2280
tcaggcagcc ttcataggcg gtcatgtgtg catgtgagca catgcgtata tgtgcgtctc   2340
tctttctccc tcacccccag gtgttgccat ttctctgctt acccttcacc tttggtgcag   2400
aggtttcttg aatatctgcc ccagtagtca gaagcaggtt cttgatgtca tgtacttcct   2460
gtgtactctt tatttctagc agagtgagga tgtgttttgc acgtcttgct atttgagcat   2520
gcacagctgc ttgtcctgct ctcttcagga ggcccggtg tcaggcaggt ttgccagtga    2580
agacttcttg ggtagtttag atcccatgtc acctcagctg atattatggc aagtgatatc   2640
acctctcttc agcccctagt gctattctgt gttgaacaca attgatactt caggtgcttt   2700
```

```
tgatgtgaaa atcatgaaaa gaggaacagg tggatgtata gcattttat tcatgccatc    2760 tgttttcaac caactatttt tgaggaatta tcatgggaaa agaccagggc ttttcccagg    2820
aatatcccaa acttcggaaa caagttattc tcttcactcc caataactaa tgctaagaaa    2880
tgctgaaaat caaagtaaaa aattaaagcc cataaggcca gaaactcctt ttgctgtctt    2940
tctctaaata tgattacttt aaaataaaaa agtaacaagg tgtcttttcc actcctatgg    3000
aaaagggtct tcttggcagc ttaacattga cttcttggtt tggggagaaa taaattttgt    3060
ttcagaattt tgtatattgt aggaatcctt tgagaatgtg attccttttg atggggagaa    3120
agggcaaatt atttaatat tttgtatttt caactttata aagataaaat atcctcaggg    3180
gtggagaagt gtcgttttca taacttgctg aatttcaggc attttgttct acatgaggac    3240
tcatatattt aagccttttg tgtaataaga agtataaag tcacttccag tgttggctgt    3300
gtgacagaat cttgtatttg ggccaaggtg tttccatttc tcaatcagtg cagtgataca    3360
tgtactccag agggacaggg tggaccccct gagtcaactg gagcaagaag gaaggaggca    3420
gactgatggc gattccctct cacccgggac tctccccctt tcaaggaaag tgaacctta    3480 aagtaaaggc ctcatctcct ttattgcagt tcaaatcctc accatccaca gcaagatgaa    3540
ttttatcagc catgttggt tgtaaatgct cgtgtgattt cctacagaaa tactgctctg    3600
aatattttgt aataaggtc tttgcacatg tgaccacata cgtgttagga ggctgcatgc    3660
tctggaagcc tggactctaa gctggagctc ttggaagagc tcttcggttt ctgagcataa    3720
tgctcccatc tcctgatttc tctgaacaga aacaaaaga gagaatgagg gaaattgcta    3780
ttttatttgt attcatgaac ttggctgtaa tcagttatgc cgtataggat gtcagacaat    3840
accactggtt aaaataaagc ctattttca aatttagtga gtttctcaag tttattatat    3900
ttttctcttg ttttatttta atgcacaata tggcattata tcaatatcct ttaaactgtg    3960
acctggcata cttgtctgac agatcttaat actactccta acatttagaa atgttgata    4020 aagcttctta gttgtacatt ttttggtgaa gagtatccag gtctttgctg tggatggta    4080 aagcaaagag caaatgaacg aagtattaag cattgggggcc tgtcttatct acactcgagt    4140
gtaagagtgg ccgaaatgac agggctcagc agactgtggc ctgagggcca aatctggccc    4200
accacctgtt tggtgtagcc tgctaagaat ggcttttaca tttttaaatg gttgggaaag    4260
aaaaaaaaag aagtagtaga ttttgtagca tgtgatgtaa gtaatgtaaa acttaaattc    4320
cagtatccat aaataaagtt ttatgagaac aga                                4353
```

<210> SEQ ID NO 3
<211> LENGTH: 364
<212> TYPE: PRT
<213> ORGANISM: Homo sapiens

<400> SEQUENCE: 3

```
Met Ser Gly Pro Arg Ala Gly Phe Tyr Arg Gln Glu Leu Asn Lys Thr
1               5                   10                  15

Val Trp Glu Val Pro Gln Arg Leu Gln Gly Leu Arg Pro Val Gly Ser
            20                  25                  30

Gly Ala Tyr Gly Ser Val Cys Ser Ala Tyr Asp Ala Arg Leu Arg Gln
        35                  40                  45

Lys Val Ala Val Lys Lys Leu Ser Arg Pro Phe Gln Ser Leu Ile His
    50                  55                  60

Ala Arg Arg Thr Tyr Arg Glu Leu Arg Leu Leu Lys His Leu Lys His
65                  70                  75                  80
```

```
Glu Asn Val Ile Gly Leu Leu Asp Val Phe Thr Pro Ala Thr Ser Ile
                85                  90                  95
Glu Asp Phe Ser Glu Val Tyr Leu Val Thr Thr Leu Met Gly Ala Asp
            100                 105                 110
Leu Asn Asn Ile Val Lys Cys Gln Ala Leu Ser Asp Glu His Val Gln
        115                 120                 125
Phe Leu Val Tyr Gln Leu Leu Arg Gly Leu Lys Tyr Ile His Ser Ala
    130                 135                 140
Gly Ile Ile His Arg Asp Leu Lys Pro Ser Asn Val Ala Val Asn Glu
145                 150                 155                 160
Asp Cys Glu Leu Arg Ile Leu Asp Phe Gly Leu Ala Arg Gln Ala Asp
                165                 170                 175
Glu Glu Met Thr Gly Tyr Val Ala Thr Arg Trp Tyr Arg Ala Pro Glu
            180                 185                 190
Ile Met Leu Asn Trp Met His Tyr Asn Gln Thr Val Asp Ile Trp Ser
        195                 200                 205
Val Gly Cys Ile Met Ala Glu Leu Leu Gln Gly Lys Ala Leu Phe Pro
    210                 215                 220
Gly Ser Asp Tyr Ile Asp Gln Leu Lys Arg Ile Met Glu Val Val Gly
225                 230                 235                 240
Thr Pro Ser Pro Glu Val Leu Ala Lys Ile Ser Ser Glu His Ala Arg
                245                 250                 255
Thr Tyr Ile Gln Ser Leu Pro Pro Met Pro Gln Lys Asp Leu Ser Ser
            260                 265                 270
Ile Phe Arg Gly Ala Asn Pro Leu Ala Ile Asp Leu Leu Gly Arg Met
        275                 280                 285
Leu Val Leu Asp Ser Asp Gln Arg Val Ser Ala Ala Glu Ala Leu Ala
    290                 295                 300
His Ala Tyr Phe Ser Gln Tyr His Asp Pro Glu Asp Glu Pro Glu Ala
305                 310                 315                 320
Glu Pro Tyr Asp Glu Ser Val Glu Ala Lys Glu Arg Thr Leu Glu Glu
                325                 330                 335
Trp Lys Glu Leu Thr Tyr Gln Glu Val Leu Ser Phe Lys Pro Pro Glu
            340                 345                 350
Pro Pro Lys Pro Pro Gly Ser Leu Glu Ile Glu Gln
        355                 360

<210> SEQ ID NO 4
<211> LENGTH: 2463
<212> TYPE: DNA
<213> ORGANISM: Homo sapiens

<400> SEQUENCE: 4
cgccgcctcc gccgccctcc gctccgctcg gctcgggctc ggctcgggcg cgggcgcggg      60
gcgcggggct gggcccgggc ggagcggcgg ctgctccgga catgtcgggc cctcgcgccg     120
gcttctaccg gcaggagctg aacaagaccg tgtgggaggt gccgcagcgg ctgcaggggc     180
tgcgcccggt gggctccggc gcctacggct ccgtctgttc ggcctacgac gcccggctgc     240
gccagaaggt ggcggtgaag aagctgtcgc gccccttcca gtcgctgatc cacgcgcgca     300
gaacgtaccg ggagctgcgg ctgctcaagc acctgaagca cgagaacgtc atcgggcttc     360
tggacgtctt cacgccggcc acgtccatcg aggacttcag cgaagtgtac ttggtgacca     420
ccctgatggg cgccgacctg aacaacatcg tcaagtgcca ggcgctgagc gacgagcacg     480
ttcaattcct ggtttaccag ctgctgcgcg ggctgaagta catccactcg gccgggatca     540
```

-continued

| | |
|---|---|
| tccaccggga cctgaagccc agcaacgtgg ctgtgaacga ggactgtgag ctcaggatcc | 600 |
| tggatttcgg gctggcgcgc caggcggacg aggagatgac cggctatgtg ccacgcgct | 660 |
| ggtaccgggc acctgagatc atgctcaact ggatgcatta caaccaaaca gtggatatct | 720 |
| ggtccgtggg ctgcatcatg gctgagctgc tccagggcaa ggccctcttc ccgggaagcg | 780 |
| actacattga ccagctgaag cgcatcatgg aagtggtggg cacacccagc cctgaggttc | 840 |
| tggcaaaaat ctcctcagaa cacgcccgga catatatcca gtccctgccc ccatgcccc | 900 |
| agaaggacct gagcagcatc ttccgtggag ccaaccccct ggccatagac ctccttggaa | 960 |
| ggatgctggt gctggacagt gaccagaggg tcagtgcagc tgaggcactg cccacgcct | 1020 |
| acttcagcca gtaccacgac cccgaggatg agccagaggc cgagccatat gatgagagcg | 1080 |
| ttgaggccaa ggagcgcacg ctggaggagt ggaaggagc cacttaccag gaagtcctca | 1140 |
| gcttcaagcc cccagagcca ccgaagccac ctggcagcct ggagattgag cagtgaggtg | 1200 |
| ctgcccagca gcccctgaga gcctgtggag gggcttgggc ctgcaccctt ccacagctgg | 1260 |
| cctggtttcc tcgagaggca cctcccacac tcctatggtc acagacttct ggcctaggac | 1320 |
| ccctcgcctt caggagaatc tacacgcatg tatgcatgca caaacatgtg tgtacatgtg | 1380 |
| cttgccatgt gtaggagtct gggcacaagt gtccctgggc ctaccttggt cctcctgtcc | 1440 |
| tcttctggct actgcactct ccactgggac ctgactgtgg ggtcctagat gccaaagggg | 1500 |
| ttcccctgcg gagttcccct gtctgtccca ggccgaccca agggagtgtc agccttgggc | 1560 |
| tctcttctgt cccagggctt tctggaggac gcgctgggc cgggacccccg ggagactcaa | 1620 |
| agggagaggt ctcagtggtt agagctgctc agcctggagg taggggctg tcttggtcac | 1680 |
| tgctgagacc cacaggtcta agaggagagg cagagccagt gtgccaccag ctgggcagg | 1740 |
| gacaaccacc aggtgtcaaa tgagaaaagc tgcctggagt cttgtgttca cccgtgggtg | 1800 |
| tgtgtgggca cgtgtggatg agcgtgcact ccccgtgttc atatgtcagg gcacatgtga | 1860 |
| tgtggtgcgt gtgaatctgt gggcgcccaa ggccagcagc catatctggc aagaagctgg | 1920 |
| agccggggtg ggtgtgctgt tgccttccct ctcctcggtt cctgatgcct tgaggggtgt | 1980 |
| ttcagactgg cggctccagt gggccaaagg gcaaccacat gagcatgggc aggggctttc | 2040 |
| tccttggatg tgggaccac agcagcttcc tgaggctggg ggtgggtggg tgggtggttt | 2100 |
| ggccttgagg acgctagggc aggcagcaca cctggatgtg gacttggact cggacacttc | 2160 |
| tgccctgcac cctggcccgc tctctacctc tgcccaccgt tgtggccctg cagccggaga | 2220 |
| tctgaggtgc tctggtctgt gggtcagtcc tctttccttg tcccaggatg gagctgatcc | 2280 |
| agtaacctcg gagacgggac cctgcccaga gctgagttgg gggtgtggct ctgccctgga | 2340 |
| aagggggtga cctcttgcct cgagggggccc agggaagcct gggtgtcaag tgcctgcacc | 2400 |
| aggggtgcac aataaagggg gttctctctc aaaaaaaaaa aaaaaaaaaa aaaaaaaaaa | 2460 |
| aaa | 2463 |

<210> SEQ ID NO 5
<211> LENGTH: 2072
<212> TYPE: DNA
<213> ORGANISM: Homo sapiens

<400> SEQUENCE: 5

| | |
|---|---|
| atggccctcc cgacaccctc ggacagcacc ctccccgcgg aagcccgggg acgaggacgg | 60 |
| cgacggagac tcgtttggac cccgagccaa agcgaggccc tgcgagcctg ctttgagcgg | 120 |

-continued

| | |
|---|---|
| aacccgtacc cgggcatcgc caccagagaa cggctggccc aggccatcgg cattccggag | 180 |
| cccagggtcc agatttggtt tcagaatgag aggtcacgcc agctgaggca gcaccggcgg | 240 |
| gaatctcggc cctggcccgg agacgcggcc ccgccagaag gccggcgaaa gcggaccgcc | 300 |
| gtcaccggat cccagaccgc cctgctcctc cgagcctttg agaaggatcg ctttccaggc | 360 |
| atcgccgccc gggaggagct ggccagagag acgggcctcc cggagtccag gattcagatc | 420 |
| tggtttcaga atcgaagggc caggcacccg ggacagggtg gcaggcgcc cgcgcaggca | 480 |
| ggcggcctgt gcagcgcggc cccggcggg ggtcaccctg ctccctcgtg ggtcgccttc | 540 |
| gcccacaccg gcgcgtgggg aacgggcctt cccgcacccc acgtgccctg cgcgcctggg | 600 |
| gctctcccac aggggctttt cgtgagccag gcagcgaggg ccgccccgc gctgcagccc | 660 |
| agccaggccg cgccggcaga gggatctcc caacctgccc cggcgcgcgg ggatttcgcc | 720 |
| tacgccgccc cggctcctcc ggacggggcg ctctcccacc ctcaggctcc tcgctggcct | 780 |
| ccgcacccgg gcaaaagccg ggaggaccgg gaccccgcagc gcgacggcct gccgggcccc | 840 |
| tgcgcggtgg cacagcctgg gcccgctcaa gcggggccgc agggcaagg ggtgcttgcg | 900 |
| ccacccacgt cccaggggag tccgtggtgg ggctggggcc ggggtcccca ggtcgccggg | 960 |
| gcggcgtggg aaccccaagc cggggcagct ccacctcccc agcccgcgcc cccggacgcc | 1020 |
| tccgcctccg cgcggcaggg gcagatgcaa ggcatcccgg cgccctccca ggcgctccag | 1080 |
| gagccggcgc cctggtctgc actccctgc ggcctgctgc tggatgagct cctggcgagc | 1140 |
| ccggagtttc tgcagcaggc gcaacctctc ctagaaacgg aggccccggg ggagctggag | 1200 |
| gcctcggaag aggccgcctc gctggaagca cccctcagcg aggaagaata ccgggctctg | 1260 |
| ctggaggagc tttaggacgc ggggttggga cggggtcggg tggttcgggg cagggcggtg | 1320 |
| gcctctcttt cgcggggaac acctggctgg ctacggaggg gcgtgtctcc gccccgcccc | 1380 |
| ctccaccggg ctgaccggcc tgggattcct gccttctagg tctaggcccg gtgagagact | 1440 |
| ccacaccgcg gagaactgcc attctttcct gggcatcccg gggatcccag agccggccca | 1500 |
| ggtaccagca ggtgggccgc ctactgcgca cgcgcgggtt tgcgggcagc cgcctgggct | 1560 |
| gtgggagcag cccgggcaga gctctcctgc ctctccacca gcccacccg ccgcctgacc | 1620 |
| gcccctccc caccccacc cccaccccc ggaaaacgcg tcgtcccctg ggctgggtgg | 1680 |
| agaccccgt cccgcgaaac accgggcccc gcgcagcgtc cgggcctgac accgctccgg | 1740 |
| cggctcgcct cctctgcgcc cccgcgccac cgtcgcccgc ccgcccgggc ccctgcagcc | 1800 |
| tcccagctgc cagcacggag cgcctggcgg tcaaaagcat acctctgtct gtctttgccc | 1860 |
| gcttcctggc tagacctgcg cgcagtgcgc accccggctg acgtgcaagg gagctcgctg | 1920 |
| gcctctctgt gcccttgttc ttccgtgaaa ttctggctga atgtctcccc ccaccttccg | 1980 |
| acgctgtcta ggcaaacctg gattagagtt acatctcctg gatgattagt tcagagatat | 2040 |
| attaaaatgc cccctccctg tggatcctat ag | 2072 |

<210> SEQ ID NO 6
<211> LENGTH: 1574
<212> TYPE: DNA
<213> ORGANISM: Homo sapiens

<400> SEQUENCE: 6

| | |
|---|---|
| atggccctcc cgacaccctc ggacagcacc ctcccgcgg aagcccgggg acgaggacgg | 60 |
| cgacggagac tcgtttggac cccgagccaa agcgaggcc tgcgagcctg ctttgagcgg | 120 |
| aacccgtacc cgggcatcgc caccagagaa cggctggccc aggccatcgg cattccggag | 180 |

```
cccagggtcc agatttggtt tcagaatgag aggtcacgcc agctgaggca gcaccggcgg      240
gaatctcggc cctggcccgg gagacgcggc ccgccagaag gccggcgaaa gcggaccgcc      300
gtcaccggat cccagaccgc cctgctcctc cgagcctttg agaaggatcg ctttccaggc      360
atcgccgccc gggaggagct ggccagagag acgggcctcc cggagtccag gattcagatc      420
tggtttcaga atcgaagggc caggcacccg ggacagggtg gcagggcgcc cgcgcaggca      480
ggcggcctgt gcagcgcggc ccccggcggg ggtcaccctg ctccctcgtg ggtcgccttc      540
gcccacaccg gcgcgtgggg aacggggctt cccgcacccc acgtgccctg cgcgcctggg      600
gctctcccac agggggcttt cgtgagccag gcagcgaggg ccgcccccgc gctgcagccc      660
agccaggccg cgccggcaga ggggatctcc caacctgccc cggcgcgcgg ggatttcgcc      720
tacgccgccc cggctcctcc ggacggggcg ctctcccacc ctcaggctcc tcgctggcct      780
ccgcacccgg gcaaaagccg ggaggaccgg gacccgcagc gcgacggcct gccgggcccc      840
tgcgcggtgg cacagcctgg gcccgctcaa gcggggccgc agggccaagg ggtgcttgcg      900
ccacccacgt cccaggggag tccgtggtgg ggctggggcc ggggtcccca ggtcgccggg      960
gcggcgtggg aaccccaagc cggggcagct ccacctcccc agcccgcgcc cccggacgcc     1020
tccgcctccg cgcggcaggg gcagatgcaa ggcatcccgg cgccctccca ggcgctccag     1080
gagccggcgc cctggtctgc actcccctgc ggcctgctgc tggatgagct cctggcgagc     1140
ccggagtttc tgcagcaggc gcaacctctc ctagaaacgg aggccccggg ggagctggag     1200
gcctcggaag aggccgcctc gctggaagca cccctcagcg aggaagaata ccgggctctg     1260
ctggaggagc tttaggacgc ggggtctagg cccggtgaga gactccacac cgcggagaac     1320
tgccattctt tcctgggcat cccgggggatc ccagagccgg cccaggtacc agcagacctg     1380
cgcgcagtgc gcaccccggc tgacgtgcaa gggagctcgc tggcctctct gtgcccttgt     1440
tcttccgtga aattctggct gaatgtctcc ccccaccttc cgacgctgtc taggcaaacc     1500
tggattagag ttacatctcc tggatgatta gttcagagat atattaaaat gcccctccc       1560 tgtggatcct atag                                                        1574
```

<210> SEQ ID NO 7
<211> LENGTH: 424
<212> TYPE: PRT
<213> ORGANISM: Homo sapiens

<400> SEQUENCE: 7

```
Met Ala Leu Pro Thr Pro Ser Asp Ser Thr Leu Pro Ala Glu Ala Arg
1               5                   10                  15

Gly Arg Gly Arg Arg Arg Arg Leu Val Trp Thr Pro Ser Gln Ser Glu
                20                  25                  30

Ala Leu Arg Ala Cys Phe Glu Arg Asn Pro Tyr Pro Gly Ile Ala Thr
            35                  40                  45

Arg Glu Arg Leu Ala Gln Ala Ile Gly Ile Pro Glu Pro Arg Val Gln
        50                  55                  60

Ile Trp Phe Gln Asn Glu Arg Ser Arg Gln Leu Arg Gln His Arg Arg
65                  70                  75                  80

Glu Ser Arg Pro Trp Pro Gly Arg Arg Gly Pro Glu Gly Arg Arg
                85                  90                  95

Lys Arg Thr Ala Val Thr Gly Ser Gln Thr Ala Leu Leu Leu Arg Ala
            100                 105                 110

Phe Glu Lys Asp Arg Phe Pro Gly Ile Ala Ala Arg Glu Glu Leu Ala
```

```
            115                 120                 125
Arg Glu Thr Gly Leu Pro Glu Ser Arg Ile Gln Ile Trp Phe Gln Asn
        130                 135                 140

Arg Arg Ala Arg His Pro Gly Gln Gly Gly Arg Ala Pro Ala Gln Ala
145                 150                 155                 160

Gly Gly Leu Cys Ser Ala Ala Pro Gly Gly His Pro Ala Pro Ser
                165                 170                 175

Trp Val Ala Phe Ala His Thr Gly Ala Trp Gly Thr Gly Leu Pro Ala
                180                 185                 190

Pro His Val Pro Cys Ala Pro Gly Ala Leu Pro Gln Gly Ala Phe Val
            195                 200                 205

Ser Gln Ala Ala Arg Ala Ala Pro Ala Leu Gln Pro Ser Gln Ala Ala
        210                 215                 220

Pro Ala Glu Gly Ile Ser Gln Pro Ala Pro Ala Arg Gly Asp Phe Ala
225                 230                 235                 240

Tyr Ala Ala Pro Ala Pro Pro Asp Gly Ala Leu Ser His Pro Gln Ala
                245                 250                 255

Pro Arg Trp Pro Pro His Pro Gly Lys Ser Arg Glu Asp Arg Asp Pro
            260                 265                 270

Gln Arg Asp Gly Leu Pro Gly Pro Cys Ala Val Ala Gln Pro Gly Pro
        275                 280                 285

Ala Gln Ala Gly Pro Gln Gly Gln Gly Val Leu Ala Pro Pro Thr Ser
290                 295                 300

Gln Gly Ser Pro Trp Trp Gly Trp Gly Arg Gly Pro Gln Val Ala Gly
305                 310                 315                 320

Ala Ala Trp Glu Pro Gln Ala Gly Ala Ala Pro Pro Gln Pro Ala
                325                 330                 335

Pro Pro Asp Ala Ser Ala Ser Ala Arg Gln Gly Gln Met Gln Gly Ile
            340                 345                 350

Pro Ala Pro Ser Gln Ala Leu Gln Glu Pro Ala Pro Trp Ser Ala Leu
        355                 360                 365

Pro Cys Gly Leu Leu Leu Asp Glu Leu Leu Ala Ser Pro Glu Phe Leu
370                 375                 380

Gln Gln Ala Gln Pro Leu Leu Glu Thr Glu Ala Pro Gly Glu Leu Glu
385                 390                 395                 400

Ala Ser Glu Glu Ala Ala Ser Leu Glu Ala Pro Leu Ser Glu Glu Glu
                405                 410                 415

Tyr Arg Ala Leu Leu Glu Glu Leu
            420

<210> SEQ ID NO 8
<211> LENGTH: 20
<212> TYPE: DNA
<213> ORGANISM: Artificial Sequence
<220> FEATURE:
<223> OTHER INFORMATION: Made in Lab

<400> SEQUENCE: 8
gtattactga tattggtggg                                            20

<210> SEQ ID NO 9
<211> LENGTH: 20
<212> TYPE: DNA
<213> ORGANISM: Artificial Sequence
<220> FEATURE:
<223> OTHER INFORMATION: Made in Lab
```

```
<400> SEQUENCE: 9
gctgaacaag acaatctggg                                               20

<210> SEQ ID NO 10
<211> LENGTH: 20
<212> TYPE: DNA
<213> ORGANISM: Artificial Sequence
<220> FEATURE:
<223> OTHER INFORMATION: Made in Lab

<400> SEQUENCE: 10
ctgcttttga cacaaaaacg                                               20

<210> SEQ ID NO 11
<211> LENGTH: 20
<212> TYPE: DNA
<213> ORGANISM: Artificial Sequence
<220> FEATURE:
<223> OTHER INFORMATION: Made in Lab

<400> SEQUENCE: 11
cttatctacc aaattctccg                                               20

<210> SEQ ID NO 12
<211> LENGTH: 20
<212> TYPE: DNA
<213> ORGANISM: Artificial Sequence
<220> FEATURE:
<223> OTHER INFORMATION: Made in Lab

<400> SEQUENCE: 12
agaatttcac ggaagaacaa                                               20

<210> SEQ ID NO 13
<211> LENGTH: 20
<212> TYPE: DNA
<213> ORGANISM: Artificial Sequence
<220> FEATURE:
<223> OTHER INFORMATION: Made in Lab

<400> SEQUENCE: 13
caggtttgcc tagacagcgt                                               20

<210> SEQ ID NO 14
<211> LENGTH: 20
<212> TYPE: DNA
<213> ORGANISM: Artificial Sequence
<220> FEATURE:
<223> OTHER INFORMATION: Made in Lab

<400> SEQUENCE: 14
caggtttgcc tagacagcgt                                               20

<210> SEQ ID NO 15
<211> LENGTH: 20
<212> TYPE: DNA
<213> ORGANISM: Artificial Sequence
<220> FEATURE:
<223> OTHER INFORMATION: Made in Lab

<400> SEQUENCE: 15
aatcttctat aggatccaca                                               20

<210> SEQ ID NO 16
<211> LENGTH: 21
```

```
<212> TYPE: DNA
<213> ORGANISM: Artificial Sequence
<220> FEATURE:
<223> OTHER INFORMATION: Made in Lab

<400> SEQUENCE: 16
uagauuacua gguuuuaggt c                                        21

<210> SEQ ID NO 17
<211> LENGTH: 21
<212> TYPE: DNA
<213> ORGANISM: Artificial Sequence
<220> FEATURE:
<223> OTHER INFORMATION: Made in Lab

<400> SEQUENCE: 17
ccuaaaaccu aguaaucuat t                                        21

<210> SEQ ID NO 18
<211> LENGTH: 16
<212> TYPE: DNA
<213> ORGANISM: Artificial Sequence
<220> FEATURE:
<223> OTHER INFORMATION: Made in Lab

<400> SEQUENCE: 18
cagcgtcgga aggtgg                                              16

<210> SEQ ID NO 19
<211> LENGTH: 15
<212> TYPE: DNA
<213> ORGANISM: Artificial Sequence
<220> FEATURE:
<223> OTHER INFORMATION: Made in Lab

<400> SEQUENCE: 19
aacacgtcta tacgc                                               15
```